United States Patent
Willis et al.

(10) Patent No.: US 7,763,404 B2
(45) Date of Patent: Jul. 27, 2010

(54) METHODS AND APPARATUS FOR CHANGING THE OPTICAL PROPERTIES OF RESISTS

(75) Inventors: James E. Willis, Buellton, CA (US); Manuel Perez, Martinsville, NJ (US); Asao Yamashita, Fishkill, NY (US)

(73) Assignee: Tokyo Electron Limited, Tokyo (JP)

( * ) Notice: Subject to any disclaimer, the term of this patent is extended or adjusted under 35 U.S.C. 154(b) by 974 days.

(21) Appl. No.: 11/535,247

(22) Filed: Sep. 26, 2006

(65) Prior Publication Data

US 2008/0076045 A1    Mar. 27, 2008

(51) Int. Cl.
    *G03F 9/00*    (2006.01)
(52) U.S. Cl. .............................. 430/30; 430/5; 430/311
(58) Field of Classification Search .................. 430/30, 430/5, 311
    See application file for complete search history.

(56) References Cited

U.S. PATENT DOCUMENTS

| | | | |
|---|---|---|---|
| 6,428,894 B1 | 8/2002 | Babich et al. | |
| 6,608,690 B2 | 8/2003 | Niu et al. | |
| 6,609,086 B1 | 8/2003 | Bao et al. | |
| 6,768,983 B1 | 7/2004 | Jakatdar et al. | |
| 6,785,638 B2 | 8/2004 | Niu et al. | |
| 6,839,145 B2 | 1/2005 | Niu et al. | |
| 6,891,626 B2 | 5/2005 | Niu et al. | |
| 6,928,395 B2 | 8/2005 | Niu et al. | |
| 6,943,900 B2 | 9/2005 | Niu et al. | |
| 6,947,141 B2 | 9/2005 | Bischoff et al. | |
| 7,072,049 B2 | 7/2006 | Niu et al. | |
| 7,136,796 B2 | 11/2006 | Jakatdar et al. | |
| 7,175,966 B2 | 2/2007 | Babich et al. | |
| 7,300,730 B1 | 11/2007 | Willis et al. | |
| 2004/0017574 A1 | 1/2004 | Vuong et al. | |
| 2004/0267397 A1 | 12/2004 | Doddi et al. | |
| 2007/0243491 A1 | 10/2007 | Wu et al. | |
| 2007/0250200 A1 | 10/2007 | Scheer et al. | |

OTHER PUBLICATIONS

Deforest, "Photoresist Materials and Processes", McGraw Hill Book Company, New York, Chap. 2, 1975.
Moreau, "Semiconductor Lithography, Principles, Practices and Materials", Plenum Press, New York, Chaps. 2 and 4.
Office Action issued in U.S. Appl. No. 11/535,407 mailed Feb. 5, 2009.
Office Action issued in U.S. Appl. No. 11/535,384 mailed Feb. 5, 2009.
Office Action issued in U.S. Appl. No. 11/535,359 mailed Feb. 5, 2009.
Office Action issued in U.S. Appl. No. 11/535,320 mailed Nov. 19, 2008.
Office Action issued in U.S. Appl. No. 11/535,278 mailed Nov. 25, 2008.

*Primary Examiner*—Christopher G Young

(57) ABSTRACT

The present invention provides methods and system for improving the accuracy of measurements made using optical metrology. The present invention relates to methods and systems for changing the optical properties of tunable resists that can be used in the production of electronic devices such as integrated circuits. Further, the invention provides methods and systems for using a modifiable resist layer that provides a first set of optical properties before exposure and a second set of optical properties after exposure.

42 Claims, 12 Drawing Sheets

FIG. 9    900

METHODS AND APPARATUS FOR CHANGING THE OPTICAL PROPERTIES OF RESISTS

CROSS-REFERENCE TO RELATED APPLICATIONS

This application is related to the following applications: application Ser. No. 11/535,320, entitled "Methods and Apparatus For Using an Optically Tunable Soft Mask Profile Library; application Ser. No. 11/535,278, entitled "Methods and Apparatus for Using an Optically Tunable Soft Mask to Create a Profile Library; application Ser. No. 11/535,359, entitled "Improving the Accuracy of Optical Metrology Measurements"; application Ser. No. 11/535,384, entitled "Improving the Accuracy of Optical Metrology Measurements"; application Ser. No. 11/535,407, entitled "Improving the Accuracy of Optical Metrology Measurements", and application Ser. No. 11/535,429, entitled "Creating an Optically Tunable Anti-Reflective Coating, filed concurrently herewith. The contents of each of these applications are herein incorporated by reference in their entireties.

BACKGROUND OF THE INVENTION

1. Field of the Invention

The present invention relates to optical metrology, and more particularly to improving the accuracy of measurements made using optical metrology. The present invention relates to a method and apparatus for improving the optical properties of 243 nm soft masks, 193 nm soft masks, 157 nm soft masks, extreme UV soft masks, x-ray wavelength sensitive soft masks, and electron beam sensitive soft masks to improve the accuracy of lithographic features and critical dimensions.

2. Description of the Related Art

Optical metrology involves directing an incident beam at a structure, measuring the resulting diffracted beam, and analyzing the diffracted beam to determine various characteristics, such as the profile of the structure. In semiconductor manufacturing, optical metrology is typically used for quality assurance.

In general, photoresist compositions comprise at least a resin binder component and a photoactive agent. Photoresist compositions are described in Deforest, Photoresist Materials and Processes, McGraw Hill Book Company, New York, ch. 2, 1975 and by Moreau, Semiconductor Lithography, Principles, Practices and Materials, Plenum Press, New York, ch. 2 and 4, both incorporated herein by reference for their teaching of photoresist compositions and methods of making and using the same.

For example, after fabricating a periodic grating in proximity to a semiconductor chip on a semiconductor wafer, an optical metrology system is used to determine the profile of the periodic grating. By determining the profile of the periodic grating, the quality of the fabrication process utilized to form the periodic grating, and by extension the semiconductor chip proximate the periodic grating, can be evaluated.

Conventional optical metrology can be used to determine the deterministic profile of a structure formed on a semiconductor wafer. For example, conventional optical metrology can be used to determine the critical dimension of a structure. However, the wafer may be formed with various processing effects that can decrease the accuracy of the optical measurements.

SUMMARY OF THE INVENTION

The present invention relates to optical metrology, and more particularly to improving the accuracy of measurements made using optical metrology. The present invention relates to methods and apparatus for changing the optical properties of tunable resists that can be used in the production of electronic devices such as integrated circuits. Further, the invention provides a modifiable resist layer for providing a first set of optical properties before exposure and a second set of optical properties after exposure. The resist layer can include chemically amplified resists, and operate at wavelengths below 300 nm, and can be used to improve the accuracy of the critical dimensions and/or parameters of lithographic and/or etched features.

The invention provides a method of improving an optical metrology process, and the method can comprise providing a substrate having a material layer thereon; depositing a resist layer on the material layer, and the resist layer can comprise a first set of optical properties optimized, tuned and/or enhanced for an exposure process. Then, the resist layer can be exposed to patterned radiation created using a reticle and a radiation source, and the radiation source has a wavelength below approximately 300 nm. Next, a plurality of un-enhanced structures can be created in the resist layer by developing the exposed resist layer, and the plurality of un-enhanced structures comprise at least one un-enhanced measurement structure. In addition, a plurality of enhanced structures can be created in the resist layer by enhancing the plurality of un-enhanced structures, and at least one enhanced measurement structure can be created by enhancing the at least one un-enhanced measurement structure, and the plurality of enhanced structures can be characterized by a second set of optical properties.

In addition, the invention provides a system for improving an optical metrology process, and the system can comprise a transfer subsystem for providing a substrate having a material layer thereon; and a lithography subsystem for depositing a resist layer on the material layer, wherein the resist layer comprises a first set of optical properties optimized, tuned and/or enhanced for an exposure process, for exposing the resist layer to patterned radiation created using a reticle and a radiation source, wherein the radiation source has a wavelength below approximately 300 nm, for creating a plurality of un-enhanced structures in the resist layer by developing the exposed resist layer, wherein the plurality of un-enhanced structures comprise at least one un-enhanced measurement structure, and for creating a plurality of enhanced structures in the resist layer by enhancing the plurality of un-enhanced structures, wherein at least one enhanced measurement structure is created by enhancing the at least one un-enhanced measurement structure, the plurality of enhanced structures being characterized by a second set of optical properties.

Other embodiments of the invention provide a procedure for improving an optical metrology process, and the procedure can comprise receiving a substrate, wherein the substrate comprises a plurality of dies and a number of measurement sites, each die having a first patterned resist layer on top of at least one other layer, and at least one measurement site having a periodic measurement structure therein; determining an accuracy value for the substrate; modifying at least one optical property of the substrate, when the accuracy value is not within limits established for an enhanced substrate; and processing the substrate, when the accuracy value is within limits established for an enhanced substrate.

Other aspects of the invention will be made apparent from the description that follows and from the drawings appended hereto.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF SEVERAL EMBODIMENTS

Figure 1:
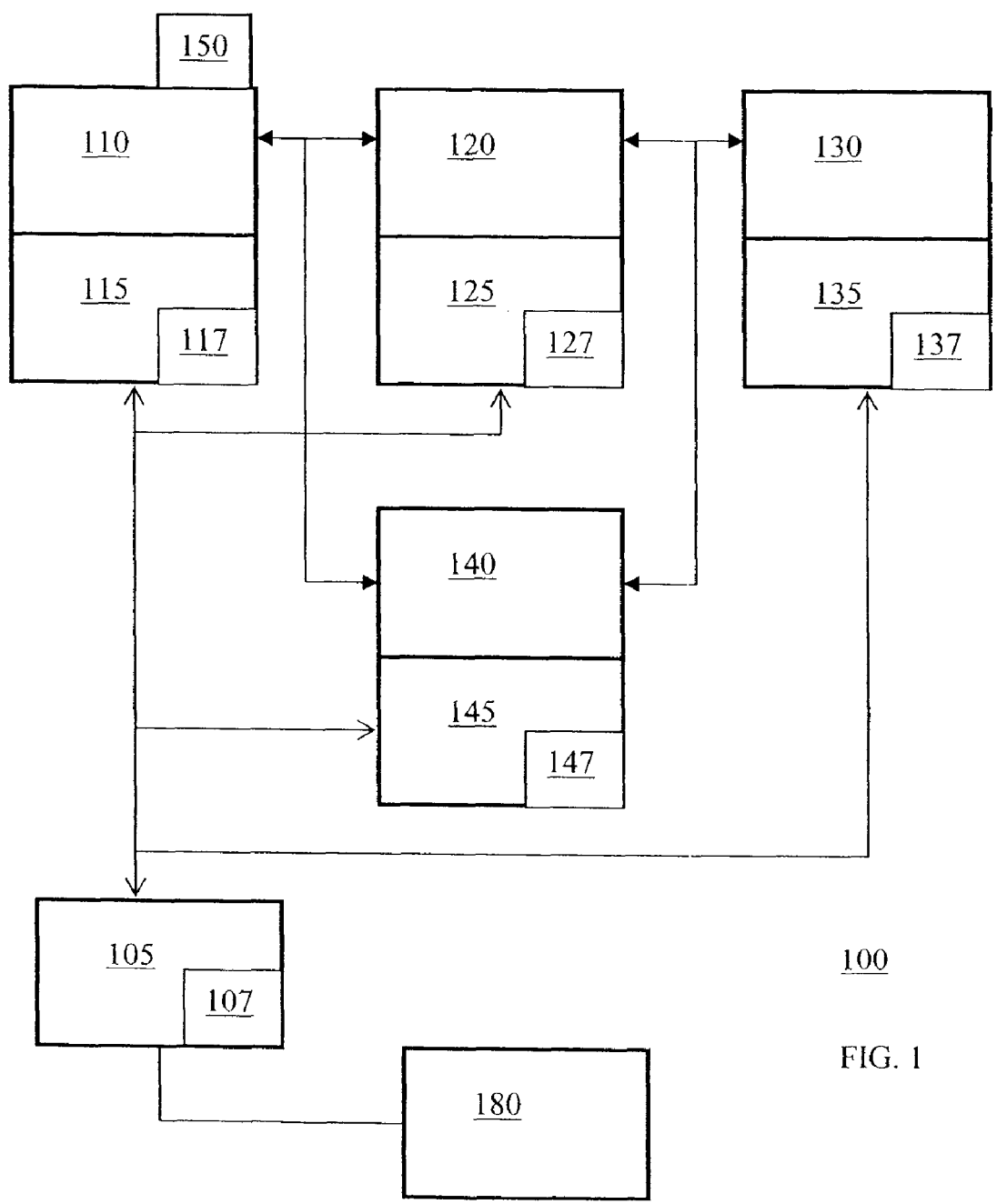
FIG. 1 shows an exemplary block diagram of a processing system in accordance with embodiments of the invention.

In material processing methodologies currently being used, pattern etching comprises the application of a thin layer of light-sensitive material, such as photoresist, to an upper surface of a wafer that can be subsequently patterned in order to provide a mask for transferring this pattern to the underlying thin film during etching. The photoresist is generally optimized for a pre-determined exposure tool having a known wavelength, and the photoresist is not optimized for a metrology tool.

Described herein are examples of optically tunable soft mask (OTSM) technology that can include tunable resist compositions that are capable of high resolution lithographic performance, especially in bilayer or multilayer lithographic applications using 243 nm or shorter wavelength imaging radiation. The OTSM can include an acid-sensitive imaging polymer, a non-polymeric silicon additive, a radiation-sensitive acid generator, and a metrology-enhancing additive.

The imaging polymer can be useful in 193 nm lithographic processes and preferably includes a monomer selected from the group consisting of a cyclic olefin, an acrylate, and a methacrylate. The resist composition preferably includes at least about 5 wt. % silicon of the imaging polymer. The non-polymeric silicon additive contains at least about 10 carbon atoms, more preferably at least about 12 to 30 carbon atoms. The non-polymeric silicon additive can have a molecular weight of about 250 to 1000.

When developing an OTSM, one goal is to achieve improved CD control and enhanced-metrology properties within a relatively wide process window. A OTSM-related process window can be affected by compatibility issues with metrology-enhancement materials, dielectric materials, wafer materials, and Bottom Anti-Reflective Coating/Anti-Reflective Coating (BARC/ARC) materials. In addition, polymer issues, exposure issues, development issues, activation issues, reflectivity issues, etch resistance issues, optical property issues, thermal issues, timing and delay issues, resolution and sensitivity issues, line edge roughness issues, and pattern collapse issues affect processing.

An optically tunable resist layer (soft mask and/or hard mask) can have first set of optical properties that can be optimized, tuned and/or enhanced for an exposure tool and/or exposure wavelengths, and the optically tunable resist layer can have a second set of optical properties that can be optimized, tuned and/or enhanced for a metrology tool and/or one or more measurement wavelengths. The optically tunable resist layer can be characterized by the first set of optical properties before exposure and can be characterized by the second set of optical properties at some point in time after exposure. The optically tunable resist layer can include light-sensitive material that can be exposed by using a radiation source and a mask/reticle. In a positive-acting resist layer, the irradiated regions of the resist layer can be removed using a developing solvent. In a negative-acting resist layer, the non-irradiated regions can be removed using a developing solvent.

Additionally, single and/or multi-layer optically tunable resist layer/masks can be established, and soft mask and/or hard mask layers can be used. The optically tunable mask can include OTSM material and/or anti-reflective material.

OTSMs can include chemically amplified components, and developing predictive models for chemically amplified OTSMs and/or resists presents a continuing challenge in the development of OTSMs. Since OTSMs can be used in many stages, the need for modeling starts at the gate level and extends to the chip level. Modeling requires knowledge of the chemical, thermal, mechanical, electrical, and optical properties of the OTSM materials, and new metrology-enhancing materials are being presented herein. Existing resist models may require modification to predict the performance of the metrology-enhancing materials. Additional complex modeling may be developed to link the lithography process with the measurement process and/or the etch process. For example, one or more lattice-type models can be used to predict and/or simulate the properties and/or behavior of the optically tunable resist layer/mask.

Also described herein are examples of an article of manufacture that can comprise a microelectronic wafer or flat panel display substrate fabricated using an optically tunable resist material.

FIG. 1 shows an exemplary block diagram of a processing system in accordance with embodiments of the invention. In the illustrated embodiment, processing system 100 comprises a lithography subsystem 110, a transfer subsystem 120, a processing subsystem 130, and a metrology subsystem 140. The lithography subsystem 110, the transfer subsystem 120, the processing subsystem 130, and the metrology subsystem 140 can be coupled to each other. The processing system 100 can include a system controller 105 and storage devices 107. The lithography subsystem 110 can include a controller 115 and storage devices 117. The transfer subsystem 120 can include a controller 125 and storage devices 127. The processing subsystem 130 can include a controller 135 and storage devices 137. The metrology subsystem 140 can include a controller 145 and storage devices 147. The controllers (105, 115, 125, 135, and 145) and storage devices (107, 117, 127, 137, and 147) can be coupled to each other as required. In addition, a scanner 150 can be coupled to the lithography subsystem 110, or alternatively, the lithography subsystem 110 may include a scanning system.

A manufacturing execution system (MES) 180 can be coupled to the system controller 105 and to one ore more of the subsystems. Alternatively other configurations may be used and other coupling techniques may be used.

One or more of the subsystems of the processing system 100 can comprise a control component, a GUI component, and/or a database component (not shown). In alternate embodiments, one or more additional subsystems may be required.

Some setup and/or configuration information can be obtained by one or more of the controllers (105, 115, 125, 135, and 145) from the factory system (MES) 180. Factory level business rules can be used to establish a control hierarchy. Business rules can be used to specify the action taken for normal processing and the actions taken on error conditions. In addition, factory level business rules can be used to determine when a process is paused and/or stopped, and what can be done when a process is paused and/or stopped. In addition, factory level business rules can be used to determine when to change a process and how to change the process.

Business rules can be defined at a strategy level, a plan level, a model level, or a procedure level. Business rules can be assigned to execute whenever a particular context is encountered. When a matching context is encountered at a higher level as well as a lower level, the business rules associated with the higher level can be executed. GUI screens can be used for defining and maintaining the business rules. Business rule definition and assignment can be allowed for users with greater than normal security level. The business rules can be maintained in the database. Documentation and help screens can be provided on how to define, assign, and maintain the business rules.

The MES 180 can be configured to monitor some system processes using data reported from by one or more of the controllers (105, 115, 125, 135, and 145). Factory level business rules can be used to determine which processes are monitored and which data can be used. For example, the controllers (105, 115, 125, 135, and 145) can independently collect data, or the data collection process can be controlled to some degree by the MES 180. In addition, factory level business rules can be used to determine how to manage the data when a process can be changed, paused, and/or stopped. In addition, the MES 180 can provide run-time configuration information to one or more of the controllers (105, 115, 125, 135, and 145). Data can be exchanged using GEM SECS communications protocol.

In general, rules allow system and/or tool operation to change based on the dynamic state of the processing system 100 and/or the processing state of a product. Some setup and/or configuration information can be determined by the processing system subsystems when they are initially configured. In addition, rules can be used to establish a control hierarchy at the system/tool level. Rules can be used to determine when a process can be paused and/or stopped, and what can be done when a process is paused and/or stopped. In addition, rules can be used to determine what corrective actions are to be performed, such as when to change a process, how to change the process, and how to manage the data.

In FIG. 1, single subsystems are shown, but this is not required for the invention. The processing system 100 can comprise a different number of processing subsystems having any number of controllers associated with them in addition to other types of processing tools and modules. Processing subsystem 130 can include an etch module, a deposition module, an ALD module, a measurement module, an ionization module, a polishing module, a coating module, a developing module, a cleaning module, or thermal treatment module or any combination of two or more thereof, including multiple instances of any of these modules.

One or more of the controllers (105, 115, 125, 135, and 145) can include GUI components (not shown) to provide easy to use interfaces that enable users to: view status; create/view/edit strategies, plans, errors, faults, databases, rules, recipes, modeling applications, simulation/spreadsheet applications, email messages; and view diagnostics screens. As should be apparent to those skilled in the art, the GUI components need not provide interfaces for all functions, and may provide interfaces for any subset of these functions or others not listed here.

One or more of the controllers (105, 115, 125, 135, and 145) and/or storage devices (107, 117, 127, 137, and 147) can include memory components (not shown) that can include one or more computer-readable storage media. In addition, one or more of the controllers (105, 115, 125, 135, and 145) and/or storage devices (107, 117, 127, 137, and 147) can exchange information with one or more computer-readable storage media. Operational data, process data, library data, historical data, and/or computer executable code can be stored in storage devices (107, 117, 127, 137, and 147) and/or controllers (105, 115, 125, 135, and 145). Data collection plans can be used to control the data that can be collected as well as when data can be collected.

In addition, before, during, and/or after data collection, an analysis strategy can be executed. In addition, judgment and/or intervention plans can be executed. When an analysis strategy is executed, wafer data, process data, module data, and/or OTSM-related data can be analyzed, and alarm/fault conditions can be identified. In addition, when judgment and/or intervention plans are associated with OTSM-related procedures, they can be executed. For example, after OTSM-related data has been created, the data can be analyzed using run-rule evaluation techniques. Accuracy limits can be calculated automatically based on historical data, on the customer's experience, or process knowledge, or obtained from a host computer. As feature sizes decrease below the 65 nm node accurate measurement data becomes more important and more difficult to obtain. Optically tunable resists can be used to accurately produce and measure these ultra-small features. The OTSM-related data can be compared with the warning and/or control limits, and when a run-rule is violated, an alarm can be generated, indicating a processing problem.

When an alarm is generated, a controller can perform either notification or intervention. Notification can be via e-mail or by an e-mail activated pager. In addition, the controller can perform an intervention: either pausing the process at the end of the current lot, or pausing the process at the end of the current wafer. The controller can identify the processing module that caused the alarm to be generated.

One or more of the controllers (105, 115, 125, 135, and 145) can include Fault Detection and Classification (FDC) applications, and they can exchange FDC information with each other and/or the MES 180. Rules can be used in Fault Detection and Classification (FDC) applications to determine how to respond to alarm conditions, error conditions, fault conditions, and/or warning conditions. In addition, the MES 180 can send command and/or override information to one or more of the controllers (105, 115, 125, 135, and 145). One or more FDC applications can be running at the same time and can send and/or receive information concerning an alarm/error/fault condition. For example, FDC information can be exchanged via an e-Diagnostics network, e-mail, or personal communication devices. For example, an alarm/error/fault condition can be established, and a message can be sent to pause the current process or to stop the current process when a limit is reached or exceeded, or when a product requirement is not met, or when a corrective action is required.

The subsystems (110, 120, 130, and 140) can control multiple processing applications and/or models that are executed at the same time and are subject to different sets of process constraints. For example, a controller can run in three different modes: simulation mode, test mode, and standard mode. A controller can operate in simulation mode in parallel with the actual process mode. In addition, FDC applications can be run in real-time and produce real-time faults and/or errors. Furthermore, FDC applications can be run in a simulation mode and produce predicted faults and/or errors.

The FDC applications can detect faults, predict system performance, predict preventative maintenance schedules, decrease maintenance downtime, and extend the service life of consumable parts in the system. The interfaces to the FDC applications can be web-enabled and can provide a real-time FDC status display.

The subsystems (110, 120, 130, and 140) and/or the processing system 100 can take various actions in response to an alarm/fault, depending on the nature of the alarm/fault. The actions taken on the alarm/fault can be context-based, and the context can be specified by a rule, a system/process recipe, a module type, module identification number, load port number, cassette number, lot number, control job ID, process job ID, slot number and/or the type of data.

The controllers (105, 115, 125, 135, and 145) can exchange information with each other and/or with the MES 180. The information can include measurement data, process data, historical data, feed-forward data, and/or feedback data. Furthermore, the MES 180 can be used to provide measurement data, such as Critical Dimension Scanning Electron Microscope (CD SEM) information. Alternately, the CD SEM information can be provided using a system controller. CD SEM information can include adjustment factors and timestamp data that can be used to adjust for any offset between the system measurement tools and external measurement tools. For example, the external measurement tools may include a CD-Scanning Electron Microscopy (CDSEM) tool, a Transmission Electron Microscopy (TEM) tool, a Focused Ion Beam (FIB) tool, an Atomic Force Microscope (AFM) tool or another optical metrology tool.

One or more control applications can be used to compute a predicted state for the wafer based on the input state, the process characteristics, and a process model. Enhanced-metrology models can be used to predict and/or calculate enhanced structures and/or features. An etch rate model can be used along with a processing time to compute an etch depth, and a deposition rate model can be used along with a processing time to compute a deposition thickness. For example, models can include Electro-Magnetic (EM) models, Statistical Process Control (SPC) charts, Partial Least Squares (PLS) models, Principal Component Analysis (PCA) models, Fault and Detection Classification (FDC) models, and Multivariate Analysis (MVA) models. A control application can operate in a simulation mode, a test mode, and a standard mode.

The processing system 100 can provide wafer sampling and the wafer slot selection can be determined using a (PJ Create) function. The R2R control configuration can include, among other variables, feed forward control plan variables, feedback control plan variables, metrology calibration parameters, control limits, and SEMI Standard variable parameters. Metrology data reports can include wafer, site, structure, and composition data, among others, and the tool can report actual settings for the wafer The metrology subsystem 140 can include an Optical Digital Profiling (ODP) system (not shown). Alternatively, other metrology systems may be used. An ODP tool is available from Timbre Technologies Inc. (a TEL company) that provides a patented technique for measuring the profile of a structure in a semiconductor device. For example, ODP techniques can be used to obtain critical dimension (CD) information, structure profile information, or via profile information, and the wavelength ranges for an ODP system can range from 200 nm to 900 nm.

The metrology subsystem 140 can use polarizing reflectometry, spectroscopic ellipsometry, reflectometry, or other optical measurement techniques to measure true device profiles, accurate critical dimensions (CD), and multiple layer film thickness of a wafer. An enhanced-metrology procedure, such as an OTSM-related procedure, can produce more vertical sidewalls than a prior art resist.

The enhanced-metrology process can be executed in-line, which eliminates the need to break the wafer for performing the analyses. ODP techniques can be used with the existing thin film metrology tools for inline profile and CD measurement, and can be integrated with Tokyo Electron Limited (TEL) processing tools and/or lithography systems to provide real-time process monitoring and control. An ODP™ solution has three key components: ODP™ Profiler™ Library comprises an application specific database of optical spectra and its corresponding semiconductor profiles, CDs, and film thicknesses. Profiler™ Application Server (PAS) comprises a computer server that connects with optical hardware and computer network. It handles the data communication, ODP library operation, measurement process, results generation, results analysis, and results output. The ODP™ Profiler™ Software includes the software installed on PAS to manage measurement recipe, ODP™ Profiler™ library, ODP™ Profiler™ data, ODP™ Profiler™ results search/match, ODP™ Profiler™ results calculation/analysis, data communication, and PAS interface to various metrology tools and computer network.

An exemplary optical metrology system is described in U.S. patent application Ser. No. 09/727,530 entitled "System and Method for Real-Time Library Generation of Grating Profiles" by Jakatdar, et al., filed on Nov. 28, 2000, and is incorporated in its entirety herein by reference.

ODP techniques can be used to measure the presence and/or thickness of coatings on wafers and/or materials within features and/or structures of a patterned wafer. These techniques are taught in U.S. patent application Ser. No. 10/357,705, entitled "Model Optimization for Structures with Additional Materials" by Niu, et al., filed on Feb. 3, 2003, and ODP techniques covering the measurement of additional materials are taught in U.S. Pat. No. 6,608,690, entitled "Optical Profilometry of Additional-material Deviations in a Periodic Grating", filed on Dec. 4, 2001, and in U.S. Pat. No. 6,839,145, entitled "Optical Profilometry of Additional-material Deviations in a Periodic Grating", filed on May 5, 2003, and all are incorporated by reference herein.

ODP techniques for creating a metrology model are taught in U.S. patent application Ser. No. 10/206,491, entitled "Model and Parameter Selection in Optical Metrology" by Voung, et al., filed on Jul. 25, 2002 and ODP techniques covering integrated metrology applications are taught in U.S. Pat. No. 6,785,638, entitled METHOD AND SYSTEM OF DYNAMIC LEARNING THROUGH A REGRESSION-BASED LIBRARY GENERATION PROCESS, filed on Aug. 6, 2001, and both are incorporated by reference herein.

Recipes can be organized in a tree structure that can comprise recipe sets, classes, and recipes that can be displayed as objects. Recipes can include process recipe data, system recipe data, and Integrated Metrology Module (IMM) recipe data. IMM recipes can contain pattern recognition information, can be used to identify the chips to sample on each wafer, and can be used to determine which PAS recipe to use. PAS recipes can be used to determine which ODP library to use, and to define the measurement metrics to report, such as top CD, bottom CD, side wall angle (SWA), layer thickness, trench width, trench depth, and goodness of fit (GOF) data.

Processing system 100 can include Advanced Process Control (APC) applications that can operate as control strategies, control plans, control models, and/or recipe managers to provide run-to-run (R2R) processing. For example, wafer level context matching at runtime allows for custom configuration by wafer (slot, waferID, lotID, etc.). In addition, feed forward and/or feedback control can be implemented by configuring control strategies, control plans, and control models. A control strategy can be executed for each system process where feed forward and/or feedback control is implemented. When a strategy is protected, all of its child objects (plans and models) cannot be edited. When a system recipe executes, one or more of the control plans within the control strategy can be executed. Each control plan can be used to modify the recipe based on feed-forward and/or feedback information.

Control and/or analysis strategies/plans can cover multiple process steps within an OTSM-related procedure, and can be used to analyze the collected data, and establish error conditions. An application can be executed when a context is matched. During the execution of an analysis application, one or more analysis plans can be executed. A plan can create an error when a data failure occurs, an execution problem occurs, or a control problem occurs. When an error occurs, the plan can generate an alarm message; the parent strategy status can be changed to a failed status; the plan status can be changed to a failed status; and one or more messages can be sent to the alarm log and the FDC system. When a feed forward plan or a feedback plan fails, one or more of the plans in the parent strategy may be terminated, and their status can be changed to a failed status. In one case, when a bad incoming wafer is detected, a control plan can detect and/or identify this as a faulty incoming wafer. In addition, when a feedback plan is enabled, the feedback plan can skip a wafer that has been identified to be defective and/or faulty by another plan. A data collection plan can reject the data at all the measurement sites for this wafer or reject the data because an OTSM-related procedure fails to meet the required accuracy limits.

In one embodiment, feedback plan failure may not terminate the strategy or other plans, and a measurement procedure failure may not terminate the strategy or other plans. Successful plans, strategies, and/or measurement procedures do not create any error/alarm messages. Pre-specified failure actions for strategy and/or plan errors can be stored in a database, and can be retrieved from the database when an error occurs. Failure actions can include use the nominal process recipe for this wafer or use a null process recipe for this wafer. A null recipe can be a control recipe that can be used by a processing tool and/or processing chamber to allow a wafer to pass through and/or remain in a processing chamber without processing. For example, a null recipe can be used when a process is paused or when a wafer does not require processing.

Process verification procedures and/or process model updates can be performed by running calibration/monitor wafers, varying the process settings and observing the results, then updating the process and/or models. For example, an update can take place every N processing hours by measuring the before and after characteristics of a calibration/monitor wafer. By changing the settings over time to check different operating regions one could validate the complete operating space over time, or run several calibration/monitor wafers at once with different recipe settings. The update procedure can take place at a tool level, at a system level, or at the factory level.

An updated enhanced recipe and/or updated enhanced model can be calculated at different times based on the wafer context and can be based on a product requirement. For example, feed-forward information, modeling information, and/or feedback information can be used to determine whether or not to change the current recipe before running the current wafer, before running the next wafer, or before running the next lot.

Also described herein is an example of a method of improving an optical metrology process. The method can comprise providing a substrate having a material layer thereon. The material layer can comprise low-k material, ultra low-k material, planarization material, dielectric material, glass material, ceramic material, or metallic material, or any combination thereof. A resist layer is deposited on the material layer. The resist layer can comprise a first set of optical properties optimized, tuned and/or enhanced for an exposure process. Alternatively, a material layer may not be required. Then, the resist layer can be exposed to patterned radiation created using a reticle and a radiation source, and the radiation source has a wavelength below approximately 300 nm. Next, a plurality of un-enhanced structures can be created in the resist layer by developing the exposed resist layer, and the plurality of un-enhanced structures can comprise at least one un-enhanced measurement structure. In addition, a plurality of enhanced structures can be created in the resist layer by enhancing the plurality of un-enhanced structures, and at least one enhanced measurement structure can be created by enhancing the at least one un-enhanced measurement structure, and the plurality of enhanced structures can be characterized by a second set of optical properties.

When a resist layer is used, the resist layer can comprise a photoresist material, or an anti-reflective material, or a combination thereof.

In addition, the plurality of enhanced structures can be created by exposing the plurality of un-enhanced structures in the resist layer to reactive gas, a liquid, plasma, radiation, or thermal energy, or a combination thereof, and the at least one enhanced measurement structure can be created by exposing the at least one un-enhanced measurement structure to a reactive gas, a liquid, plasma, radiation, or thermal energy, or a combination thereof.

Furthermore, the plurality of enhanced structures can be created by changing at least one optical property of the resist layer using a reactive gas, a liquid, plasma, radiation, or thermal energy, or a combination thereof, and at least one enhanced measurement structure can be created by changing at least one optical property of the resist layer using a reactive gas, a liquid, plasma, radiation, or thermal energy, or a combination thereof.

Alternatively, the plurality of enhanced structures may be created by removing at least one portion of the resist layer, and at least one enhanced measurement structure may be created by removing at least one portion of a resist layer.

In other embodiments, the method of improving an optical metrology process can comprise receiving a substrate. The substrate can comprise a plurality of dies and a number of measurement sites. For example, each die can have a first patterned resist layer on top of at least one other layer, and at least one measurement site can have a periodic measurement structure in it.

An accuracy value can be determined for the substrate. At least one optical property of the substrate can be modified when the accuracy value is not within limits established for an enhanced substrate, and the substrate can be processed when the accuracy value is within limits established for an enhanced substrate. At least one optical property of a first periodic measurement structure in at least one measurements site on the substrate can be modified using a reactive gas, a liquid, or plasma, or a combination thereof. For example, at least one optical property of a resist material, or an anti-reflective material, or a combination thereof can be modified. In other cases, optical properties can be changed by removing at least one portion of a resist material, or an anti-reflective material, or a combination thereof.

The method can further comprise measuring the modified substrate, and a new accuracy value can be determined for the measured substrate. For example, a measured diffraction spectrum can be obtained from the modified substrate. Alternatively, other signals and/or spectrums may be used.

Next, a best estimate structure can be selected from a library of periodic structures and associated diffraction spectrums, and a best estimate diffraction spectrum associated with the best estimate structure can be obtained, and the measured diffraction spectrum can be compared to the best estimate diffraction spectrum. Then, either an accuracy value for the substrate and measured diffraction spectrum data can be established when the measured diffraction spectrum and the best estimate diffraction spectrum match within a matching criterion, or a new best estimate structure can be selected when the measured diffraction spectrum and the best estimate diffraction spectrum do not match within a matching criterion.

For example, a new best estimate structure can be created by changing a height, a width, a thickness, a depth, a volume, an area, a dielectric property, a process recipe parameter, a processing time, a critical dimension, a spacing, a period, a position, or a line width, or a combination of two or more thereof.

In addition, the method can further comprise comparing the measured diffraction spectrum to a new best estimate diffraction spectrum associated with the new best estimate structure; establishing a new accuracy value for the substrate when the measured diffraction spectrum and the new best estimate diffraction spectrum match within a matching criterion and when the measured diffraction spectrum and the new best estimate diffraction spectrum do not match within a matching criterion, continuing to determine new best estimate diffraction spectrums until the measured diffraction spectrum and the new best estimate diffraction spectrum match within a matching criterion, or until a difference between the measured diffraction spectrum and the new calculated hypothetical diffraction spectrum match is greater than a limit value.

The new accuracy value, the new best estimate structure, and diffraction spectrum associated with the new best estimate structure can be stored when the measured diffraction spectrum and the new best estimate diffraction spectrum match within a matching criterion. For example, processing system 100 can be used for improving an optical metrology process.

Figure 2:
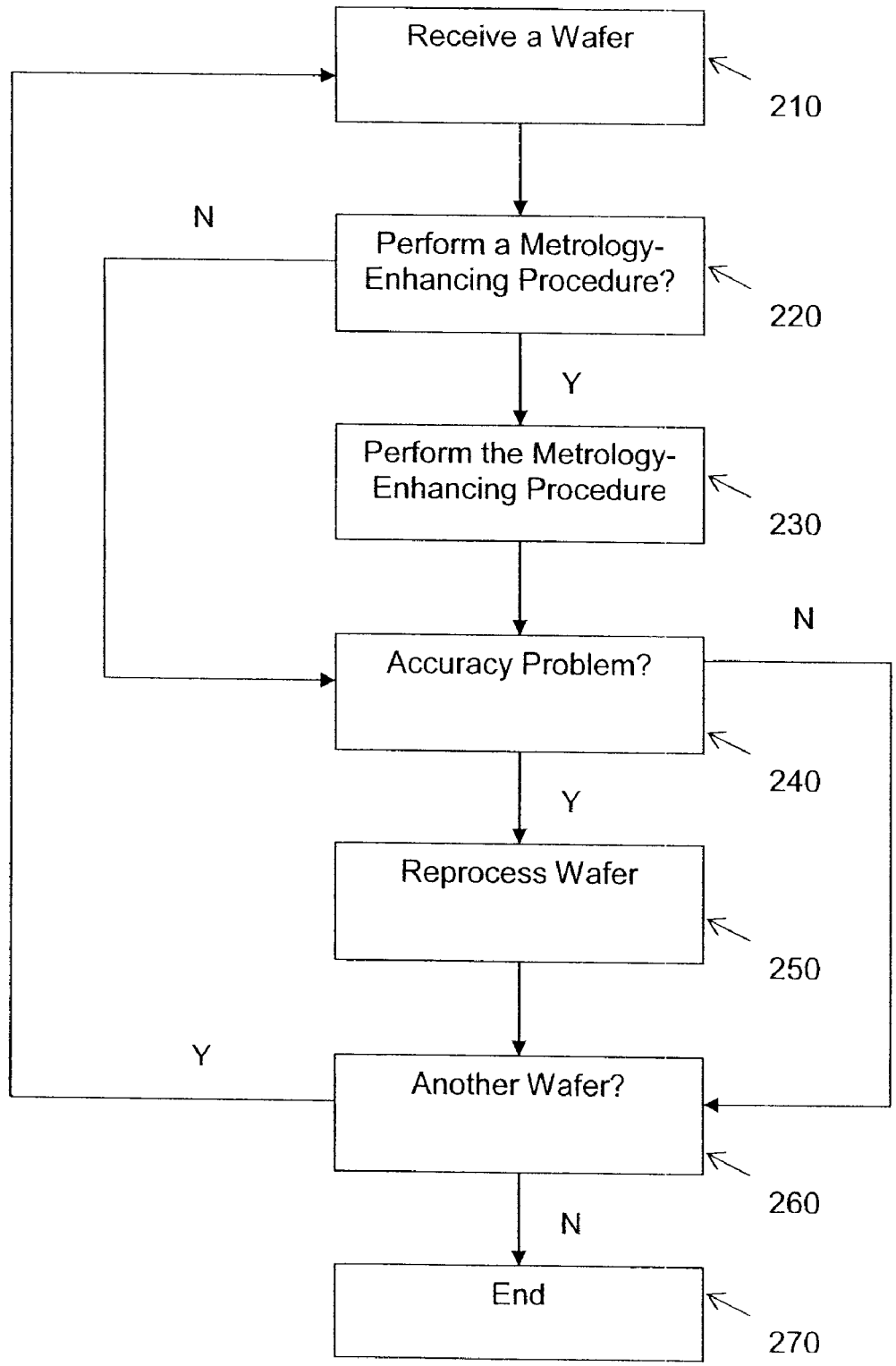
FIG. 2 illustrates an exemplary flow diagram of a method for operating a processing system in accordance with embodiments of the invention.

FIG. 2 illustrates an exemplary flow diagram of a method for operating a processing system in accordance with embodiments of the invention. In the illustrated embodiment, a procedure 200 is shown for processing a wafer using a metrology-enhancement procedure.

During a wafer processing sequence, the wafer can make numerous visits to a lithography subsystem 110 and a develop/inspect (DI) step can be performed when the wafer exits the lithography subsystem 110. During a DI step, a metrology-enhancement procedure can be performed.

In 210, a wafer can be received by a process system (100). When a wafer is received by a processing system 100 (FIG. 1), the data associated with the wafer and/or lot can be received. In one embodiment, a MES 180 system can download recipes and/or process parameters to subsystems (110, 120, 130, and 140), and the recipes and/or process parameters can be used to control a wafer processing procedure. In addition, a MES can determine wafer sequencing. For example, the MES may determine which wafers in a lot can be used during an OTSM-related and/or enhanced-metrology procedure. The downloaded data can include system recipes, process recipes, metrology recipes, OTSM-related data, and wafer sequencing plans.

Data can include wafer-related maps, such as historical maps, OTSM-related maps, library-related maps, refined (enhanced measurement) maps, reference map(s), measurement map(s), prediction map(s), and/or confidence map(s), for an in-coming wafer and/or in-coming lot. Data can include measurement data from a measurement module associated with the processing system, a host system, and/or another processing system.

Figure 3:
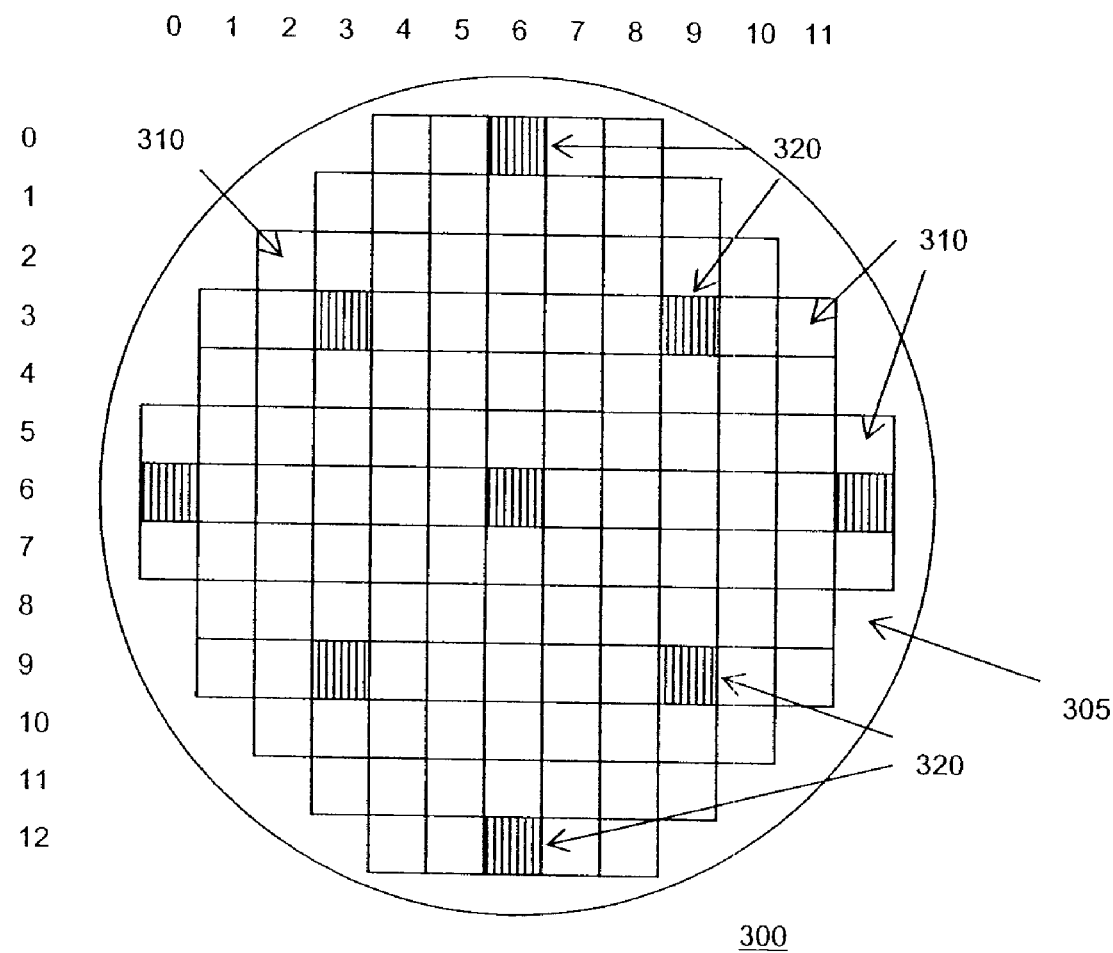
FIG. 3 shows a simplified view of a wafer map in accordance with embodiments of the invention.

FIG. 3 shows a simplified view of a wafer map in accordance with embodiments of the invention. In the illustrated embodiment, a wafer map is shown having one-hundred twenty-five chip/dies, but this is not required for the invention. Alternatively, a different number of chip/dies may be shown. In addition, the circular shapes shown are for illustration purposes and are not required for the invention. For example, the circular wafer may be replaced by a non-circular wafer, and the chip/dies may have non-circular shapes.

FIG. 3 shows a simplified view of a wafer map 305 on a wafer 300 that includes a plurality of chip/dies 310. Rows and columns are shown that are numbered from zero to twelve for illustration. In addition, potential measurement sites 320 are shown for an exemplary measurement plan. Alternatively, different shapes may be established for different wafer maps, and a different number of measurement and/or metrology-enhancement sites may be established at different locations on the wafer. When a measurement plan is created for a wafer, one or more measurement sites can be established in one or more wafer areas. For example, when the plan is created, the measurements do not have to be made at all of the measurement sites 320 shown in FIG. 3.

Referring back to FIG. 2, in task 220, a query can be performed to determine when to perform a metrology-enhancement procedure. As the physical dimensions of the structures decrease, metrology-enhancement procedures may be required for a large percentage of the wafers to obtain more accurate measurement data. In addition, some wafers may be used to verify an OTSM-related process and/or to assess OTSM-related wafers. One or more metrology-enhancement procedures can be performed using production or non-production wafers. When a new OTSM-related process is being developed and/or verified, the process results can be varying, and a metrology-enhancement procedure can be performed on a larger percentage of the wafers. When a metrology-enhancement procedure is required, procedure 200 can branch to task 230, and when a metrology-enhancement procedure is not required, procedure 200 can branch to task 240.

In task 230, a metrology-enhancement procedure can be performed. In some embodiments, optically tunable resist material or optically tunable anti-reflective coating material, or a combination thereof can be used to fabricate enhanced structures having enhanced-metrology properties. In other embodiments, a photoresist layer can be post-processed to improve the metrological properties of the photoresist layer.

In some examples, the enhanced structures can be fabricated in an OTSM layer or can be fabricated in a wafer and/or in a material layer on a wafer using an OTSM. In other examples, the enhanced structures can be fabricated in an Optically Tunable Anti-Reflective Coating (OTARC) layer or can be fabricated in a wafer and/or in a material layer on a wafer using an OTARC. In still other examples, the enhanced structures can be fabricated in an OTSM/OTARC layer or can be fabricated in a wafer and/or in a material layer on a wafer using an OTSM/OTARC.

A control strategy can be executed and used to establish a metrology-enhancement plan/recipe. When the wafer is positioned in a metrology subsystem 140, the measurements can be made in real-time. When the wafer is not currently positioned in a metrology subsystem 140, the wafer can be transferred into the metrology subsystem 140, and then the measurements can be made in real-time.

The metrology-enhancement procedure can be specified by a semiconductor manufacturer based on data stored in a historical database. For example, a semiconductor manufacturer may have historically chosen a number of positions on the wafer when making SEM measurements and would like to correlate the metrology-enhancement procedure data to the data measured using a SEM tool. Other manufacturers can use TEM and/or FIB data.

In addition, the number of measurement sites used in a metrology-enhancement procedure can be reduced as the manufacturer becomes more confident that the OTSM-related process is and will continue to produce high quality devices. Alternatively, other measurement procedures and/or other measurement sites may be used.

When new and/or additional enhanced metrology data and/or OTSM-related measurement data can be required, enhanced optical metrology measurements can be made at one or more sites on the wafer. For example, metrology-enhanced features, such as periodic gratings, periodic arrays, and/or other periodic structures, on a wafer can be measured at one or more of the measurement sites shown in FIG. 3. For example, the metrology-enhanced features on a wafer may be in an OTSM, or in a resist layer, or in an OTARC layer, or in a combination thereof. In addition, the metrology-enhanced features on a wafer may be created using an OTSM, or a resist layer, or an OTARC layer, or a combination thereof.

A metrology-enhancement procedure, such as an OTSM-related measurement procedure, can be time consuming and can affect the throughput of a processing system. During process runs, a manufacturer may wish to minimize the amount of time used to measure a wafer. The metrology-enhancement procedure can be context driven and different strategies and/or plans may be selected based on the context of the wafer. For example, one or more wafers may not be measured and/or the processes may be performed using a subset of measurement sites included in the metrology-enhancement procedure and/or plan.

During a development portion of the semiconductor process, one or more historical maps can be created and stored for later use. A historical map can include measured data at measurement sites that are different from those shown in FIG. 3. Alternatively, a historical map can use the same set of measurement sites or a historical map may not be required.

During a metrology-enhancement procedure, one or more prediction maps can be created and/or modified, and the prediction maps can include predicted measured data, predicted enhanced data, and/or predicted process data. For example, metrology-enhancement models can be used to calculate the data.

In addition, one or more prediction maps can be created and/or modified during an OTSM-related procedure, and the prediction maps can include predicted measured data, predicted OTSM-related data, and/or predicted OTSM process data. For example, predicted OTSM-related data can be obtained using an OTSM-related prediction model that can be dependent on the type of optically tunable material being used.

Furthermore, one or more confidence maps can be created and/or modified, and the confidence maps can include confidence values for the measured data, the predicted data, the modeling data, the OTSM-related measurement data, and/or the OTSM-related process data.

The wafer maps can include one or more GOF maps, one or more thickness maps, one or more via-related maps, one or more Critical Dimension (CD) maps, one or more CD profile maps, one or more material related maps, one or more trench-related maps, one or more sidewall angle maps, or one or more differential width maps, or any combination thereof. The measurement data can also include site result data, site number data, CD measurement flag data, number of measurement sites data, coordinate X data, and coordinate Y data, among others.

When OTSM-related wafer maps are created and/or modified, values may not be calculated and/or required for the entire wafer, and a wafer map may include data for one or more chip/dies, one or more different areas, and/or one or more differently shaped areas. For example, a processing chamber may have unique characteristics that may affect the accuracy of features and/or measurements in certain areas of the wafer. In addition, a manufacturer may allow less accurate metrology data for chips/dies in one or more regions of the wafer to maximize yield. A mapping application and/or the FDC system can use business rules to determine uniformity and/or accuracy limits. Business rules can be established for feature sizes associated with the 65 nm node and for features sizes associated with smaller nodes (45 nm and 32 nm).

When a value in an OTSM-related map is close to a limit, the confidence values and/or accuracy values can be weighted for different OTSMs, for different chips/dies, and/or different areas of the wafer. For example, a lower confidence weight can be assigned to the accuracy calculations and/or accuracy data associated with an OTSM during the early stages of development. In addition, process result, measurement, historical, and/or prediction maps associated with one or more OTSM-related processes may be used to calculate a confidence map for a wafer. For example, values from another map may be used as weighting factors and/or limits.

Data from OTSM-related procedures can be used to change a measurement and/or fabrication plan and to determine when to establish a new measurement site and/or new fabrication recipe. In addition, when the confidence values are low in one or more areas of the wafer, or when an error has occurred, one or more new measurement sites and/or new fabrication recipes can be established. Furthermore, when the values on a confidence map are consistently high for a particular OTSM-related process and/or when measurement values are consistently within acceptable limits for a particular OTSM-related process, a new OTSM-related measurement plan may be establish that uses a smaller number of measurement sites and that decreases the throughput time for each wafer.

In some cases, data for an entire wafer can be calculated during an OTSM-related procedure. Alternatively, data may be calculated and/or predicted for a portion of the wafer. For example, a portion may include one or more radial areas and/or quadrants. An error condition can be declared when metrology-enhancement data cannot be determined. In addition, an error condition can be declared when one or more of the measured values and/or calculated/predicted values are outside an accuracy limit established for the wafer. Some errors that are generated during a metrology-enhancement procedure can be sent to the FDC system, and the FDC system can decide how the processing system should respond to the error. Other errors can be resolved by one or more of the subsystems (110, 120, 130, and 140).

In task 240, a query can be performed to determine when the wafer has an accuracy problem. For example, an accuracy problem can occur when the metrology-enhanced data for the wafer does not meet the accuracy specification in one or more areas of the wafer. When metrology-enhanced data does not meet the accuracy specification in one or more areas of the wafer, procedure 200 can branch to task 250, and when metrology-enhanced data does meet the accuracy specification in one or more areas of the wafer, procedure 200 can branch to task 260.

In task 250, a wafer, whose metrology data does not meet the accuracy specification in one or more areas of the wafer can be re-processed. For example, when an accuracy problem is identified, during normal processing the wafer can be transferred to a first location, which may be a holding location. When an accuracy problem is not identified, then wafer processing can continue through the normal processing sequence.

When an accuracy problem is identified, one or more wafer maps can be examined. A metrology-enhancement map can be examined to determine the extent of the accuracy problem present on the wafer.

In one embodiment, when an accuracy problem is identified at one measurement site, and the data at that site suggests that the wafer has an accuracy problem, an enhanced measurement process can subsequently be repeated at additional measurement sites. When the enhanced-metrology data at one or more of the additional sites indicates an accuracy problem, then the wafer can be removed from the processing sequence, and additional analysis and/or measurements can be performed When the enhanced-metrology data at one or more of the additional assessment sites indicates that there is not an accuracy problem, then the wafer can be re-measured using the first assessment site. When the re-measured data again indicates that the wafer has an accuracy problem, the wafer can be removed from the processing sequence, and additional measurements and/or analysis can be performed. For example, an accuracy error condition may be established and/or reported, when an accuracy problem is detected.

When a new OTSM is being developed, a new OTSM fabrication recipe can be developed when an accuracy problem occurs. For example, the amount, the response time, and/or type of metrology-enhancing material can be changed.

A metrology-enhancement procedure can be used during a Dual Damascene procedure. In some embodiments, a Via First Trench Last (VFTL) procedure can be performed. In other embodiments, a Trench First Via Last (TFVL) procedure can be performed. A metrology-enhancement process can be performed before a first damascene process, a second damascene process, or both damascene processes. Alternatively, a metrology-enhancement process may not be required during a Dual Damascene procedure. For example, an OTSM and/or an OTARC may be used during VFTL and/or TFVL procedures.

A metrology-enhancement procedure can be used to create a trench structure, a via structure, a dual damascene structure, an isolated structure, or a nested structure, or a combination thereof.

In task 260, a query can be performed to determine when another wafer requires processing. When another wafer requires processing, procedure 200 can branch to task 210, and when another wafer does not require processing, procedure 200 can branch to task 270. Procedure 200 can end in 270.

In various embodiments, wafer state information can be determined before, during, or after a metrology-enhancement procedure is performed. Since a wafer can undergo many lithography steps during processing, the current (incoming) state for the wafer can vary, and the metrology-enhancement procedure can vary. The wafer can includes a plurality of layers, and the wafer size can vary from 200 mm to 450 mm. Alternatively, substrates for flat panel devices may be larger.

One or more of the controllers (105, 115, 125, 135, and 145) can determine wafer state information and this information can be shared. The wafer state information may include additional measurement data. For example, during wafer processing some wafers may be sent to an external metrology unit, which may be an external metrology tool, a CD SEM system, a TEM system, and/or a FIB system (all not shown).

The processing system 100 can be used to process wafers having isolated and nested features and control strategies can be used to define the process sequence. During an isolated/nested measurement sequence, the processing subsystem 130 and/or the lithography subsystem 110 can select one IMM recipe to use, and separate IMM recipes can be used for isolated and nested structures. Each wafer can be measured separately for each pitch and structure. When an OTSM is used, an enhanced measurement can be made, and enhanced measurement data can be obtained. An enhanced library can then be searched using enhanced measurement data (enhanced measured spectrum), and one or more isolated or nested structures can be identified. The enhanced measurement sequence can be performed for one or more different locations. For example, a measurement grating/structure having a first pitch may be provided that is consistent with the isolated structures/features for a particular product and technology and another measurement grating/structure having a second pitch may be provided that is consistent with the nested structures/features for this product and technology.

The processing system 100 can establish wafer sampling and the wafer slot selection can be determined using a (PJ Create) function. The R2R control configuration can include, among other variables, feed forward control plan variables, feedback control plan variables, metrology calibration parameters, control limits, or SEMI Standard variable parameters. Metrology data can include wafer, site, structure, or composition data, among others, and the data can include actual settings for the wafer.

The metrology subsystem 140 can use polarizing reflectometry, spectroscopic ellipsometry, reflectometry, or other optical instruments to measure true device profiles, accurate critical dimensions (CD), or multiple layer film thickness of a wafer. The metrology subsystem 140 can include ODP technology, and the ODP™ technology can include: ODP™ Profiler™ Library that comprises an application specific database of optical spectra and its corresponding semiconductor profiles, CDs, and film thicknesses; a Profiler™ Application Server (PAS) that comprises a computer server that connects with optical hardware and computer network and handles the data communication, ODP library operation, measurement process, results generation, results analysis, and results output; or the ODP™ Profiler™ Software that includes the software installed on PAS to manage measurement recipe, ODP™ Profiler™ library, ODP™ Profiler™ data, ODP™ Profiler™ results search/match, ODP™ Profiler™ results calculation/analysis, data communication, and PAS interface to various metrology tools and computer network.

An APC system can comprise management applications, such as a recipe management application, and the recipe management application can be used to view and/or control OTSM-related recipes stored in the database. A client workstation can be placed separately at a distance from the factory, and can provide comprehensive management functions to multiple equipment units.

Referring again to FIG. 1, metrology subsystem 140 can be configured to examine enhanced and/or un-enhanced periodic structures, such as gratings, patterned lines, patterned vias, and/or patterned arrays, to obtain enhanced and/or un-enhanced measurement data. For example, zero-order cross polarization measurement data may be obtained, and wafer measurement data may be obtained based on the zero-order cross polarization measurement data. Alternatively, other orders may be used.

Enhanced features and/or structures can be determined using enhanced and/or un-enhanced periodic measurement structures formed on a wafer. For example, as the features and/or structures of the devices/circuits are formed on the wafer through one or more fabrication processes, the features of periodic measurement structures are also formed on wafer. In addition, the features and/or structures of the devices/circuits formed on the wafer during one or more fabrication processes can be used as enhanced and/or un-enhanced periodic measurement structures.

In addition, one or more periodic measurement structures can be formed in test areas on wafer that are proximate to or within devices/circuits formed on wafer. For example, periodic measurement structures can be formed adjacent a device/circuit formed on wafer. Alternatively, periodic measurement structures can be formed in an area of the device/circuit that does not interfere with the operation of the device/circuit or along scribe lines on wafer. Thus, the optical measurements obtained for periodic measurement structures can be used to determine whether the devices/circuits adjacent periodic measurement structures have been fabricated according to specifications.

In some embodiments, the metrology subsystem 140 can perform signal and/or structure analysis in real-time using ODP regression techniques, and the analysis data can be used for the generation of enhanced and/or un-enhanced profile libraries. For example, regression optimization procedures can be performed on a set of measurements to obtain a set of resultant parameter values that can be associated with a profile of an enhanced structure and/or feature. In addition, the metrology subsystem 140 can include a storage device for storing enhanced and/or un-enhanced data.

Metrological subsystem 140 can include one or more optical metrology devices (not shown). Examples of optical metrology devices include spectroscopic ellipsometers, spectroscopic reflectometers, variable angle, single wavelength reflectometers and ellipsometers, or polarization reflectometers or ellipsometers. When metrology subsystem 140 includes an ellipsometer, the amplitude ratio tan $\Psi$ and the phase $\Delta$ of a diffraction signal can be received and detected. When metrology subsystem 140 includes a reflectometer, the relative intensity of a diffraction signal can be received and detected. Additionally, when metrology subsystem 140 includes a polarization reflectometer, the phase information of a diffraction signal can be received and detected.

Metrology subsystem 140 can receive a measured diffraction signal and analyze the measured diffraction signal, and the periodic measurement structures can be determined using various linear or non-linear profile extraction techniques, such as a library-based process, a regression-based process, and the like. For a more detailed description of a library-based process, see U.S. patent application Ser. No. 09/907,488, titled GENERATION OF A LIBRARY OF PERIODIC GRATING DIFFRACTION SIGNALS, filed on Jul. 16, 2001, which is incorporated herein by reference in its entirety. For a more detailed description of a regression-based process, see U.S. patent application Ser. No. 09/923,578, titled METHOD AND SYSTEM OF DYNAMIC LEARNING THROUGH A REGRESSION-BASED LIBRARY GENERATION PROCESS, filed on Aug. 6, 2001, which is incorporated herein by reference in its entirety. For a more detailed description of a machine learning system, see U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

In addition, optical measurement systems and techniques are taught in U.S. Pat. No. 6,947,141, entitled OVERLAY MEASUREMENTS USING ZERO-ORDER CROSS POLARIZARIZATION MEASUREMENTS, filed on Sep. 8, 2004, U.S. Pat. No. 6,928,395, entitled METHOD AND SYSTEM FOR DYNAMIC LEARNING THROUGH A REGRESSION-BASED LIBRARY GENERATION PROCESS, filed on May 27, 2004, and U.S. Pat. No. 6,839,145, entitled OPTICAL PROFILOMETRY OF ADDITIONAL-MATERIAL DEVIATIONS IN A PERIODIC GRATING, filed on May 5, 2003 and all of which are assigned to Timbre Technologies, Inc a TEL company and all are incorporated by reference herein.

Metrology subsystem 140 can be used to perform OTSM-related procedures using a periodic measurement structure. The metrology subsystem 140 can be used to determine the profile of an un-enhanced and/or enhanced measurement structure, such as a periodic grating and/or array, formed on wafer before, during, and/or after an OTSM-related procedure. The measurement structure can be established as and/or using an OTSM and can be formed in test areas on wafer, such as adjacent to a device formed on wafer. Alternatively, a measurement structure may be formed in an area of the device that does not interfere with the operation of the device or along scribe lines on wafer.

The metrology subsystem 140 can include one or more radiation sources (not shown) and one or more radiation detectors (not shown). An un-enhanced and/or enhanced periodic measurement structure can be illuminated by an incident beam and one or more diffracted beams can be received and converted into a measured diffraction signal (measured spectral data). Alternatively, other measurement techniques may be used.

The metrology subsystem 140 can analyze a measured diffraction signal and determine the profile of the un-enhanced and/or enhanced measurement structure using a library-based process or a regression-based process. Alternatively, other signals may be used. Additionally, other linear or non-linear profile extraction techniques are contemplated.

Figure 4A:
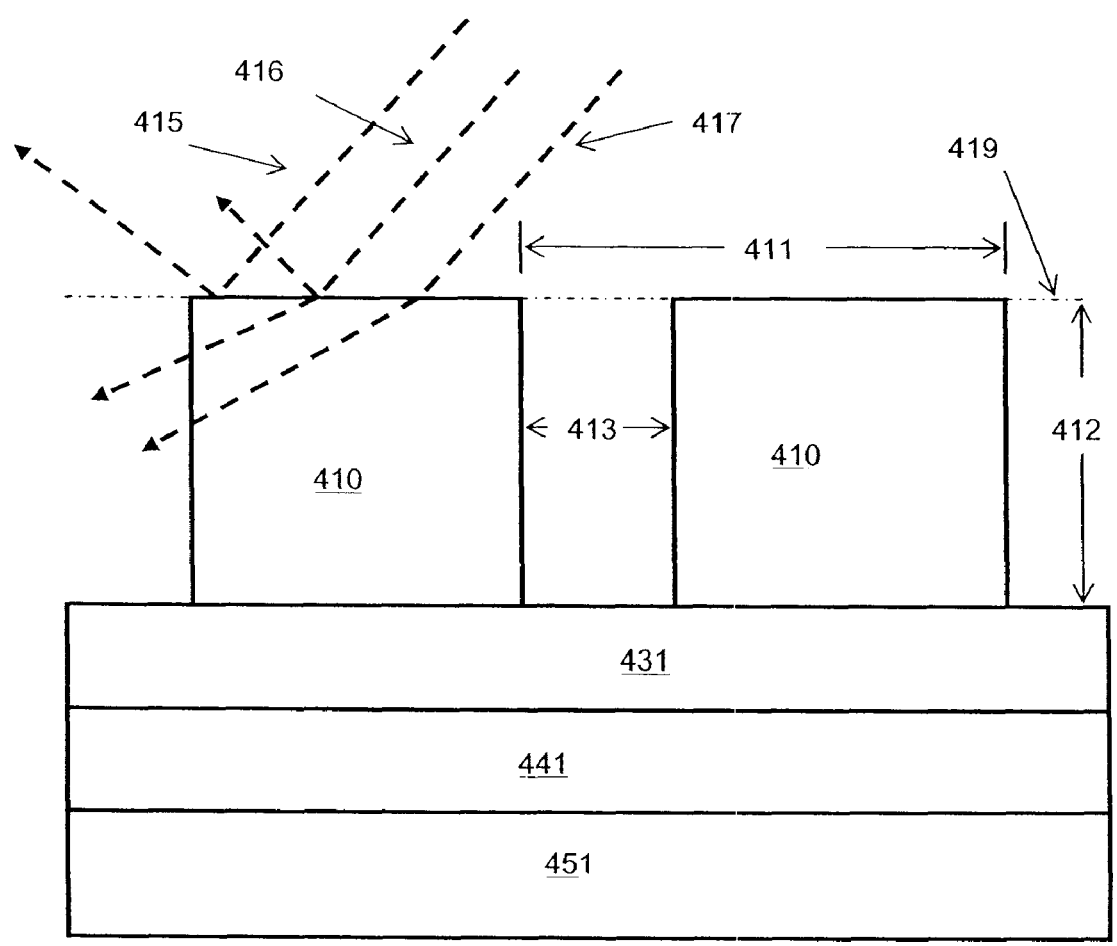
FIG. 4A illustrates exemplary pre-processed OTSM structures in accordance with embodiments of the invention.

FIG. 4A illustrates exemplary pre-processed OTSM structures in accordance with embodiments of the invention. In the illustrated embodiment, exemplary pre-processed OTSM structures 410 are shown, as they could exist in an unprocessed layer 419 before a metrology-enhancing procedure has been performed. In FIG. 4A, pre-processed OTSM structures 410 (e.g. structures that have not been processed using a metrology-enhancing procedure) are shown along with exemplary light rays 415, 416, and 417. In this example, a first light ray 415 is shown being totally reflected by an exemplary pre-processed OTSM structure 410 that is shown in a preprocessed layer 419. For example, some (pre-processed) OTSM materials may be substantially opaque at one or more wavelengths before a metrology-enhancing procedure is performed on them. In addition, a second light ray 416 is shown being partially reflected by an exemplary pre-processed OTSM structure 410. For example, some (pre-processed) OTSM materials could be partially transparent at one or more wavelengths before a metrology-enhancing procedure is performed on them. Furthermore, a third light ray 417 is shown passing through an exemplary pre-processed OTSM structure 410. For example, some (pre-processed) OTSM materials could be substantially transparent at one or more wavelengths at or near the exposure wavelength before a metrology-enhancing procedure is performed on them.

A separation distance 411 is shown for the pre-processed OTSM structures 410, a structure height 412 is shown, and a space 413 is shown between the pre-processed OTSM structures 410. For example, optically tunable resist material in space 413 may be removed during a metrology-enhancing procedure. The separation distance 411 may be periodic.

The pre-processed OTSM structures 410 can be in an undeveloped layer 419 on a plurality of layers that can include a bottom (backside) anti-reflective coating (BARC) layer 431, a material layer 441, and a wafer layer 451. Alternatively, a different stack configuration and/or different materials may be used. In addition, the wafer layer 451 may include other semiconductor materials such as silicon, strained silicon, silicon-germanium, or germanium, dielectric materials, ceramic materials, glass materials, and/or metallic materials.

The inventors have noted that in some cases there is very little difference in the measured spectrum before exposure and the measured spectrum after exposure. The inventors contemplate many embodiments for improving the measured spectrum after exposure.

Figure 4B:
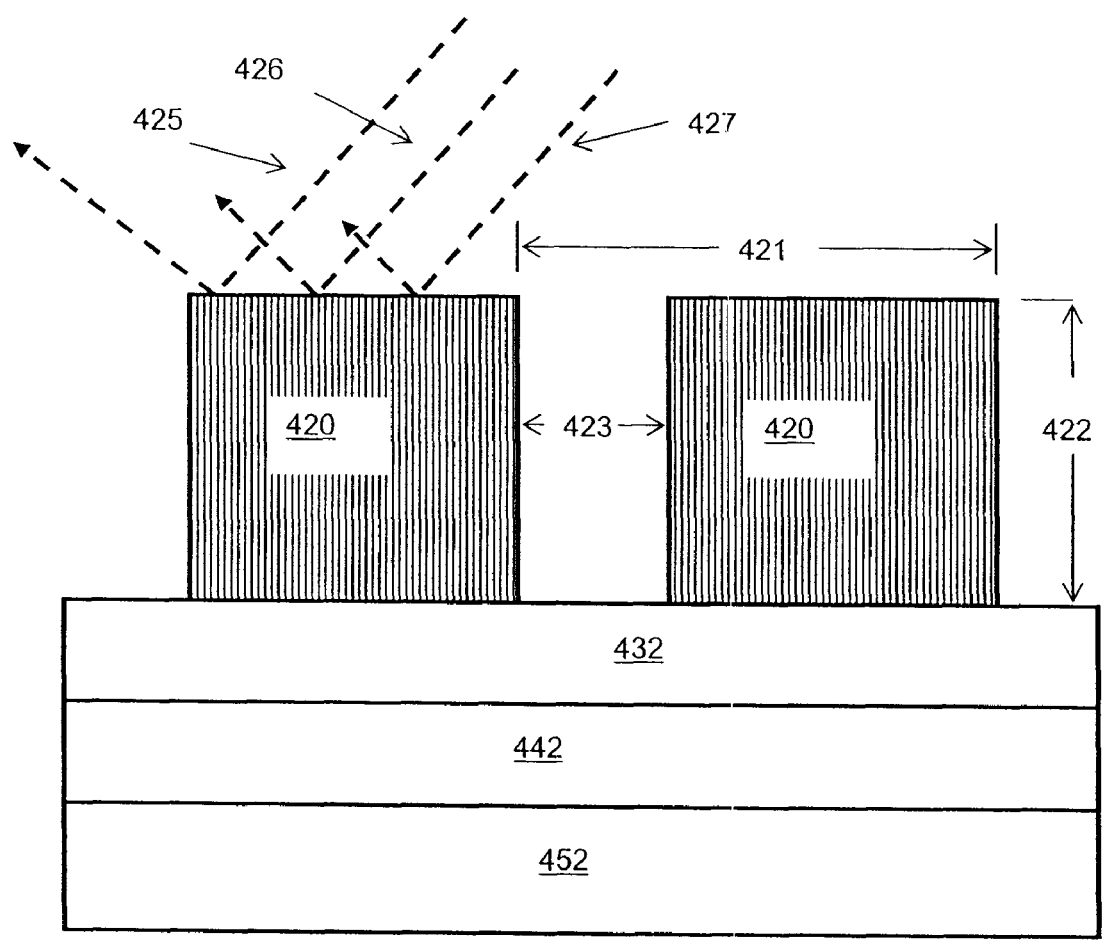
FIG. 4B illustrates exemplary post-processed OTSM structures in accordance with embodiments of the invention.

FIG. 4B illustrates exemplary post-processed OTSM structures in accordance with embodiments of the invention. In the illustrated embodiment, exemplary post-processed OTSM structures 420 are shown after a metrology-enhancing procedure has been performed. In FIG. 4B, OTSM structures 420 that have been processed using a metrology-enhancing procedure are shown along with exemplary light rays 425, 426, and 427. In the illustrated embodiment, the exemplary light rays 425, 426, and 427 are shown being totally reflected by the post-processed OTSM structures 420. For example, some optically tunable resist materials may be substantially opaque at substantially all of the measurement wavelengths after a metrology-enhancing procedure has been performed. In alternate embodiments, one or more of exemplary light rays 425, 426, or 427 may be partially reflected by the OTSM structures 420. For example, some OTSM materials may be partially transparent at one or more wavelengths after a metrology-enhancing procedure has been performed. In additional embodiments, one or more of exemplary light rays 425, 426, or 427 may pass through the OTSM structures 420. For example, some OTSM materials can be designed to be substantially transparent at one or more wavelengths after a metrology-enhancing procedure has been performed.

A separation distance 421 is shown for the OTSM structures 420, a structure height 422 is shown, and an opening 423 is shown between the OTSM structures 420. The separation distance 421 may be periodic.

The post-processed OTSM structures 420 can be on a plurality of layers that can include a bottom (backside) anti-reflective coating (BARC) layer 432, a material layer 442, and a wafer layer 452. Alternatively, a different stack configuration and/or different materials may be used. In addition, the wafer layer 451 may include other semiconductor materials such as silicon, strained silicon, silicon-germanium, or germanium, dielectric materials, ceramic materials, glass materials, and/or metallic materials.

In some embodiments, an additive can be incorporated into an OTSM material such as a resist material, ARC material and/or BARC material. The additive can be a chemical group added to the resist layer material to enhance the optical properties of the OTSM in one or more wavelength ranges. In addition, some additives can be activated during the development process, and other additives can be activated after the development process. For example, some additives can be activated during an acid generation step, and other additives can be activated after the acid generation step.

In some embodiments, one or more processing chambers associated with the processing system 100 can be used to enhance the optical properties of a resist layer. For example, the wafer can be positioned within a processing chamber and treated using a reactive gas, a liquid, plasma, radiation, or thermal energy, or a combination thereof to make the photoresist less transparent to radiation at or near an exposure wavelength.

Figure 5:
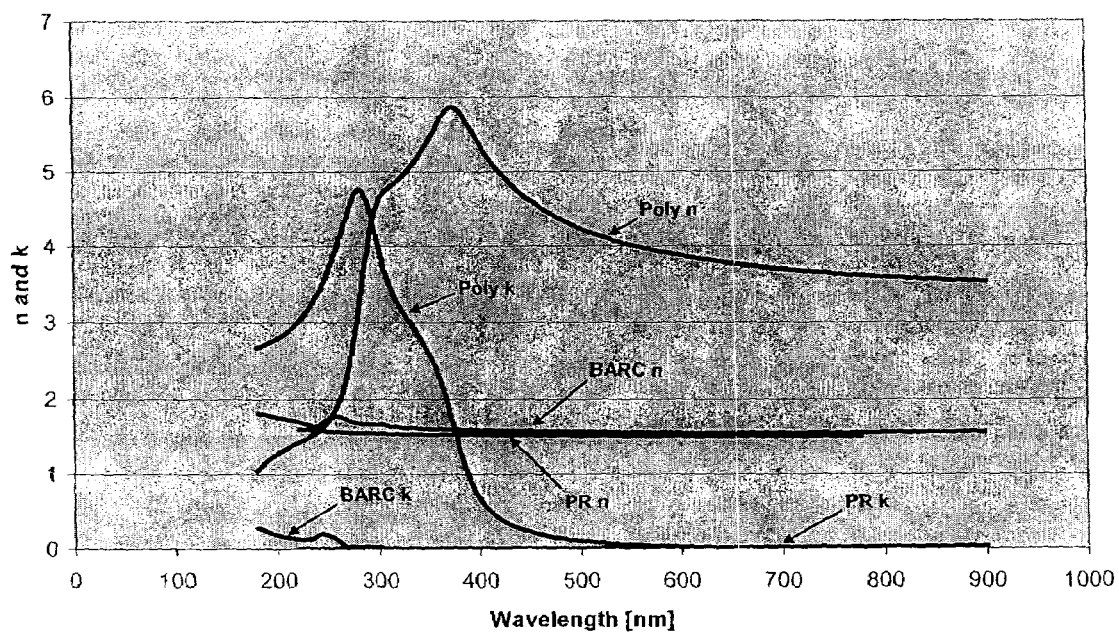
FIG. 5 illustrates an exemplary graph of material properties in accordance with embodiments of the invention.

FIG. 5 illustrates an exemplary graph of material properties in accordance with embodiments of the invention. FIG. 5 illustrates the index of refraction (n) and extinction coefficient (k) values versus wavelength for photoresist (PR), BARC, polysilicon. As shown in FIG. 5, the PR and BARC have very similar optical characteristics while the polysilicon has very different optical characteristics, especially in the UV region (<210 nm). Alternatively, the data may be different for the illustrated materials.

When examining the reflective properties of a silicon wafer, one or more minima can occur between approximately 200 nm and approximately 1000 nm.

The OTSM material can be applied to the surface of the wafer in a uniform layer, exposed and developed, leaving patterned areas that protect the underlying areas from subsequent processing. In the same way, patterned areas can be established on the wafer to be used as optical metrology targets. BARC layers may be used to enhance the control of critical dimensions (CD) by suppressing standing wave effects and reflective notching caused by thin film interference. In one example, the BARC layer can be used to absorb ultra-violet (UV) light used during the lithographic exposure in order to decrease perturbations due to reflected light. The reflected spectrum from the BARC layer has very little light in the UV region.

One of the main objectives of a semiconductor processing facility is to consistently produce high quality devices while using a number of different processing tools and/or measurement tools. As critical dimensions decrease, tool and/or chamber matching issues have become increasingly important. As additional metrology tools are introduced into the processing sequence, the ability to obtain high quality measurements is also becoming more important. Metrology tools must be characterized and consistent performance must be verified when multiple metrology tools are introduced into a semiconductor processing facility.

Lithography subsystem 110 may be used to deposit OTSM material onto a wafer. A scanner 150 can be coupled to lithography subsystem 110 and can be used to expose the OTSM. The scanner 150 can use immersion lithography techniques. The lithography subsystem 110 may also perform baking processes and/or developing processes. For example, post application bake (PAB) and/or post exposure bake (PEB) processes may be performed on the OTSM during a metrology-enhancement procedure. In some embodiments, the PAB time can vary from approximately 10 seconds to approximately 15 minutes, and may be dependant on the glass transition temperature of an OTSM material.

The PEB process may be used to drive the acid-catalyzed reaction and to activate and/or drive the catalyzation of the metrology-enhancing materials of the OTSM. The PEB temperature can be between approximately 60 degrees Celsius and approximately 375 degrees Celsius, and the PEB time can vary from approximately 30 seconds to approximately 5 minutes. In addition, a drying step may be performed to remove any remaining developer solvent.

When an enhanced structure in an OTSM is being measured, an enhanced profile library can be used and/or created. In addition, when enhanced features and/or enhanced structures produced using an OTSM are being measured, an enhanced profile library can be used and/or created. The enhanced profile library can include enhanced signals and/or enhanced profile/shapes can have more accurate (enhanced) parameters associated with them. For example, the enhanced profile library can include wider bandwidth signals and the profile/shapes can have more accurate lengths, widths, and/or heights associated with them.

In an enhanced (improved accuracy) library, the simulated diffraction signals can include additional data points at additional wavelengths. For example, additional data points may be available at the smaller wavelengths that are near and/or at the exposure wavelength. When the enhanced features are measured and/or simulated, a wider bandwidth signal can be used to provide a more accurate profile/shape. In addition, the enhanced (improved accuracy) library can include smaller features associated with the 32 nm technology node. For example, when measuring enhanced and/or ultra-small features, such as OTSM-related features, the measurement error can be less than five percent.

In some embodiments, a Library-Based process can be used for determining the profile of a periodic measurement structure in an OTSM-related procedure. In a library-based process, the measured diffraction signal can be compared to a library of simulated diffraction signals for un-enhanced and/or enhanced periodic structures. A simulated diffraction signal in the library can be associated with a hypothetical profile of an un-enhanced and/or enhanced periodic measurement structure. When a match is made between the measured diffraction signal from the OTSM and one of the simulated diffraction signals in the enhanced library or when the difference of the measured diffraction signal and one of the simulated diffraction signals is within a preset or matching criterion, the hypothetical profile associated with the matching simulated diffraction signal is presumed to represent the actual profile of the measured structure in the OTSM. The matching simulated diffraction signal and/or hypothetical profile can then be utilized to determine more accurately whether the OTSM has been fabricated according to specifications. When a match is not made between the measured diffraction signal from the OTSM and one of the simulated diffraction signals in the enhanced library or when the difference of the measured diffraction signal and one of the simulated diffraction signals is not within a preset or matching criterion, new hypothetical enhanced profiles and associated simulated diffraction signals can be created and used to find a match.

In addition, when a match is not made, a fault condition can be reported, indicating that the OTSM and/or a structure created using the OTSM have not been fabricated according to specifications. When an evaluation (measurement) procedure is performed at or before the Develop Inspection (DI) step, fabrication errors can be detected earlier in the process sequence, and fewer faulty wafers are produced. In addition, faulty wafers can be re-worked since the OTSM can easily be removed and re-deposited.

Single layer and multi-layer hypothetical profiles can be created for use with OTSM-related materials and processes. In addition, hypothetical profiles can be created for damaged and/or un-damaged structures and/or features.

In other embodiments, a regression-based process can be used for determining the profile of an enhanced and/or un-enhanced measurement structure. In a regression-based process, the measured diffraction signal can be compared to a simulated diffraction signal (i.e., a trial diffraction signal). The simulated diffraction signal can be generated prior to the comparison using a set of parameters (i.e., trial parameters) for a hypothetical profile. If the measured diffraction signal and the simulated diffraction signal do not match or when the difference of the measured diffraction signal and one of the simulated diffraction signals is not within a preset or matching criterion, another simulated diffraction signal is generated using another set of parameters for another hypothetical profile, then the measured diffraction signal and the newly generated simulated diffraction signal are compared. When the measured diffraction signal and the simulated diffraction signal match or when the difference of the measured diffraction signal and one of the simulated diffraction signals is within a preset or matching criterion, the hypothetical profile associated with the matching simulated diffraction signal is presumed to represent the actual profile of a periodic measurement structure. The matching simulated diffraction signal and/or hypothetical profile can then be utilized to determine whether the structure has been fabricated according to specifications.

New and/or additional enhanced hypothetical profiles can be generated by characterizing an enhanced hypothetical profile using a set of parameters, then varying the set of parameters to generate hypothetical profiles of varying shapes and dimensions along with the associated signals. The process of characterizing a profile using a set of parameters can be referred to as parameterizing. In addition, additional enhanced hypothetical profiles can be generated by characterizing a hypothetical signal using a set of parameters, then varying the set of parameters over a wider range of wavelengths to generate additional hypothetical signals and profiles.

In some embodiments, measurement data obtained from an optical metrology tool can include polarization data. The polarization data can be transformed into P-domain data, and the P-domain data can be used in some OTSM-related procedures. For example, P-domain signatures may be used to identify OTSM-related structures/profiles and/or enhanced profiles.

In other embodiments, enhanced measurement data can be obtained from an enhanced optical metrology tool and can include enhanced polarization data. The enhanced polarization data can be transformed into enhanced P-domain data, and the enhanced P-domain data can be used in some OTSM-related procedures. For example, enhanced P-domain signatures may be used to identify OTSM-related structures/profiles and/or enhanced profiles. For example, enhanced P-domain data can include data having a wider (enhanced) bandwidth.

An OTSM can include a first set of optical properties that can be optimized, tuned and/or enhanced for an exposure process and a second set of optical properties optimized, tuned and/or enhanced for a measurement process. In addition, OTSM can include a first set of optical properties that can be optimized, tuned and/or enhanced for an exposure tool and a second set of optical properties optimized, tuned and/or enhanced for a measurement tool.

Figure 6:
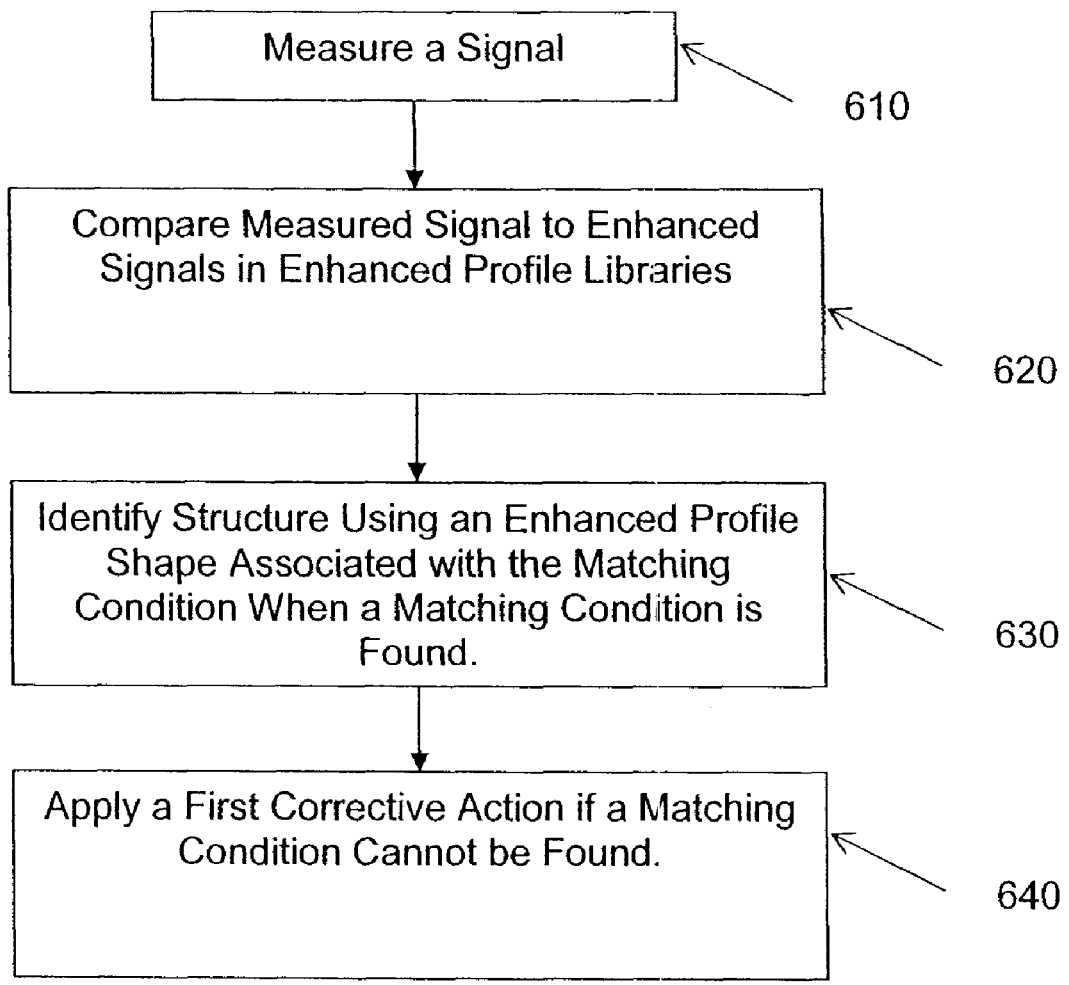
FIG. 6 illustrates an exemplary flow diagram of a procedure for using an enhanced profile library that was created using an OTSM layer in accordance with embodiments of the invention.

FIG. 6 illustrates an exemplary flow diagram of a procedure for using an enhanced profile library that was created using an OTSM layer. In the illustrated embodiment, a procedure 600 for determining an enhanced profile of a structure using a measured signal is shown. In 610, a signal can be measured off a structure in an OTSM layer with a metrology device, and the measurement can generate a measured signal. In addition, a signal can be measured off a structure that was created using an OTSM layer or another optically tunable layer.

In 620, the measured signal can be compared to a plurality of enhanced signals in one or more enhanced profile libraries. An enhanced signal in the enhanced profile library can be characterized by an enhanced set of wavelengths. In addition, an enhanced profile library can contain more accurate data and/or data for smaller features associated with the 65 nm node and below.

In 630, the structure can be identified using an enhanced profile shape associated with the matching condition when a matching condition is found. In 640, a first corrective action can be applied if a matching condition cannot be found. One or more tasks associated with or in procedure 600 can be performed in real-time to maximize throughput. Enhanced profile libraries can be used, refined, and/or created dynamically, and OTSM-related procedures can be performed in real-time.

The process of applying a first corrective action can comprise determining a first enhanced profile data space, and the first enhanced profile data space can be determined using the measured signal, enhanced profile library data, process data, historical data, or a combination thereof. Next, a best estimate signal can be determined within the first enhanced profile data space, and an enhanced profile shape and/or enhanced profile parameters can be associated with the best estimate signal. Then, a first difference can be calculated between the measured signal and the best estimate signal, and the first difference can be compared to a first enhanced profile library creation criteria. Subsequently, the structure can either be identified using the enhanced profile shape associated with the best estimate signal if the first enhanced profile library creation criteria is met, or a second corrective action can be applied if the first enhanced profile library creation criteria is not met.

In addition, the best estimate signal and the enhanced profile shape associated with the best estimate signal can be stored in the enhanced profile library if the first enhanced profile library creation criteria is met.

The process of applying a second corrective action can comprise selecting a new best estimate signal from within the first enhanced profile data space, and determining a new enhanced profile shape and/or new enhanced profile parameters based on the new best estimate signal. In some processes, an optimization technique can be performed to select the new best estimate signal. Next, a new difference can be calculated between the measured signal and the new best estimate signal, and the new difference can be compared to a new enhanced profile library creation criteria. Subsequently, the structure can be identified either using the new enhanced profile shape associated with the new best estimate signal if the new enhanced profile library creation criteria is met, or stopping the selecting, the calculating, and the comparing, if the new enhanced profile library creation criteria is not met. When an optimization technique is used, a global optimization technique and/or a local optimization technique can be applied.

In addition, the new best estimate signal and the new enhanced profile shape associated with the new best estimate signal can be stored in the enhanced profile library if the new enhanced profile library creation criteria is met.

In one example, the enhanced profile library can comprise a plurality of enhanced structures created in an OTSM layer by activating metrology-enhancing material in the OTSM layer.

In addition, the enhanced profile library can comprise a plurality of enhanced structures created in a material layer on a wafer using an OTSM layer, the OTSM layer including enhanced features created by activating metrology-enhancing material in the OTSM layer.

The matching condition can include GOF data, material data, wavelength data, threshold data, process data, or historical data, or a combination thereof.

The procedure can further comprise determining an accuracy value for the measured signal; comparing the accuracy value against accuracy limits; and performing an enhanced measurement procedure if the accuracy value does not meet the accuracy limits. For example, an enhanced measurement procedure can be performed using an enhanced measurement tool that can make measurements near and/or at exposure wavelengths.

The procedure may also include determining an accuracy value for the best estimate signal, for the enhanced profile data space, for the enhanced profile shape, or for the enhanced profile parameters, or for a combination thereof; comparing the accuracy value against accuracy limits; and performing a refinement procedure if the accuracy value does not meet the accuracy limits. Alternatively, a new OTSM and/or new OTSM-related procedure may be performed.

In other embodiments, the process of applying a first corrective action can comprise performing the enhanced measurement procedure, and an enhanced signal can be obtained off the structure using an enhanced metrology device, the enhanced measurement procedure generating an enhanced measured signal having increased amplitude at one or more wavelengths below 400 nm; comparing the enhanced measured signal to a plurality of signals in the enhanced profile library; and either identifying the structure using an enhanced profile shape associated with the enhanced measured signal when a matching condition is found or applying a second corrective action if a matching condition cannot be found.

In other embodiments, the process of applying a second corrective action can comprise determining a first enhanced profile data space, and the first enhanced profile data space being determined using the enhanced measured signal, enhanced profile library data, process data, historical data, or a combination thereof; determining a first best estimate signal within the first enhanced profile data space, and a first enhanced profile shape and/or first enhanced profile parameters are determined based on the first best estimate signal; and calculating a first difference between the enhanced measured signal and the first best estimate signal; comparing the first difference to a first enhanced profile library creation criteria; and either identifying the structure using the first enhanced profile shape associated with the first best estimate signal if the first enhanced profile library creation criteria is met, or applying a third corrective action if the first enhanced profile library creation criteria is not met. In addition, the first best estimate signal and the first enhanced profile shape associated with the first best estimate signal can be stored in the enhanced profile library if the first enhanced profile library creation criteria is met.

Furthermore, the process of applying a third corrective action can comprise selecting a new best estimate signal from within the first enhanced profile data space, and a new enhanced profile shape and/or new enhanced profile parameters can be determined based on the new best estimate signal, and an optimization technique can be performed to select the new best estimate signal; calculating a new difference between the enhanced measured signal and the new best estimate signal; comparing the new difference to a new enhanced profile library creation criteria; and either identifying the structure using the new enhanced profile shape associated with the new best estimate signal if the new enhanced profile library creation criteria is met, or stopping the selecting, the calculating, and the comparing, if the new enhanced profile library creation criteria is not met. In addition, the new best estimate signal and the new enhanced profile shape associated with the new best estimate signal can be stored in the enhanced profile library if the new enhanced profile library creation criteria is met.

In other embodiments, the process of applying a first corrective action can comprise: determining a measured profile shape to associate with the measured signal; comparing the measured profile shape to a plurality of profile shapes in the enhanced profile library, a profile shape in the enhanced profile library being characterized by an enhanced set of wavelengths, and either identifying the structure using the measured profile shape when a matching condition is found or applying a second corrective action if a matching condition cannot be found.

Furthermore, applying a second corrective action can comprise: determining a first enhanced profile data space, and the first enhanced profile data space being determined using the measured profile shape, the measured signal, enhanced profile library data, process data, historical data, or a combination thereof; determining a best estimate profile shape within the first enhanced profile data space, and an enhanced profile signal and/or enhanced profile parameters are associated with the best estimate profile shape; calculating a first difference between the measured profile shape and the best estimate profile shape; comparing the first difference to a first enhanced profile library creation criteria; and either identifying the structure using the best estimate profile shape if the first enhanced profile library creation criteria is met, or applying a third corrective action if the first enhanced profile library creation criteria is not met. In addition, the enhanced profile shape and data associated with the best estimate profile shape can be stored in the enhanced profile library if the first enhanced profile library creation criteria is met.

In other embodiments, the process of applying a third corrective action can comprise selecting a new best estimate profile shape from within the first enhanced profile data space, and a new enhanced profile signal and/or new enhanced profile parameters are determined based on the new best estimate profile shape, and an optimization technique can be performed to select the new best estimate profile shape; calculating a new difference between the measured profile shape and the new best estimate profile shape; comparing the new difference to a new enhanced profile library creation criteria; and either identifying the mask structure using the new best estimate profile shape if the new enhanced profile library creation criteria is met, or stopping the selecting, the calculating, and the comparing, if the new enhanced profile library creation criteria is not met. In addition, the new best estimate profile shape and data associated with the new best estimate profile shape can be stored in the enhanced profile library if the new enhanced profile library creation criteria is met.

In various embodiments, the enhanced profile library creation criteria can include GOF data, OTSM-related data, wavelength data, threshold data, process data, historical data, or a combination thereof. In addition, the enhanced library creation criteria can include size data, accuracy data, resolution data, process data, material data, fabrication data, and/or structure data.

The differences can be determined using one or more wavelengths in a range of wavelengths from approximately 100 nm to approximately 1000 nm. In some embodiments, a best estimate signal and/or best estimate profile can be determined in real-time using differences between clusters associated with the enhanced profile library. In other embodiments, a best estimate signal and/or best estimate profile can be determined in real-time using a polyhedron in an enhanced profile data space.

For example, a polyhedron can be created or selected in the enhanced profile data space. Alternatively, polyhedrons may be established in non-enhanced profile libraries. A polyhedron can be determined using a best estimate or best match data point and can have corners corresponding to selected profile parameter data points in the enhanced profile data space that are proximate to the best estimate or best match data point. In addition, a total cost function associated with the polyhedron can be minimized, and the total cost function can include a cost function of the signals corresponding to the selected profile parameter data points relative to the reference signal and a cost function of the best estimate signal relative to the reference signal. When the minimization is successful, the created enhanced profile data can be stored. The polyhedron can have at least one corner associated with each enhanced profile parameter. The total cost function can be minimized by selecting a set of weighting vectors; each weighting vector can have vector elements, and each vector element can be associated with the enhanced profile signal corresponding to a selected data point. Next, a total cost function can be calculated for each weighting vector of the set of weighting vectors, and the weighting vector that yields the minimum total cost function can be selected. Then, the enhanced profile data can be created or refined using the weighting vector associated with the minimum total cost function.

When creating and/or refining an enhanced profile library an adjustment matrix can be calculated. An adjustment matrix can include an adjustment value for at least one enhanced profile signal, and each adjustment value can be determined using a diffraction signal associated with a profile of the un-enhanced profile library, or a diffraction signal associated with a profile of the enhanced profile library, or a combination thereof. A new enhanced profile signal can be created by using the adjustment matrix and the diffraction signals associated with the un-enhanced profile library, the diffraction signals associated with the enhanced profile library, or diffraction signals associated with a data point outside the libraries.

When a refinement procedure is used, the refinement procedure can utilize bilinear refinement, Lagrange refinement, Cubic Spline refinement, Aitken refinement, weighted average refinement, multi-quadratic refinement, bi-cubic refinement, Turran refinement, wavelet refinement, Bessel's refinement, Everett refinement, finite-difference refinement, Gauss refinement, Hermite refinement, Newton's divided difference refinement, osculating refinement, or Thiele's refinement algorithm, or a combination thereof.

In some cases, best estimate signals can be determined by minimizing a total cost function, and the total cost function can include a cost function of the signals corresponding to the selected profile parameter data points relative to the enhanced reference/measured signal and a cost function of the best estimate signal relative to the enhanced/measured reference signal.

In some embodiments, applying a second corrective action can comprise: determining a new enhanced profile data space, and the new enhanced profile data space being determined using the first enhanced profile data space, the measured signal, enhanced profile library data, process data, historical data, or a combination thereof; determining a second best estimate signal within the new enhanced profile data space, and a new enhanced profile shape and/or new enhanced profile parameters are associated with the second best estimate signal; calculating a second difference between the measured signal and the second best estimate signal; comparing the second difference to a second enhanced profile library creation criteria; and either identifying the structure using the enhanced profile shape associated with the second best estimate signal if the second enhanced profile library creation criteria is met, or applying a third corrective action if the second enhanced profile library creation criteria is not met. In addition, the second best estimate signal and the enhanced profile shape associated with the second best estimate signal can be stored in the enhanced profile library if the second enhanced profile library creation criteria is met.

Furthermore, applying a third corrective action can comprise selecting a new best estimate signal from within the new enhanced profile data space, and a new enhanced profile shape and/or new enhanced profile parameters are determined based on the new best estimate signal, and an optimization technique can be performed to select the new best estimate signal calculating a new difference between the measured signal and the new best estimate signal; comparing the new difference to a new enhanced profile library creation criteria; and either identifying the structure using the new enhanced profile shape associated with the new best estimate signal if the new enhanced profile library creation criteria is met, or stopping the selecting, the calculating, and the comparing, if the new enhanced profile library creation criteria is not met. In addition, the new best estimate signal and the new enhanced profile shape associated with the new best estimate signal can be stored in the enhanced profile library if the new enhanced profile library creation criteria is met.

In other methods for determining an enhanced profile of a structure, a measured signal can be compared to a plurality of signals in an OTSM profile library, and an OTSM profile library can comprise a plurality of enhanced structures created in an OTSM, or a plurality of enhanced structures created using an OTSM, or a combination thereof. An enhanced signal in the OTSM profile library can be characterized by an enhanced set of wavelengths determined using the optical properties of one or more OTSMs associated with the OTSM profile library, and different optical properties can be established by activating metrology-enhancing materials in one or more OTSMs.

In still other methods for determining an enhanced profile of a structure, a structure in an OTSM layer can be measured using a metrology device, and the measurement can generate a best estimate profile shape. A simulation can be performed and a simulated enhanced signal can be generated. The simulated enhanced signal can be generated off an enhanced structure characterized by the enhanced profile shape corresponding to the best estimate profile shape. Next, the simulated enhanced signal can be compared to a plurality of signals in an optically tunable soft mask (OTSM) profile library, and the OTSM profile library can comprise a plurality of enhanced structures created in an OTSM, or a plurality of enhanced structures created using an OTSM, or a combination thereof. An enhanced signal in the OTSM profile library can be characterized by an enhanced set of wavelengths determined using the optical properties of one or more OTSMs associated with the OTSM profile library, and different optical properties can be established by activating metrology-enhancing materials in one or more OTSMs. Then, the structure can either be identified using the measured profile shape associated with the matching condition when a matching condition is found, or a corrective action can be applied if a matching condition cannot be found.

Figure 7:
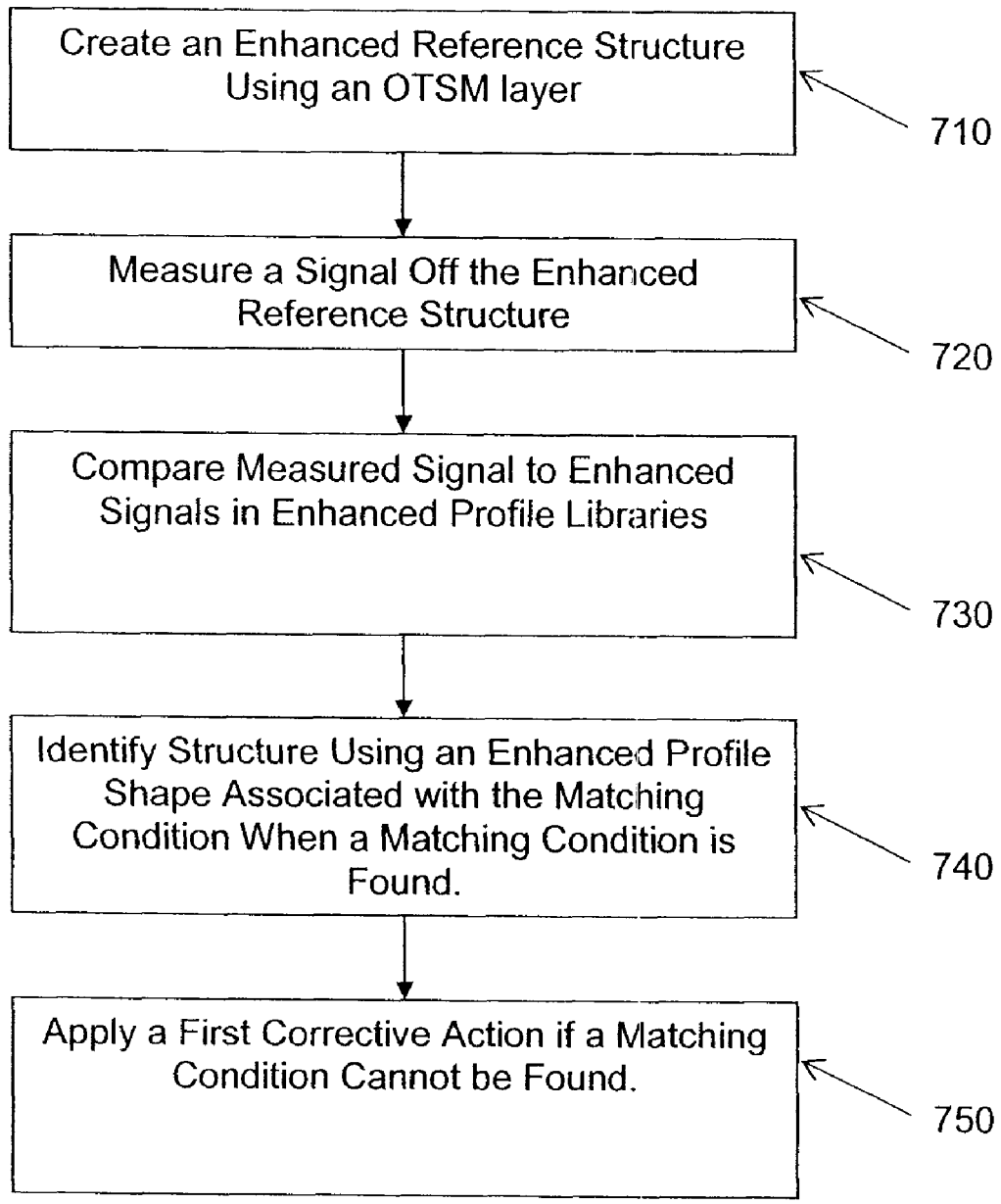
FIG. 7 illustrates an exemplary flow diagram of a procedure for creating an enhanced profile library in accordance with embodiments of the invention.

FIG. 7 illustrates an exemplary flow diagram of a procedure for creating an enhanced profile library in accordance with embodiments of the invention. In the illustrated embodiment, a procedure 700 is shown for creating an enhanced profile library using an OTSM layer. In 710, an enhanced reference structure can be created in an OTSM or in another optically tunable layer on a wafer. In other embodiments, an enhanced reference structure can be created in one or more material layers using an OTSM as a mask.

The wafer can comprise semiconductor material, dielectric material, glass material, ceramic material, or metallic material, or a combination thereof, and the material layer can comprise semiconductor material, dielectric material, glass material, ceramic material, or metallic material, or a combination thereof.

In 720, the enhanced reference structure can be measured using a metrology device, and the measurement can generate enhanced reference data that can comprise an enhanced reference signal, or an enhanced reference profile shape, or enhanced reference profile parameters, or a combination thereof.

In 730, a query can be performed to determine if a matching condition can be found. The enhanced reference signal, or the enhanced reference profile shape, or the enhanced reference profile parameters, or a combination thereof can be compared to data in an enhanced profile library, and the data in the enhanced profile library being characterized by an enhanced set of wavelengths.

In 740, the enhanced reference structure can be identified using the enhanced profile library data associated with the matching condition when a matching condition is found. In 750, a first corrective action can be applied if a matching condition cannot be found.

In some examples, applying a first corrective action can include a number of steps including determining a first best data point in a first enhanced profile data space within the data space associated with the enhanced profile library, and an enhanced profile signal, or an enhanced profile shape, or enhanced profile parameters, or a combination thereof are associated with the first best data point; calculating a first difference between the enhanced reference data and the data associated with the first best data point; comparing the first difference to a first enhanced profile library creation criteria; and either identifying the enhanced reference structure using the enhanced profile library data associated with the first best data point and storing the enhanced profile library data associated with the first best data point if the first enhanced profile library creation criteria is met, or applying a second corrective action if the first enhanced profile library creation criteria is not met.

In some examples, applying a second corrective action can comprise determining a second best data point in the first enhanced profile data space within the data space associated with the enhanced profile library, and a second enhanced profile signal, or a second enhanced profile shape, or second enhanced profile parameters, or a combination thereof are associated with the second best data point; calculating a second difference between the enhanced reference data and the data associated with the second best data point; comparing the second difference to a second enhanced profile library creation criteria; and either identifying the enhanced reference structure using the enhanced profile library data associated with the second best data point and storing the enhanced profile library data associated with the second best data point if the second enhanced profile library creation criteria is met, or applying a third corrective action if the second enhanced profile library creation criteria is not met.

In some examples, applying a third corrective action can comprise selecting a new best data point in a new enhanced profile data space within the data space associated with the enhanced profile library, and a new enhanced profile signal, or a new enhanced profile shape, or new enhanced profile parameters, or a combination thereof are associated with the new best data point; calculating a new difference between the enhanced reference data and the data associated with the new best data point; comparing the new difference to a new enhanced profile library creation criteria; and either identifying the enhanced reference structure using the enhanced profile library data associated with the new best data point and storing the enhanced profile library data associated with the new best data point if the new enhanced profile library creation criteria is met, or stopping the selecting, the calculating, and the comparing if the new enhanced profile library creation criteria is not met.

In other examples, applying a third corrective action can comprise selecting a new best data point in a new enhanced profile data space proximate to the data space associated with the enhanced profile library, and a new enhanced profile signal, or a new enhanced profile shape, or new enhanced profile parameters, or a combination thereof are associated with the new best data point; calculating a new difference between the enhanced reference data and the data associated with the new best data point; comparing the new difference to a new enhanced profile library creation criteria; and either identifying the enhanced reference structure using the enhanced profile library data associated with the new best data point and storing the enhanced profile library data associated with the new best data point if the new enhanced profile library creation criteria is met, or stopping the selecting, the calculating, and the comparing if the new enhanced profile library creation criteria is not met.

For example, a best data point can be selected by applying a global optimization technique, or a local optimization technique, or a combination thereof. Enhanced profile data spaces can be determined using the enhanced reference signal, the enhanced reference profile shape, the enhanced profile library data, process data associated with the creation of the enhanced reference structure, historical data, or OTSM-related data, or a combination thereof.

In addition, the enhanced profile library can comprise a plurality of enhanced structures created in an OTSM layer and a plurality of enhanced structures created in a material layer on a wafer using an OTSM layer as a mask. The OTSM layer can include enhanced features having enhanced optical properties created by activating metrology-enhancing material in the OTSM layer. The matching condition can include accuracy data, GOF data, OTSM data, wavelength data, threshold data, process data, historical data, or a combination thereof.

In some examples, the enhanced reference structure can be created by depositing a layer of optically tunable material on the wafer, and the layer of optically tunable material can include optical properties that are tunable in a first wavelength range proximate an optical source wavelength and that are tunable in a second wavelength range above the optical source wavelength. The layer of optically tunable material can be patterned by exposing the layer of optically tunable material to patterned electromagnetic radiation at the optical source wavelength. For example, the layer of optically tunable material can have a first set of optical properties during at least a portion of the exposure process. Then, the patterned layer of optically tunable material can be developed. The exposed optically tunable material can be removed during developing thereby creating at least one enhanced reference structure, and the optical properties of the layer of optically tunable material can be changed to a second set of optical properties during developing thereby creating enhanced metrological properties for the at least one enhanced reference structure. Alternatively, one set of optical properties can be established for the exposure process, another set of optical properties can be established after the exposure process, and one or more additional sets of optical properties can be established during and/or after the developing process.

For example, the optical source wavelength can be approximately 248 nm, or approximately 193 nm, or approximately 157 nm, or approximately 126 nm, or below approximately 126 nm, or a combination thereof.

The following relationship can be used to relate the incident and reflected light:

$$E_r = \left(\frac{n_1 - n_2}{n_1 + n_2}\right) E_i,$$

where $n_1$ and $n_2$ are the index of refraction of the first and second medium, and $E_r$ and $E_i$ are the electric fields for the reflected and incident light. The coefficient of reflection R can be defined as the ratio of the intensities of the reflected and incident waves:

$$R = \frac{I_r}{I_i} = \left(\frac{E_r}{E_i}\right)^2$$

In addition, the amount of light absorbed by a material can determined using an extinction coefficient k and an exponential decay relationship (Beer's Law) shown below:

$$I = I_0 e^{-\alpha z}$$

-continued $$\alpha = \frac{4\pi k}{\lambda}$$

where I is the light intensity, $I_0$ is the initial light intensity, z is the propagation depth, $\alpha$ is the absorption coefficient, $\lambda$ is the wavelength, and k is the extinction coefficient.

In some examples the first set of optical properties can be established using a resist layer component having a tunable index of refraction ($n_T$), and the tunable index of refraction ($n_T$) can be established between about 1.2 and about 2.8 in a first range around 248 nm and established between about 1.0 and about 3.8 in a second range above 248 nm, or can be established between about 1.2 and about 2.8 in a first range around 193 nm and established between about 1.0 and about 3.8 in a second range above 193 nm, or can be established between about 1.2 and about 2.8 in a first range around 157 nm and established between about 1.0 and about 3.8 in a second range above 157 nm, or can be established between about 1.2 and about 2.8 in a first range around 126 nm and established between about 1.0 and about 3.8 in a second range above 126 nm, or in can be established between about 1.2 and about 2.8 in a first extreme ultraviolet range below 126 nm and established between about 1.0 and about 3.8 in a second range above the first extreme ultraviolet range, or a combination of two or more thereof.

In addition, the second set of optical properties can be established using a resist layer component having a tunable index of refraction ($n_T$), and the tunable index of refraction ($n_T$) can be established between about 1.2 and about 2.8 in a first range around 248 nm and established between about 1.0 and about 3.8 in a second range above 248 nm, or can be established between about 1.2 and about 2.8 in a first range around 193 nm and established between about 1.0 and about 3.8 in a second range above 193 nm, or can be established between about 1.2 and about 2.8 in a first range around 157 nm and established between about 1.0 and about 3.8 in a second range above 157 nm, or can be established between about 1.2 and about 2.8 in a first range around 126 nm and established between about 1.0 and about 3.8 in a second range above 126 nm, or in can be established between about 1.2 and about 2.8 in a first extreme ultraviolet range below 126 nm and established between about 1.0 and about 3.8 in a second range above the first extreme ultraviolet range, or a combination of two or more thereof.

In other examples the first set of optical properties can be established using a resist layer component having a tunable reflection coefficient ($k_T$), and the tunable reflection coefficient ($k_T$) can be established between about 0.2 and about 0.8 in a first range around 248 nm and can be established between about 0.5 and about 3.0 in a second range above 248 nm, or can be established between about 0.2 and about 0.8 in a first range around 193 nm and established between about 0.5 and about 3.0 in a second range above 193 nm, or can be established between about 0.2 and about 0.8 in a first range around 157 nm and established between about 0.5 and about 3.0 in a second range above 157 nm, or can be established between about 0.2 and about 0.8 in a first range around 126 nm and established between about 0.5 and about 3.0 in a second range above 126 nm, or in can be established between about 0.2 and about 0.8 in a first extreme ultraviolet range below 126 nm and established between about 0.5 and about 3.0 in a second range above the first extreme ultraviolet range, or a combination of two or more thereof.

In addition, the second set of optical properties can be established using a resist layer component having a tunable reflection coefficient ($k_T$), and the tunable reflection coefficient ($k_T$) can be established between about 0.2 and about 0.8 in a first range around 248 nm and established between about 0.5 and about 3.0 in a second range above 248 nm, or can be established between about 0.2 and about 0.8 in a first range around 193 nm and established between about 0.5 and about 3.0 in a second range above 193 nm, or can be established between about 0.2 and about 0.8 in a first range around 157 nm and established between about 0.5 and about 3.0 in a second range above 157 nm, or can be established between about 0.2 and about 0.8 in a first range around 126 nm and established between about 0.5 and about 3.0 in a second range above 126 nm, or in can be established between about 0.2 and about 0.8 in a first extreme ultraviolet range below 126 nm and established between about 0.5 and about 3.0 in a second range above the first extreme ultraviolet range, or a combination of two or more thereof.

In still other examples, one set of optical properties can be determined by an optically tunable resist material, or a optically tunable bottom anti-reflective coating (BARC) material, or a combination thereof, and the another set of optical properties can be determined by a modified optically tunable resist material, or a modified optically tunable BARC material, or a combination thereof. The modified optically tunable resist material can be established using a coating process, an etching process, a thermal process, a cleaning process, an oxidation process, a nitridation process, or a development process, or a combination thereof, and the modified optically tunable BARC material can be established using a coating process, an etching process, a thermal process, a cleaning process, an oxidation process, a nitridation process, or a development process, or a combination thereof.

In some examples, the enhanced reference structure can be created by depositing a layer of optically tunable material on the wafer. The layer of optically tunable material can comprise a set of optical properties that can be tunable in a first wavelength range proximate an optical source wavelength and another set of optical properties that can be tunable in a second wavelength range above the optical source wavelength. The layer of optically tunable material can be patterned by exposing the layer of optically tunable material to patterned electromagnetic radiation at the optical source wavelength. The layer of optically tunable material can have a first set of optical properties for exposure. Next, the patterned layer of optically tunable material can be developed, and the exposed optically tunable material can be removed during developing thereby creating at least one enhanced reference structure. Then, the optical properties of the layer of optically tunable material can be changed to the second set of optical properties during a post-developing process thereby creating enhanced metrological properties for the at least one enhanced reference structure. For example, the post-developing process can comprise a coating process, an etching process, a deposition process, a thermal process, a polishing process, a cleaning process, an oxidation process, a nitridation process, or an ionization process, or a combination thereof.

The optical properties data can include intensity data, transmission data, received data, refraction data, absorption data, reflectance data, reflectance data, or diffraction data, or a combination thereof.

The enhanced structure data can be measured and/or verified using CD-scanning electron microscope (CD-SEM)

data, transmission electron microscope (TEM) data, atomic force microscopy (AFM) data, and/or focused ion beam (FIB) data.

The enhanced profile library creation criteria can include OTSM data, GOF data, creation rules data, process data, historical data, threshold data, or accuracy data, or a combination thereof.

In addition, when creating an enhanced profile library real-time processes can be used. For example, the creating process, or the measuring process, or the comparing process, or the identifying process, or the storing process, or a combination thereof can be performed in real-time. Alternatively, one or more enhanced profile library creation processes may be performed off-line using one or more computers/servers. The first difference, or the new difference, or a combination thereof can be determined at a plurality of wavelengths between approximately 100 nm and approximately 1000 nm.

In some fabrication processes, an anti-reflective layer can be deposited on the wafer before depositing the OTSM. The anti-reflective layer can comprise tunable optical properties, or non-tunable optical properties. The tunable optical properties may be tunable at one or more wavelengths in a range from approximately 100 nm to approximately 1000 nm. In some examples, the anti-reflective layer can have an extinction coefficient of at least 1.5 at an exposure wavelength, and a refractive index greater than 1.2 at an exposure wavelength. For example, the anti-reflective layer can comprise silicon oxynitride, or silicon oxide, or a combination thereof.

In other examples, an enhanced structure can be created by depositing a layer of optically tunable material on a material layer on the wafer. The layer of optically tunable material can comprise optical properties that can be tunable in a first wavelength range proximate an optical source wavelength and one or more other sets of optical properties that can be tunable in a second wavelength range above the optical source wavelength. Alternatively, the tuning range for the one or more other sets of optical properties may include a wavelength range proximate an optical source wavelength.

The layer of optically tunable material can be exposed to patterned electromagnetic radiation at the optical source wavelength, and the layer of optically tunable material can be characterized by a first set of optical properties during the exposure process. Alternatively, the optical properties of the layer of optically tunable material may change during the exposure process and/or be changed by the exposure process. The exposed layer of optically tunable material can be developed, and the exposed optically tunable material can be removed during developing thereby creating a plurality of structures in the layer of optically tunable material. Alternatively, the un-exposed optically tunable material can be removed during developing thereby creating a plurality of structures in the layer of optically tunable material.

In addition, a first set of enhanced structures can be created in the layer of optically tunable material by enhancing the plurality of structures in the layer of optically tunable material. The metrology-enhancing material can be activated during the developing process thereby enhancing the optical properties of the first set of enhanced structures in the layer of optically tunable material by changing the optical properties of the layer of optically tunable material to a metrology-enhancing set of optical properties.

Then, a second set of enhanced structures can be created in the material layer using a first set of enhanced structures in the layer of optically tunable material as a soft mask during an etching process, and the remaining optically tunable material can be removed. Alternatively, the remaining optically tunable material may not be removed.

In other embodiments, an enhanced profile library can be created by directing an enhanced incident beam on a first enhanced structure in an Optically Tunable Soft Mask (OTSM) layer, and the first enhanced structure can be formed by modifying at least one optical property of the OTSM layer after developing the OTSM layer. An enhanced metrology tool can be used to direct the enhanced incident beam, and the enhanced metrology tool can generate enhanced measurement data that can comprise an enhanced profile signal, or an enhanced profile shape, or enhanced profile parameters, or a combination thereof. The enhanced metrology tool can generate data having a wider bandwidth, and can generate data proximate to the wavelength used by the exposure tool (<200 nm). For example, some un-enhanced tools cannot produce quality data at wavelengths below 400 nm.

A first enhanced simulated signal can be calculated, and the first enhanced simulated signal corresponds to a hypothetical profile of the first enhanced structure. The hypothetical profile can include a portion of the modified OTSM therein. A simulation can be performed using the hypothetical profile. In addition, a first difference between the enhanced profile signal and the first enhanced simulated signal can be calculated, and the enhanced profile signal and the first enhanced simulated signal can be characterized by an enhanced set of wavelengths.

Next, the first difference can be compared to a first enhanced profile library creation criteria; and either the first enhanced structure can be identified using the hypothetical profile and the first enhanced simulated signal, the hypothetical profile of the first enhanced structure, including data for the modified OTSM portion can be stored in the enhanced library if the first enhanced profile library creation criteria is met or a first corrective action can be applied if the first enhanced profile library creation criteria is not met.

In some examples, applying the first corrective action can comprise defining a new hypothetical profile of the first enhanced structure, and the new hypothetical profile includes at least one new deterministic characteristic that comprises a height, a width, a thickness, a depth, a volume, an area, a dielectric property, a process recipe parameter, a processing time, a critical dimension, a spacing, a period, a position, or a line width; calculating a new enhanced simulated signal, and the new enhanced simulated signal corresponds to a new hypothetical profile of the first enhanced structure, and the new hypothetical profile includes a portion of the modified OTSM therein; and calculating a new difference between the enhanced profile signal and the new enhanced simulated signal, the enhanced profile signal and the new enhanced simulated signal being characterized by an enhanced set of wavelengths.

Then, the new difference is compared to a new enhanced profile library creation criteria; and either the first enhanced structure is identified using the new hypothetical profile and the new enhanced simulated signal is stored in the enhanced library, the new hypothetical profile of the first enhanced structure, including data for the modified OTSM portion if the new enhanced profile library creation criteria is met or a second corrective action is applied if the new enhanced profile library creation criteria is not met.

In some embodiments, a hypothetical profile may include an OTSM portion, or an ARC portion, or a dielectric portion, or a material layer portion, or a wafer portion, or a combination thereof.

When an enhanced library is created for an OTSM-related process and/or product, one or more enhanced library creation criteria can be used to determine the size, accuracy, and/or structure of the enhanced library.

Figure 8:
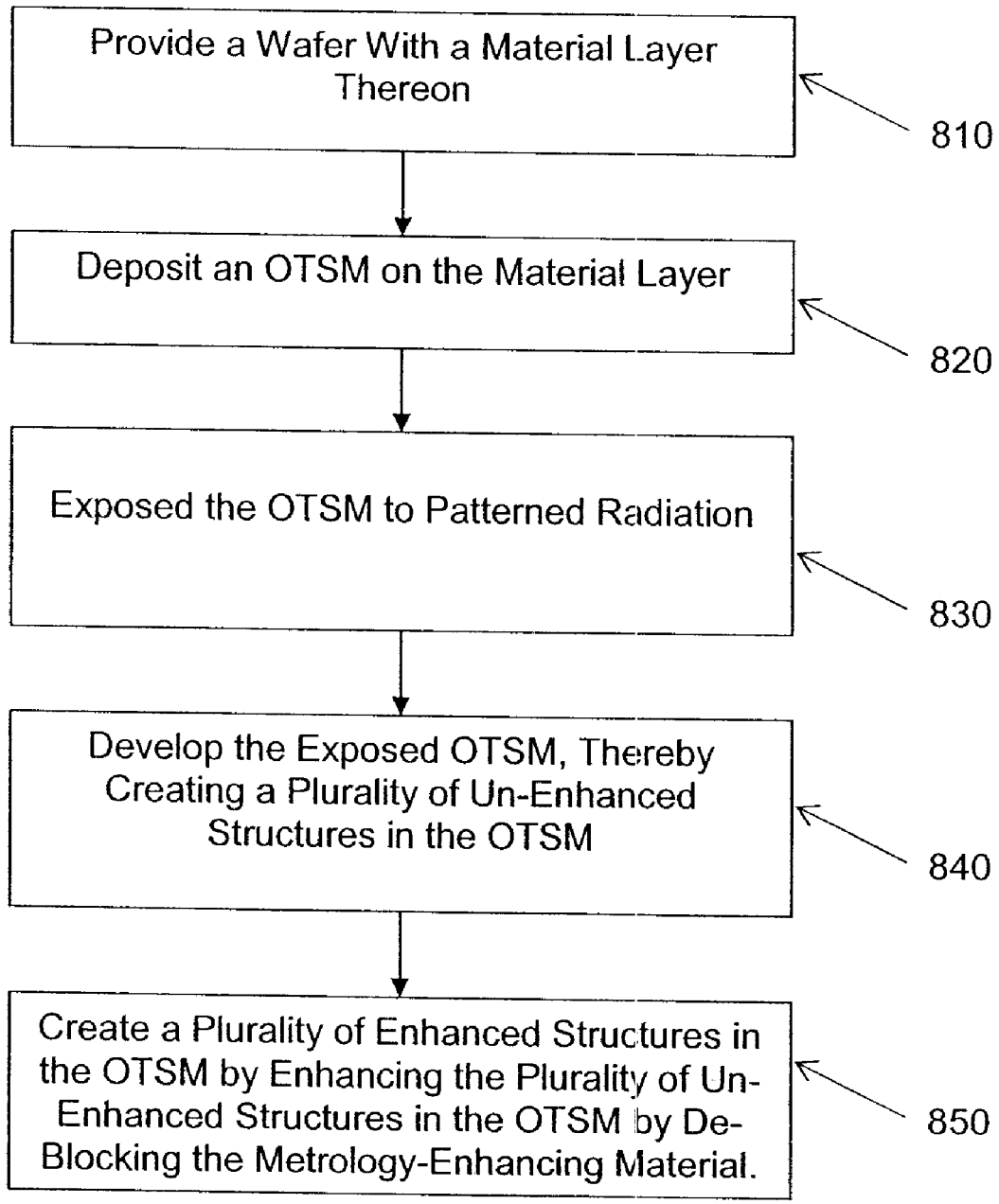
FIG. 8 illustrates an exemplary flow diagram of a procedure for using an OTSM in accordance with embodiments of the invention.

FIG. 8 illustrates an exemplary flow diagram of a procedure for using an optically tunable soft mask (OTSM) in accordance with embodiments of the invention. In the illustrated embodiment, a procedure 800 is shown for using an OTSM. In 810, a wafer having a material layer thereon can be provided. Alternatively, a material layer may not be required.

In 820, an OTSM can be deposited on the material layer. The OTSM can comprise tunable optical properties. One set of optical properties can be optimized, tuned and/or enhanced for an exposure process and another set of optical properties can be optimized, tuned and/or enhanced to enhance a measurement process. In addition, the second set of optical properties can be optimized, tuned and/or enhanced to produce enhanced structures in a material layer when the OTSM is used as a masking layer. The OTSM can comprise a polymer, an acid generator compound, and metrology-enhancing material coupled to the polymer using a blocking group, and the metrology-enhancing material can be used to tune (change) the optical properties after being de-blocked. A blocking group renders a functional group inactive until the functional group is de-blocked.

In 830, the OTSM can be exposed to patterned radiation created using a reticle and a radiation source, and one or more acids in the acid generator compound can be activated. For example, the radiation source can have a wavelength below approximately 300 nm, and an immersion lithography tool can be used.

In 840, the exposed OTSM can be developed thereby creating a plurality of un-enhanced structures in the OTSM.

In 850, a plurality of enhanced structures can be created in the OTSM by enhancing the plurality of un-enhanced structures in the OTSM. The metrology-enhancing material can be de-blocked during the developing process thereby creating the plurality of enhanced structures, and at least one of the enhanced structures can be characterized by the second set of optical properties. For example, at least one of the enhanced structures may comprise a periodic structure, a grating, or an array, or a combination thereof.

In some examples, the metrology-enhancing material can be de-blocked and/or activated by exposure to radiation, by exposure to an acid, by exposure to a base, by exposure to a solvent, or a developing solution, or by exposure to a temperature, or a combination thereof. In addition, the metrology-enhancing properties of the metrology-enhancing material can be established and/or activated by exposure to radiation, by exposure to an acid, by exposure to a base, by exposure to a solvent, or a developing solution, or by exposure to a temperature, or a combination thereof.

In some OTSMs, the tunable optical properties can include an extinction coefficient of less than approximately 0.5 at an exposure wavelength before exposure and can include an extinction coefficient of greater than approximately 0.5 at an exposure wavelength after exposure, and/or the tunable optical properties can include an index of refractive of less than approximately 0.3 at an exposure wavelength before exposure and can include an index of refractive of greater than approximately 0.3 at an exposure wavelength after exposure.

The tunable optical properties can be established at one or more wavelengths in a range from approximately 100 nm to approximately 1000 nm. Alternatively, some OTSMs may comprise some non-tunable optical properties that may be established at one or more wavelengths in a range from approximately 100 nm to approximately 1000 nm.

In other embodiments, the tunable optical properties can include first reflectance data before exposure and can include second reflectance data after exposure. In addition, the tunable optical properties can include first diffraction signal data before exposure and can include second diffraction signal data after exposure.

In some examples, the polymer can comprise an acid-labile group for providing the metrology-enhancing properties, an acid-labile group for providing base solubility, or an acid-labile group for providing etch resistance, or a combination thereof. In addition, at least one acid-labile group may not be an acetal group; at least one acid-labile group can be an ester; and at least one acid-labile group can be provided by polymerization of an alkyl acrylate group.

In addition, at least one coupled group can be a dye, a chromophore, a sensitizer, an enhancer, or a color additive, or a combination thereof.

Furthermore, the OTSM can comprise a basic additive, a dissolution inhibitor, an anti-striation agent, a plasticizer, a speed enhancer, filler, or a wetting agent, or a combination thereof.

In some embodiments, the method of using an OTSM can further comprise: (1) obtaining a first set of measurement data for the at least one enhanced structure characterized by a metrology-enhanced set of optical properties; (2) calculating a difference between the first set of measurement data and required data; (3) comparing the difference to a product requirement; and either (4) continuing to process the wafer if the product requirement is met, or (5) applying a corrective action if the product requirement is not met.

The applying of a corrective action process can include re-measuring the wafer and/or re-working the wafer by removing the OTSM that remains. Corrective actions can also include sending error messages, removing a wafer, pausing a process, etc.

Continuing to process the wafer can comprise: (1) creating a second set of enhanced structures in the material layer using a first set of enhanced structures in the OTSM as a soft mask; (2) removing the OTSM that remains; and (3) depositing a second material into the second set of enhanced structures in the material layer. The material layer can comprise semiconductor material, dielectric material, glass material, ceramic material, or metallic material, or a combination thereof. In addition, the second material comprises semiconductor material, dielectric material, glass material, ceramic material, metallic material, or planarization material, or a combination thereof.

Various methods can comprise the steps of (A) obtaining a second set of measurement data for the second set of enhanced structures in the material layer; (B) calculating a second difference between the second set of measured data and a second set of required data; (C) comparing the second difference to a second product requirement; and either (D) continuing to process the wafer if the second product requirement is met, or (E) applying a second corrective action if the second product requirement is not met.

In some OTSMs, one or more different sets of optical properties can be established using one or more metrology-enhancing materials attached to the polymer by one or more acid-labile groups.

In alternate embodiments, the methods of using an OTSM can comprise providing a wafer having a material layer thereon; and depositing an OTSM on the material layer. The OTSM can comprise tunable optical properties, a first set of optical properties being optimized, tuned and/or enhanced for an exposure tool and a second set of optical properties being optimized, tuned and/or enhanced for creating enhanced structures having enhanced measurement properties. The OTSM can comprise a polymer, an acid generator compound, and metrology-enhancing material coupled to the polymer, and the metrology-enhancing material establishing the second set of optical properties after being de-coupled.

Figure 9:
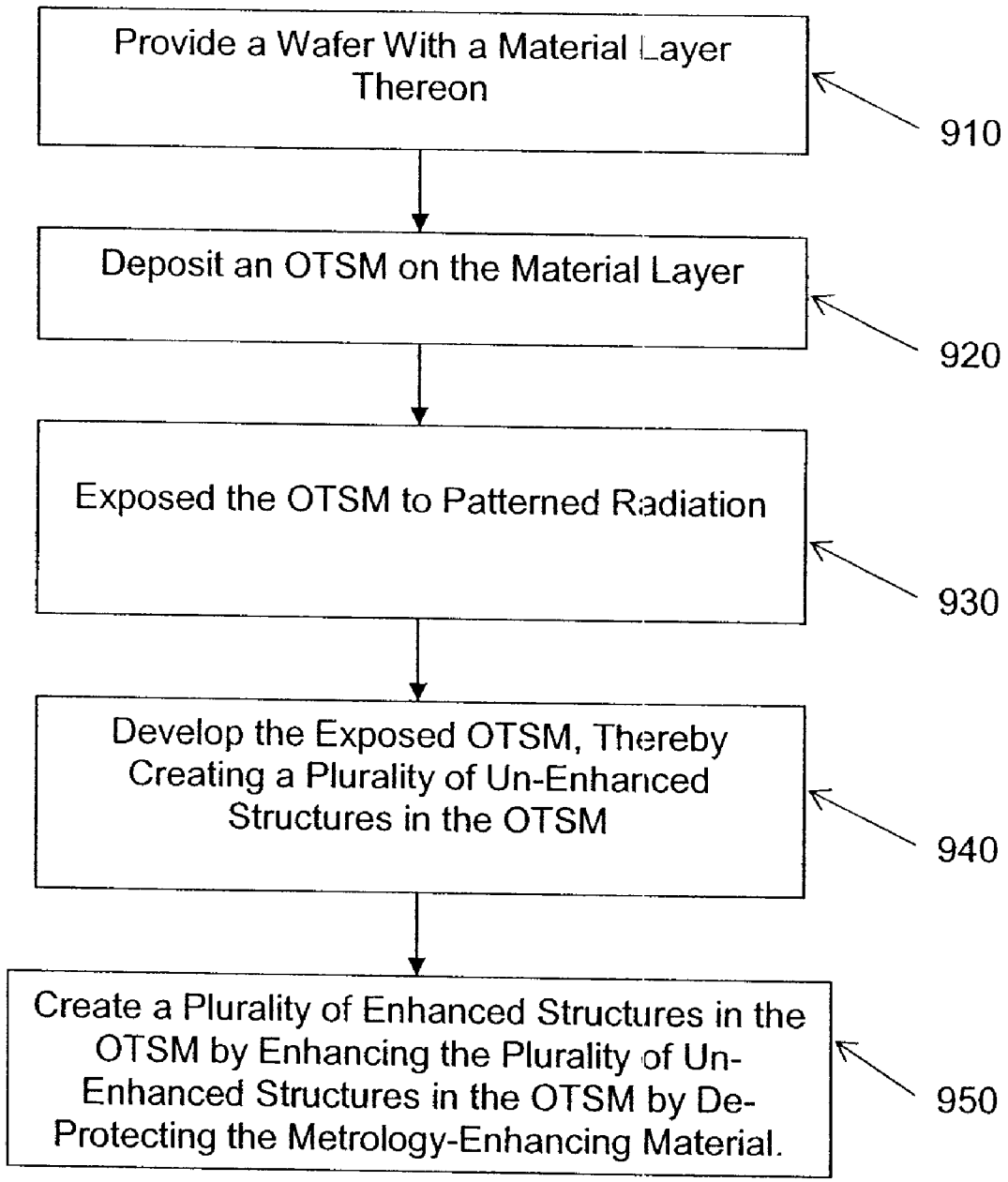
FIG. 9 illustrates an exemplary flow diagram of another procedure for using an OTSM in accordance with embodiments of the invention.

FIG. 9 illustrates an exemplary flow diagram of another procedure for using an optically tunable soft mask (OTSM) in accordance with embodiments of the invention. In the illustrated embodiment, a procedure 900 is shown for using an OTSM. In 910, a wafer having a material layer thereon can be provided. Alternatively, a material layer may not be required.

In 920, an OTSM can be deposited on the material layer. The OTSM can comprise tunable optical properties. A first set of optical properties being established for an exposure process and a second set of optical properties being established after the exposure process. The OTSM can comprise a polymer, an acid generator compound, and a metrology-enhancing material can be coupled to the polymer and or be a part of a polymer, and the metrology-enhancing material can establish the second set of optical properties after being activated after the exposure process.

In 930, the OTSM can be exposed to patterned radiation created using a reticle and a radiation source, and an acid in the acid generator compound can be activated. For example, the radiation source can have a wavelength below approximately 300 nm, and an immersion lithography tool can be used. During exposure, exposed regions and unexposed regions can be created in the OTSM, and a solubility change can occur in the exposed regions of the OTSM.

In 940, the exposed OTSM can be developed. During developing, the exposed regions can be removed and the unexposed regions can be used to create a plurality of un-enhanced structures in the OTSM. Alternatively, the un-exposed regions can be removed and the exposed regions can be used to create a plurality of un-enhanced structures in the OTSM.

In 950, a plurality of enhanced structures can be created in the OTSM by enhancing the plurality of un-enhanced structures in the OTSM. The metrology-enhancing material can be de-protected during the developing process thereby creating the plurality of enhanced structures, and at least one of the enhanced structures can be characterized by the second set of optical properties. A protecting group is a group that can be used to protect a functional group from unwanted reactions. After application, the protecting group can be removed to reveal the original functional group. For example, at least one of the enhanced structures may comprise a periodic structure, a grating, or an array, or a combination thereof.

In some examples, the metrology-enhancing material can be de-protected and/or activated by exposure to radiation, by exposure to an acid, by exposure to a base, by exposure to a solvent, or a developing solution, or by exposure to a temperature, or a combination thereof. In addition, the metrology-enhancing properties of the metrology-enhancing material can be established and/or activated by exposure to radiation, by exposure to an acid, by exposure to a base, by exposure to a solvent, or a developing solution, or by exposure to a temperature, or a combination thereof.

Figure 10:
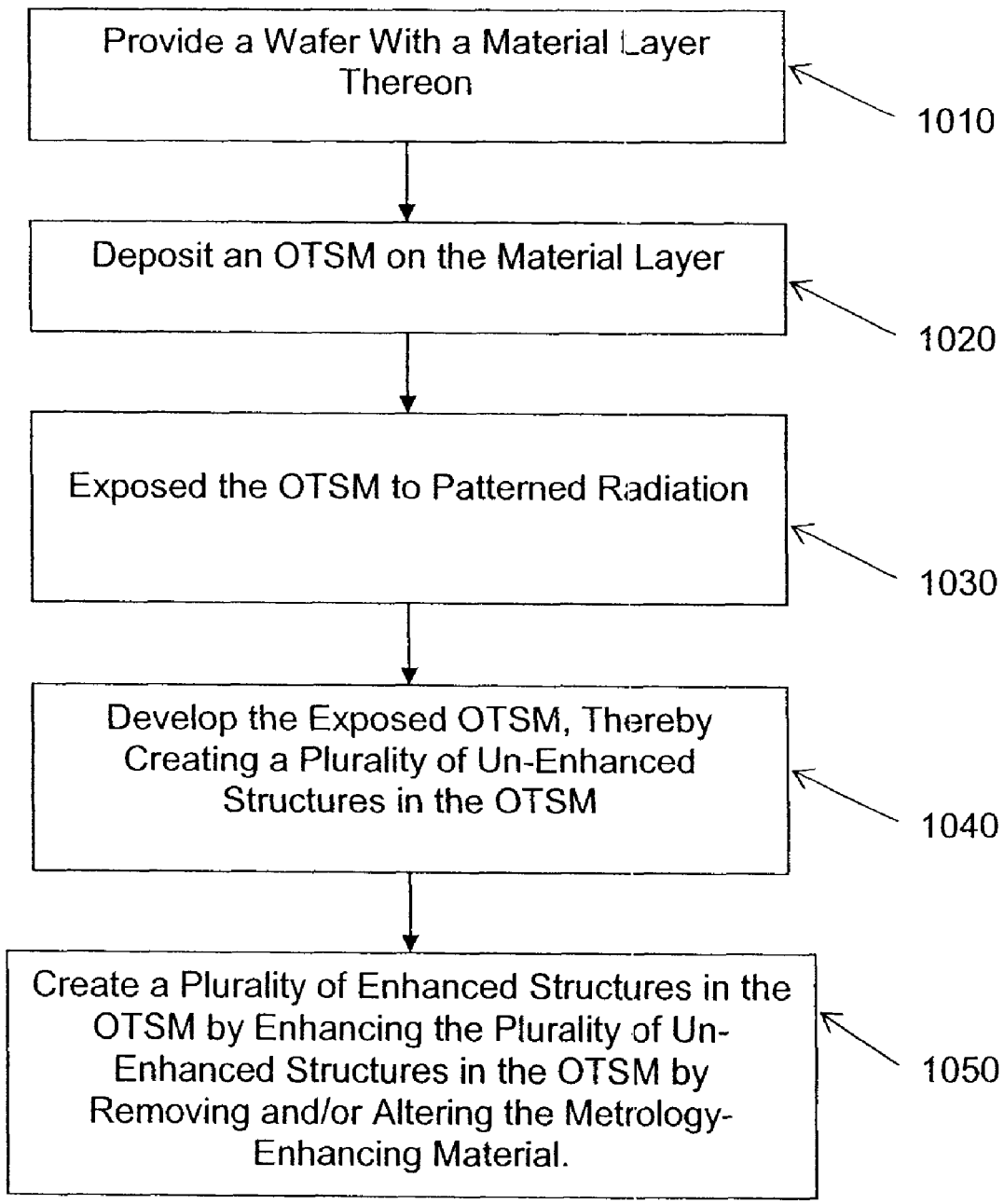
FIG. 10 illustrates an exemplary flow diagram of another procedure for using an OTSM in accordance with embodiments of the invention.

FIG. 10 illustrates an exemplary flow diagram of another procedure for using an optically tunable soft mask (OTSM) in accordance with embodiments of the invention. In the illustrated embodiment, a procedure 1000 is shown for using an OTSM. In 1010, a wafer having a material layer thereon can be provided. Alternatively, a material layer may not be required.

In 1020, an OTSM can be deposited on the material layer. The OTSM can comprise tunable optical properties. A first set of optical properties can be established to enhance an exposure process, and a second set of optical properties can be established to enhance a measurement process and/or a manufacturing process. The OTSM can comprise a polymer, an acid generator compound, and metrology-enhancing material coupled to the polymer using a leaving group, and the metrology-enhancing material can establish the second set of optical properties after the leaving group is altered and/or removed.

In 1030, the OTSM can be exposed to patterned radiation created using a reticle and a radiation source, and an acid in the acid generator compound can be activated. For example, the radiation source can have a wavelength below approximately 300 nm, and an immersion lithography tool can be used. During exposure, removable regions and un-removable regions can be created in the OTSM, and a solubility change can occur in the removable regions of the OTSM.

In 1040, the exposed OTSM can be developed. During developing, the removable regions can be removed and the un-removable regions can be used to create a plurality of un-enhanced structures in the OTSM.

In 1050, a plurality of enhanced structures can be created in the OTSM by enhancing the plurality of un-enhanced structures in the OTSM. The leaving group coupling the metrology-enhancing material can be altered and/or removed during the developing process thereby creating the plurality of enhanced structures, and at least one of the enhanced structures can be characterized by the second set of optical properties. For example, at least one of the enhanced structures may comprise a periodic structure, a grating, or an array, or a combination thereof.

In some examples, the leaving group coupling the metrology-enhancing material can be removed and/or altered by exposure to radiation, by exposure to an acid, by exposure to a base, by exposure to a solvent, or a developing solution, or by exposure to a temperature, or a combination thereof. In addition, the metrology-enhancing properties of the metrology-enhancing material can be established and/or activated by exposure to radiation, by exposure to an acid, by exposure to a base, by exposure to a solvent, or a developing solution, or by exposure to a temperature, or a combination thereof.

In other embodiments, the tunable optical properties can be optimized, tuned and/or enhanced for an immersion lithography tool, or an enhanced measurement tool, or a combination thereof.

In some embodiments, the OTSM can comprise tunable optical properties, a first set of optical properties can be optimized, tuned and/or enhanced for an exposure process and a second set of optical properties can be optimized, tuned and/or enhanced for a measurement process, the OTSM can comprise a polymer, an acid generator compound, and metrology-enhancing material coupled to the polymer as a leaving group, and the second set of optical properties can be established after the leaving group is removed. The leaving group can establish one or more metrology-enhancing properties. A leaving group is a group that can be displaced in a substitution or elimination reaction.

Figure 11:
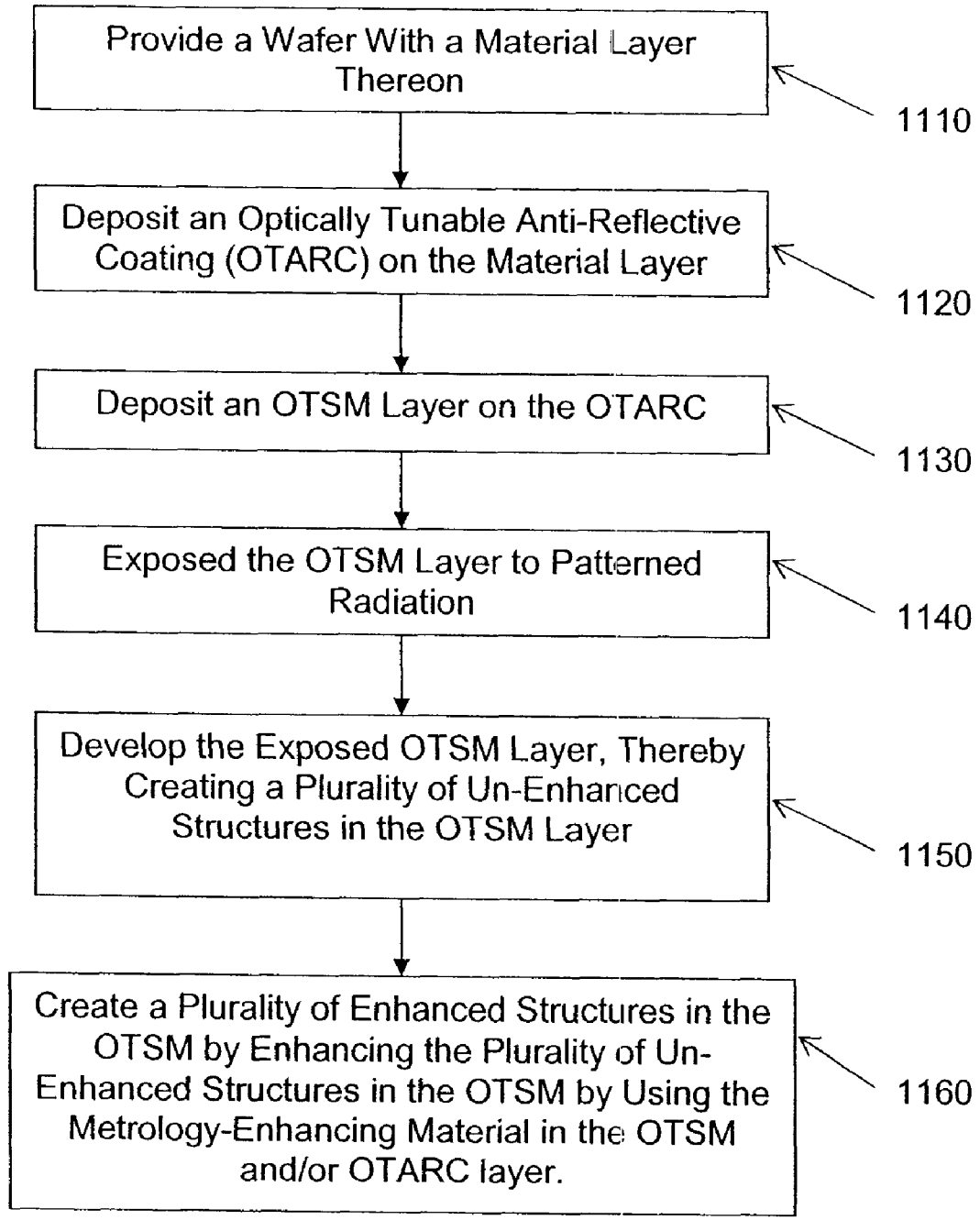
FIG. 11 illustrates an exemplary flow diagram of a procedure for using an optically tunable anti-reflective coating (OTARC) in accordance with embodiments of the invention.

FIG. 11 illustrates an exemplary flow diagram of a procedure for using an optically tunable anti-reflective coating (OTARC) in accordance with embodiments of the invention. In the illustrated embodiment, a procedure 1100 is shown for using an OTARC. In 1110, a wafer having a material layer thereon can be provided. Alternatively, a material layer may not be required.

In 1120, an OTARC can be deposited on the material layer. The OTARC can comprise a first set of optical properties optimized, tuned and/or enhanced for an exposure process and a second set of optical properties optimized, tuned and/or enhanced for a measurement process. The OTARC layer can comprise a polymer, an acid generator compound, and a metrology-enhancing material being coupled to the polymer as a leaving group, and the second set of optical properties can be established after the leaving group is removed. Alternatively, the metrology-enhancing material may be coupled to the polymer differently, and the second set of optical properties may be established after the metrology-enhancing material is removed, activated, de-protected, and/or de-blocked.

In 1130, an OTSM layer can be deposited on the OTARC layer. In some embodiments, a resist layer can be deposited on the OTARC layer. In other embodiments, a different mask material may be deposited on the OTARC layer. Alternatively, an OTSM may be used along with the resist layer. In other embodiments, an OTSM may comprise an anti-reflective layer.

In 1140, the OTSM layer can be exposed to radiation using a reticle and a radiation source, and removable regions and un-removable regions can be established in the resist layer. A solubility change can occur in the removable regions of the resist layer.

In 1150, the exposed OTSM layer can be developed. For example, the removable regions can be removed, and the un-removable regions can be used to create a plurality of un-enhanced structures in the OTSM layer. The metrology-enhancing material can be de-blocked during the developing process thereby creating the plurality of enhanced structures in the OTSM layer and changing the optical properties of the developed OTSM layer. The changed optical properties can improve the accuracy of the optical metrology measurements.

In 1160, the optical properties can be changed in the OTARC layer. For example, the leaving group can be removed during the developing process and reflectivity data for the OTARC layer can be changed. In other examples, a blocking group and/or protecting group can be de-blocked and/or de-protected during the developing process. Alternatively, the optical properties in the OTARC layer may be changed and/or activated during the exposure step.

Alternatively, when a resist layer is used, un-enhanced structures can be created in the resist layer. The metrology-enhancing material in the OTARC layer can be activated during the developing process thereby creating an OTARC layer with metrology-enhancing properties. For example, the optical properties of the OTARC layer can be changed, and the changed optical properties of the OTARC layer can be used to improve the accuracy of the optical metrology measurements made on the un-enhanced structures that were created in the resist layer.

In other embodiments, the first set of optical properties can include first reflectance data before exposure and the second set of optical properties can include second reflectance data after exposure. In addition, the first set of optical properties can include first diffraction signal data before exposure and the second set of optical properties can include second diffraction signal data after exposure.

In various examples, the polymer can comprise a monomer, a copolymer, a tetrapolymer, or a pentapolymer, or a combination thereof.

For example, a blocked group, or a leaving group, or a protected group, or a cleaved group can be a dye, a chromophore, a sensitizer, an enhancer, a color mask, or a color additive, or a combination thereof. A cleaved group is a group that can be cleaved from the polymer under appropriate conditions. In addition, a de-blocked group, or a remaining group, or a de-protected group, or an activated group can be a dye, a chromophore, a sensitizer, an enhancer, a color mask, or a color additive, or a combination thereof.

In some embodiments, an enhanced image and/or pattern can be established using the enhanced structures, and the enhanced image can be characterized by the second set of optical properties. The metrology-enhancing properties associated with the metrology-enhancing material can be activated when a coupling element is removed during the developing process. The OTSM can include a polymer, an acid generator compound, and a metrology-enhancing material. The acid generator compound can be coupled to the polymer or can be part of the polymer. In addition, the metrology-enhancing material can be coupled to the polymer or can be part of the polymer. Coupling elements can include leaving groups, blocking groups, protecting groups and other groups known to those skilled in the art.

In some embodiments, one or more wafers can be measured to verify that the OTSM is being fabricated correctly and/or to verify that the semiconductor processing system is producing quality devices. In other embodiments, one or more wafers can be measured to verify that the material layer is being processed correctly and/or to verify that the OTSM-related processes are producing quality devices. When performing a measurement process, one or more enhanced structures in the OTSM can be measured using an enhanced set of wavelengths; the measured data for the one or more enhanced structures in the OTSM can be compared to a product requirement; and either the wafer processing can continue if the product requirement is met, or a corrective action can be applied if the product requirement is not met.

When a corrective action is required, the wafer can be re-measured. The re-measurement may include the same measurement sites, or additional sites, or additional wafers, or a combination thereof. In other cases, a corrective action can include removing the OTSM and depositing a new OTSM. The re-measurement process can include re-measuring the optical properties associated with an OTSM or an OTSM-related process.

In some embodiments, when a measurement procedure is performed one or more metrology libraries can be used. During a measurement procedure, an optical metrology tool can be used, and a measured signal can be obtained off a first structure that can be one of the enhanced structures in the OTSM, and the first structure can be characterized by the second set of optical properties.

The enhanced profile library includes enhanced profile shapes and enhanced profile parameters that are more accurate than the comparable data items in an un-enhanced profile library. In addition, the enhanced profile library includes enhanced profile signals that are more accurate than the signals in an un-enhanced profile library. For example, an enhanced profile signal can include data points at wavelengths that are not used for the un-enhanced signals.

When fabricating an OTSM and/or an OTARC, tradeoffs between using organic and inorganic materials can be examined. The optical absorption, feature CD profile, CD uniformity, line edge and sidewall roughness, and line feature slimming under Scanning Electron Microscope (SEM) inspection and analysis properties can be analyzed when fabricating an OTSM.

An OTSM and/or OTARC can be used in the fabrication of metal gates, polygates, doping profiles, contacts, vias, and trenches in semiconductor devices.

Some OTSMs can include one or more ArF resist materials, but this is not required. Alternatively, other materials may be used. When ArF resist materials are used, they can include different main polymer elements including cycloolefin—maleic anhydride (COMA), acrylate, and cycloolefin (CO). For example, an acrylate-based polymer may include pendant aliphatic and alicyclic units with acid-labile groups on an acrylate backbone.

In some embodiments, an OTSM may include one or more resist layers designed for ArF exposure tools and a BARC/ARC layer to minimize reflectivity problems. BARC/ARC materials can be used to ensure uniform radiation effects within and/or across the OTSM. Swing curves can be provided that are periodic and dependent on the thickness of the resist material and the optical properties of the wafer, resist, and ARC materials. For example, the OTSM can be designed so that there is a uniform photochemical transformation that minimizes line width variation and maximizes the uniformity of the metrology-enhancing process. In addition, the enhanced structures and/or features of the OTSM can have smaller line edge and sidewall roughness values, and the enhanced structures and/or features of the OTSM will not be reduced during an SEM tool inspection process.

When BARC/ARC materials are used in and/or with an OTSM, they can be designed to have better etch selectivity than the other OTSM materials. For example, during re-work processes, OSTM materials can be selectively stripped without damage to underlying structures, and re-work processes for OSTM layers may use oxygen-based or fluorine-based plasma.

When fabricating an OTSM designed for 193 nm radiation, immersion lithography enables smaller features to be printed, and therefore the OTSM may be thinner to achieve the required Depth of Field (DOF) at the desired wavelength, and the OTSM materials used may be softer and less etch-resistant than the resist materials designed for the longer wavelengths. For example, an OTSM can be produced using spin-on organic materials that can be characterized by their optical parameters (n and k), etch rate in dry chemistry, conformality properties, reflectivity properties, thickness requirements, and compatibility properties.

An OTSM can be used during gate level processes, during interconnect level processing, and during implant layer processing. For example, an OTSM can include photosensitive material that can be completely soluble in the exposed area, but is insoluble in the unexposed area. Then, a matching developer soluble ARC/BARC material can be used, and the matched materials can provide more well-defined features. Furthermore, an OTSM that comprises developer-soluble materials can have these materials removed during the developing process and may not require an etching step.

In addition, OTSM material and/or ARC material can be incorporated into spin-on materials, such as spin-on glass (SOG) material. Exemplary spin-on-glass materials may include methylsiloxane, methylsilsesquioxane, phenylsiloxane, phenylsilsesquioxane, methylphenylsiloxane, methylphenylsilsesquioxane, and silicate polymers, and the spin-on-glass compositions can be dissolved in appropriate solvents to form coating solutions and can be applied to various layers of materials during the fabrication of semiconductor devices. The spin-on techniques can include a timed spin, a dispense amount spin, a thickness related spin, or thermal bake steps, to produce an SOG film having the required optical properties. For example, these processes can include spin speeds of between 1000 and 4000 rpm; spin times can vary between 10 and 200 seconds; thermal processing steps can be performed at temperatures between 50 degree Celsius and 450 degree Celsius, and thermal processing steps can be performed for durations lasting between 10 and 300 seconds. When absorbing anti-reflective SOG films are fabricated, the refractive indices can vary between about 1.3 and about 2.0 and the extinction coefficients can be greater than 0.2 at 190 nm, and the extinction coefficient can be less than 0.2 at wavelengths greater than 190 nm.

When absorbing materials are used in an OTSM, they can have absorption properties that are wavelength dependent, and their absorbing properties should be predictable and relatively constant over a range of wavelengths to be useful. For example, the range of wavelengths can be greater than five percent of the exposure wavelength and can be centered on the exposure wavelength.

When metrology-enhancing materials are used in an OTSM, they can affect the optical properties of the layer at different wavelengths, and their affect on the optical properties can be relatively constant over a range of wavelengths to be useful. In one example, the range of wavelengths can be greater than five percent of the exposure wavelength and can be centered on the exposure wavelength. In another example, the range of wavelengths can be greater than five percent of the exposure wavelength and can be located at wavelengths that are higher than the exposure wavelength.

Metrology-enhancing materials that only have narrow enhancement windows that are less than approximately two nm wide are not as desirable as materials having wider enhancement windows.

In some embodiments, the metrology-enhancing materials may be activated during and/or after a Post Apply Bake (PAB) step, and this metrology-enhancing behavior can be simulated by developing a lattice-type model that approximates the configuration of the OTSM during and/or after the PAB step. In addition, the effects of solvent evaporation and film shrinkage during the PAB step can also be modeled.

Some commercially available software packages may be used to model and/or simulate the optical properties of the optically tunable resist and/or metrology-enhancing materials. The modeling and/or simulating can be performed using different imaging sources, different metrology-enhancing materials, different masks, and different layer configurations. In addition, the modeling and/or simulating can be performed over wide and/or narrow wavelength ranges, and transforms may be used to improve accuracy and/or lessen the computational time. The modeling and/or simulating can be performed in real-time and prediction models and maps can be developed for the different optically tunable resist and/or metrology-enhancing materials.

In additional embodiments, one or more metrology-enhancing materials may be activated by, during and/or after a thermal process. The temperature may be used to help diffuse one or more metrology-enhancing materials or one or more of the optically tunable resist materials during a metrology-enhancement procedure. For example, the Post Exposure Bake (PEB) temperature can be established and/or changed to control the chemical activation reaction, to control the solubility of the polymer in many chemically amplified resists, and to control the uniformity of the enhanced-metrology properties. In addition, modeling and/or simulating can be performed in real-time and thermal models and maps can be developed for the different optically tunable resist and/or metrology-enhancing materials.

The metrology-enhancing properties may be controlled and/or optimized by using a fixed or variable development time and/or a fixed or variable thermal processing time. These times may depend on the time required to complete the de-protection and/or activation of the metrology-enhancing material. When the de-protection and/or activation of the metrology-enhancing material occur, the optical properties of the OTSM change, thereby providing improved metrology properties for the features within a patterned OTSM layer.

When chemical amplification is used with metrology-enhancing materials, it can allow a single generator to cause many metrology-enhancing reactions to occur, and this can increase the speed and/or uniformity of the metrology-enhancing reactions. During a chemical amplification process, acid molecules can move and react with many reactive polymer sites, and this movement can be controlled to optimize the shape of the exposed regions and unexposed regions, to control the optical properties of the unexposed regions and/or exposed regions, to optimize the performance of the metrology-enhancing material, and to optimize the uniformity of the enhanced features. In addition, when chemically amplified resist materials are used in an OTSM, the exposure process can be used to generate acid catalyst molecules that can react with the resist polymer to change the solubility of the OTSM in exposed regions. Acid mobility is a complex mechanism, and lattice-based models can be developed and used to predict the performance of the metrology-enhancing process. The inputs to lattice-based models can include the solubility parameters of the metrology-enhancing components, and they can be used to calculate the interaction energy between lattice components. The activation energies of the various reactions can also be used along with the process temperatures.

An OTSM can be developed using an aqueous solution of 0.26 N tetramethylammonium hydroxide (TMAH), and the dissolution of a resist material can be dependent on the chemical reactions between the basic developer solution and the acid in the polymer chains. This can be modeled as a reaction-limited process, and the modeling inputs can include the structure of the polymer, the structure of the metrology-enhancing material, and the ionized amount.

Using one or more fluorine-containing compounds in an OTSM can provide improved performance for deep ultraviolet lithography at 193 nm and 157 nm. The improved performance can be characterized by the high optical transparency of partially fluorinated materials and the high acidity of fluorocarbinols.

When an OTSM is designed for use with immersion lithography processes, out-gassing from the OTSM material and/or ARC materials can be a problem due to the potential contamination of the exposure lens. Out-gassing can cause transmission loss and distorted images. In some embodiments, a thin cap layer may be required to eliminate the contamination issue. When topcoats are used in an OTSM, they should be soluble in TMAH developers but be insoluble in the immersion fluid; they should be highly transparent at 193 nm, and be compatible with the other materials in the OTSM and the immersion fluid.

When chemically amplified materials are used in optically tunable resists, an acid can be generated during the exposure process can initiate a catalytic reaction that can be used to activate a metrology-enhancing material and/or process that can be further controlled during a subsequent baking step. During the baking step, the acid can diffuse through the optically tunable resist materials producing catalyzed and un-catalyzed areas, and the acid diffusion can also produce enhanced features in the optically tunable resist that have enhanced metrological properties. For example, diffusion lengths can be at least 20 nm for chemically amplified materials being used at exposure wavelengths of 193 nm.

Chemical amplification can be used to activate and/or control the metrology-enhancing materials in an OTSM. Chemical amplification can more effectively and more uniformly activate and distribute the metrology-enhancing materials in an OTSM by increasing the number of chemical reactions caused by a single photon that lead to the solubility change in the resist. In the unexposed state, an acid-labile protecting group can be used to inhibit the dissolution rate of the resist materials and/or to inhibit the metrology-enhancing properties of the metrology-enhancing materials in an OTSM. For example, this may be done by replacing the base-soluble hydroxyl with an insoluble group. After exposure to ultraviolet light, acid can be generated within the OTSM; the acid can react with acid-labile protecting group, which may be an ester or an anhydride; and a reactive hydroxyl group may be formed with or without a metrology-enhancing group.

When some OTSMs are produced, the chemical amplification can be established by replacing one or more hydroxyl groups with acid-labile protecting groups in a polymer resin. A chemically amplified OTSM can include: a polymer resin, a photoacid generator (PAG) to provide sensitivity to ultraviolet light, a dissolution inhibitor to provide a solubility switch before and after exposure, and a metrology-enhancing component to modify the optical properties of the OTSM after exposure. Dissolution inhibitors may be used with a metrology-enhancing component, and may be oligomers of an acid-labile protected monomer.

Line-edge roughness (LER) and/or line-width roughness (LWR) can be improved by using and/or producing an OTSM. When an OTSM is produced, polymers, protecting groups, PAGs, metrology-enhancing materials, and/or solvents can be used to provide enhanced structures and/or features with substantially no LER.

The optical transparency of an OTSM at the exposure wavelength can be an important parameter in determining the quality of lithographic images that can be established using the OTSM. For example, an OTSM can have an absorbance coefficient that varies with wavelength and application.

The optical transparency and/or diffraction properties of the OTSM can also be important at other wavelengths when a developed OTSM is being measured using optical metrology techniques.

In some examples, the OTSM can include tunable silicon-containing resist compositions that are capable of high resolution lithographic performance, especially in single or multilayer lithographic applications using 193 nm or shorter wavelength imaging radiation. The OTSM can include an acid-sensitive imaging polymer, a non-polymeric silicon additive, a radiation-sensitive acid generator, and a metrology-enhancing additive. For example, the metrology-enhancing additive can be radiation-sensitive, acid-sensitive, base-sensitive, solvent-sensitive, or temperature-sensitive, or a combination thereof.

The metrology-enhancing additive can be used to alter one or more optical properties of the OTSM thereby enhancing the accuracy of the optical metrology data. The OTSM can provide high resolution lithographic patterns having enhanced features in monolayer or multilayer lithographic processes. In addition, OTSM-related procedures and/or recipes can be created and used to form enhanced (more accurate) structures using a patterned OTSM.

The imaging component of the OTSM is not limited to the use of any specific imaging polymer. In some embodiments, the imaging polymer can be an acid-sensitive polymer having acid-labile pendant groups that can be cleaved in the presence of acid generated during exposure. Alternatively, cleaving may occur during a thermal processing step.

In other embodiments, the polymer used in an OTSM may have little or no silicon content, and one or more non-polymeric silicon additives may be used to provide the metrology-enhancement properties for the enhanced features. For example, the polymer may contain a monomer such as a cyclic olefin, an acrylate, or a methacrylate.

In some embodiments, the OTSM may contain small molecules and/or products that can be formed during the development process and that can be used as metrology-enhancing additives. In addition, the small molecules and/or products may undergo secondary reactions with other components of the film, including the polymer and the acid before exhibiting their metrology-enhancing properties.

An optically tunable resist material may comprise acid-labile pendant components that can be used to improve solubility in aqueous alkaline solutions and/or to provide the metrology-enhancing properties of the resist materials, and one or more monomers having different protecting groups may be used.

Exemplary acid-labile protecting components may include tertiary alkyl (or cycloalkyl) esters (e.g., t-butyl, methyl cyclopentyl, methyl cyclohexyl, and methyl adamantyl), ketals, and acetals.

Upon exposure to imaging radiation, one portion of the protecting groups in the exposed portions of the OTSM may be cleaved thereby causing a solubility shift, and another portion of the protecting groups may be cleaved thereby causing a change in the optical properties of the OTSM.

When the OTSM is to be used in a 157 nm lithographic process, the imaging polymer can contain fluorine-containing compositions and/or silicon-containing compositions.

In some embodiments, the OTSM may contain a non-polymeric silicon additive that can have ten or more carbon atoms. For example, a non-polymeric silicon additive may contain acid-labile groups that can be used to inhibit the metrology-enhancing properties of one or more materials in the OTSM. Exemplary non-polymeric silicon additives may include: Tris(trimethylsilylmethyl)1,3,5-cyclohexanetricarboxylate (TMSCT), Bis(trimethylsilylmethyl)1,4-cyclohexanedicarboxylate (TMSCD), Bis(bis(trimethylsilyl)methyl)1,4-cyclohexanedicarboxylate (BTSCD), Bis(tris(trimethylsiloxysilyl)methyl)1,4-cyclohexanedicarboxylate (BSOSCD), Tris(trimethylsiloxysilyl)methyl 1-adamantanecarboxylate (SOSAC), 2,5-Bis(trimethylsilylmethyl-carboxyloxy)-2,5-dimethylhexane (BTSDMH), or lactone-containing non-polymeric silicon additives.

The OTSM may also include one or more radiation-sensitive acid generators. Exemplary radiation-sensitive acid generators may include modified onium salts such as triaryl sulfonium or diaryliodonium hexafluoroantimonate, hexafluoroarsenates, triflates, perfluoroalkane sulfonates (e.g., perfluoromethane sulfonate, perfluorobutane, perfluorohexane sulfonate, perfluorooctane sulfonate, etc.), perfluoroalkyl sulfonyl imide, perfluoroalkyl sulfonyl methide, perfluoroaryl sulfonyl imide, perfluoroaryl sulfonyl methide; substituted aryl sulfonates such as pyrogallols (e.g. trimesylate of pyrogallol or tris(sulfonate) of pyrogallol), sulfonate esters of hydroxyimides, N-sulfonyloxynaphthalimides (N-camphorsulfonyloxynaphthalimide, N-pentafluorobenzenesulfonyloxynaphthalimide), .alpha.-.alpha.'bis-sulfonyl diazomethanes, naphthoquinone-4-diazides, alkyl disulfones or others.

Exemplary acid generators for the 193 nm exposure wavelength may include onium salts and sulfonate esters of hyroxyimides, such as diphenyl iodonium salts, triphenyl sulfonium salts, dialkyl iodonium salts, or trialkylsulfonium salts. Exemplary acid generators for the 248 nm exposure wavelength may include onium salts, such as diphenyl iodonium salts, triphenyl sulfonium salts or sulfonate esters of hydroxyimides.

Additional exemplary ionic PAGs may include diazonium salts, iodonium salts, sulfonium salts, or non-ionic PAGs may include diazosulfonyl compounds, sulfonyloxy imides, or nitrobenzyl sulfonate esters, although any photosensitive compound that produces an acid upon irradiation may be used. For example, the onium salts may be used in a form soluble in organic solvents, mostly as iodonium or sulfonium salts, examples of which are diphenyliodonium trifluoromethane sulfonate, diphenyliodonium nonafluorobutane sulfonate, triphenylsulfonium trifluoromethane sulfonate, triphenylsulfonium nonafluorobutane sulfonate, or the like. Other compounds that form an acid upon irradiation that may be used are triazines, oxazoles, oxadiazoles, thiazoles, or substituted 2-pyrones. Phenolic sulfonic esters, bis-sulfonylmethanes, bis-sulfonylmethanes, or bis-sulfonyidiazomethanes, triphenylsulfonium tris(trifluoromethylsulfonyl)methide, triphenylsulfonium bis(trifluoromethylsulfonyl)imide, diphenyliodonium tris(trifluoromethylsulfonyl)methide, diphenyliodonium bis(trifluoromethylsulfonyl)imide or their homologues can also be used. Mixtures of PAGs may also be used, and frequently mixtures of ionic and nonionic PAGs are used.

In many examples, the OTSM material can include base additives that can be used to control the diffusion process and improve the image. Alternatively, a basic additive may be used as a metrology-enhancement material and may be used to change the optical properties of the OTSM. Exemplary bases can include amines, ammonium hydroxide, or photosensitive bases. In addition, base additives may include aliphatic or alicyclic tertiary alkyl amines or t-alkyl ammonium hydroxides such as t-butyl ammonium hydroxide (TBAH). Other exemplary bases may include tetrabutylammonium lactate, or a hindered amine. The base additive can be used in relatively small amounts, e.g. about 0.03 to 5 percent by weight relative to the total solids.

Furthermore, one or more dyes and/or sensitizer may be used to provide the metrology-enhancing properties of the OTSM.

In some embodiments, an OTSM may be applied directly over a planarization material that has already been deposited on a wafer, or in other embodiments, an OTSM may include a planarization material. For example, the planarization material may include styrene, adamantyl acrylate, and/or glycidyl acrylate.

In some embodiments, 193 nm UV radiation may be used, and the total exposure energy may be less than or equal to approximately 100 millijoules/cm$^2$.

The OTSM can include a pattern of enhanced features that can be measured using optical metrology techniques. The enhanced features have optical properties that allow a more accurate metrology result to be obtained.

The pattern of enhanced features from the structures of the OTSM may then be transferred to the underlying layer of the wafer by reactive ion etching or other etching techniques known in the art. After etching, the remaining OTSM material may be removed using conventional stripping techniques.

The transferred features can be measured using optical metrology techniques to verify that the enhanced features have been transferred correctly. For example, an enhanced and/or modified metrology tool having an increased measurement range may be used.

When reflectance values are used to characterize an OTSM, the OTSM can have tunable reflectance values. A first set of reflectance values can be established before exposure, and a second set of reflectance values can be established before a measurement process is performed. Alternatively, an OTSM may have one set of reflectance values before exposure and another set of reflectance values after exposure. Reflectance values can be wavelength dependent. For example, a reflectance value can be determined using $I_T/I_I$ where $I_I$ is the intensity of light entering the film and $I_T$ is the intensity of light exiting the film. Anti-reflecting films can have reflectance values that can be less than ten percent at wavelengths other than an exposure wavelength.

When (n and k) values are used to characterize an OTSM, the OTSM can have tunable sets of (n and k) values. One set of (n and k) values can be established before exposure and another set of (n and k) values can be established before a measurement process is performed. Alternatively, an OTSM may have one set of reflectance values before exposure and another set of (n and k) values after exposure.

When one or more BARC/ARC films are required, they can be included as a part of the OTSM. Alternatively, they may be positioned between the wafer and the OTSM. One or more of the BARC/ARC films may be subsequently patterned and operate as an etch hard mask. When anti-reflecting films are used, these films can have a relatively high extinction coefficient (k) and/or a relatively high refractive index (n), and these values can vary with material, wavelength (frequency), and/or thickness.

Silicon-containing materials may be used when fabricating an OTSM since the n and k values may be determined by controlling the silicon content of a silicon-containing film, such as a SiON or $SiO_x$ film. For example, when an OTSM includes multiple layers, two silicon-containing films can be used that have compatible (matching) optical properties, such as (n) and (k), that can be selected to provide a minimum amount of reflection (i.e., less than 1%) within a wavelength range around the exposure wavelength. In addition, one or more silicon-containing films may be patterned and used as an etch hardmasks. When an OTSM includes multiple layers, the thicknesses, the extinction coefficients and/or the index of refractions can be controlled and/or matched to minimize reflectivity before and during exposure, and the reflectivity can be increased by changing one or more extinction coefficients and/or one or more indices of refraction after exposure.

Non-aromatic polymers may used in some cases since they can be substantially opaque at about 193 nm. Furthermore, at lower wavelengths, the reflection component becomes more important, and at the lower wavelengths, antireflective coatings can be used.

In some embodiments, an OTSM can include antireflective material and resist material that can be exposed in a single processing step. Both materials can be heated and developed during the same time and using the same developer. This can simplify the lithographic process. In addition, the antireflective material and/or the resist material can be constructed to have reflectivity properties that change during the exposure, thermal, and/or development process to allow more accurate metrological measurements to be made. For example, the antireflective material and resist material can be deposited on the wafer and the resist, material can be deposited on the antireflective material and resist material. When the OTSM is exposed to radiation, an acid can be generated in both the antireflective material and resist material, and the acid generation process can be used to alter the optical properties of the antireflective material and/or the resist material. When the OTSM is developed, the exposed regions of the antireflective material and the resist material can be removed, and a pattern can remain that has features and/or structures having enhanced metrological properties that can provide more accurate measurement results and more accurate etching results.

In some embodiments, one or more chromophores may be activated and/or altered to provide the enhanced metrological properties of the OTSM. In other embodiments, one or more dyes may be activated and/or altered to provide the enhanced metrological properties of the OTSM.

Exemplary dye may be monomeric, polymeric or mixtures of both. Examples of absorbing groups that may be contained in an additive absorbing compound are substituted and unsubstituted phenyl, substituted and unsubstituted anthracyl, substituted and unsubstituted phenanthryl, substituted and unsubstituted naphthyl, substituted and unsubstituted heterocyclic rings containing heteroatoms such as oxygen, nitrogen, sulfur, or combinations thereof, such as pyrrolidinyl, pyranyl, piperidinyl, acridinyl, and quinolinyl. In addition, exemplary dyes may include monomers or polymers of triphenylphenol, 2-hydroxyfluorene, 9-anthracenemethanol, 2-methylphenanthrene, 2-naphthalene ethanol, 2-naphthyl-beta-d-galactopyranoside hydride, hydroxystyrene, styrene, acetoxystyrene, benzyl methacrylate, N-methyl maleimide, vinyl benzoate, vinyl 4-tert-butylbenzoate, ethylene glycol phenyl ether acrylate, phenoxypropyl acrylate, benzyl mevalonic lactone ester of maleic acid, 2-hydroxy-3-phenoxypropyl acrylate, phenyl methacrylate, benzyl methacrylate, 9-anthracenylmethyl methacrylate, 9-vinylanthracene, 2-vinylnaphthalene, N-vinylphthalimide, N-(3-hydroxy)phenyl methacrylamide, N-(3-hydroxy-4-hydroxycarbonylphenylazo)phenyl methacrylamide, N-(3-hydroxyl-4-ethoxycarbonylphenylazo) phenyl methacrylamide, N-(2,4-dinitrophenylaminophenyl) maleimide, 3-(4-acetoaminophenyl)azo-4-hydroxystyrene, 3-(4-ethoxycarbonylphenyl)azo-acetoacetoxy ethyl methacrylate, 3-(4-hydroxyphenyl)azo-acetoacetoxy ethyl methacrylate, or tetrahydroammonium sulfate salt of 3-(4-sulfophenyl)azoacetoacetoxy ethyl methacrylate.

In some embodiments, the OTSM can include an alkali soluble fluorinated polymer, metrology-enhancing materials, a PAG, and a cross-linking agent, and the OTSM can be fabricated using one or more fluorinated polymers that are transparent at 193 nm and/or 157 nm. One or more cross-linking agents can be used to add metrology-enhancing materials when fabricating an OTSM. Exemplary cross-linking agents can include melamines, methylols, glycolurils, hydroxy alkyl amides, epoxy and epoxy amine resins, blocked isocyanates, or divinyl monomers, and exemplary metrology-enhancing materials may include colorants, non-actinic dyes, adhesion promoters, coating aids, speed enhancers, or surfactants, or combinations thereof.

One or more materials in an OTSM may be dissolvable in a solvent, and the solvent and/or residues can be eliminated in a drying step. Exemplary solvents may include propylene glycol mono-alkyl ether, propylene glycol alkyl (e.g. methyl) ether acetate, 2-heptanone, 3-methoxy-3-methyl butanol, butyl acetate, anisole, xylene, diglyme, ethylene glycol monoethyl ether acetate, ethylene glycol monomethyl ether, ethylene glycol monoethyl ether, diethylene glycol monoethyl ether, ethylene glycol monoethyl ether acetate, ethylene glycol monomethyl acetate, methyl ethyl ketone, or a monooxymonocarboxylic acid ester, such as methyl oxyacetate, ethyl oxyacetate, butyl oxyacetate, methyl methoxyacetate, ethyl methoxyacetate, butyl methoxyacetate, methyl ethoxyactetate, ethyl ethoxyacetate, ethoxy ethyl propionate, methyl 3-oxypropionate, ethyl 3-oxypropionate, methyl 3-methoxypropionate, ethyl 3-methoxypropionate, methyl 2-oxypropionate, ethyl 2-oxypropionate, ethyl 2-hydroxypropionate (ethyl lactate), ethyl 3-hydroxypropionate, propyl 2-oxypropionate, methyl 2-ethoxypropionate, or propyl 2-methoxy propionate, or combinations thereof. In addition, the OTSM may contain a solvent and a base additive. In addition, the solvents may include propylene glycol monomethyl ether acetate and/or cyclohexanone.

In some examples, the OTSM material can include esterified norbornene carboxylates monomers in which the carboxylate functionality can be protected by (esterified with)

acid-labile tertiary alicyclic groups. The alicyclic group can comprise a single ring (e.g. cyclopentyl, cyclohexyl or cycloheptyl), or may be polycyclic, e.g. and contain 2, 3, 4 or more bridged, fused or otherwise linked rings.

The optically tunable resist materials and/or OTSMs can be fabricated using the teachings of the present invention. Alternatively, they may be fabricated using techniques known by one skilled in the art. For example, one or more of the components of the OTSM may be fabricated by dissolving the one or more components in a suitable solvent. The polymer and photoactive components can provide good quality latent and relief images, and the metrology-enhancing components can provide features and/or structures with enhanced-metrological properties. The components of the optically tunable resist materials and/or OTSMs can be deposited using known procedures. For example, spraying, spinning, dipping, roller coating or other conventional deposition techniques may be used.

In some embodiments, the OTSM may include a polymer binder and a photoactive component. The polymer binder may include as polymerized units a monomer having an electronegative substituted group and an ester group. The monomer group includes a leaving group bonded directly to the ester group, and the ester group and/or the leaving group can be used to provide metrological enhancing properties to the OTSM. In other embodiments, a spacer component may be interposed between the ester group and a leaving group, and the ester group, the leaving group, and/or the spacer component can be used to provide metrological enhancing properties to the OTSM.

Some optically tunable resist compositions can comprise a resin binder, a PAG compound, a metrology-enhancing material, and an added non-aromatic amine component. For example, the added amine can be non-aromatic and have from about 9 to about 16 carbon atoms. In addition, the added amine can comprise either a tertiary nitrogen alicyclic ring member, or a tertiary nitrogen that is not a ring member, and can be substituted by at least two tertiary or quaternary carbon radicals When an OTSM includes a resist or an OTSM layer over an ARC layer, the ARC layer can comprise chromophore groups that can be used to prevent reflection back into the covering layer(s). For example, the chromophore groups may be present with other composition components such as the polyester resin or an acid generator compound, or the composition may comprise metrology-enhancing materials that may comprise these or other chromophore groups. Exemplary chromophores may include single ring and/or multiple ring aromatic groups, and the chromophores may be linked as pendant groups to a resin, and the polyester resin may comprise naphthalene groups and the polyacrylate resin comprises anthracene groups or other chromophores such as phenyl.

The real and imaginary refractive indices for the OTSM or its parts can be measured using ellipsometric techniques. In addition, measured and/or calculated values can be used as input parameters to a simulation tool. The simulation tool can be used to predict and/or verify the optical properties of the OTSM before and/or after the enhancement process occurs.

In some embodiments, one or more phenyl groups may be used as chromophores at 193 nm, and tunable optical properties can be provided by attaching the correct phenyl groups to the polymer.

When developing an optically tunable resist material, a monomer can be synthesized, and acid-labile groups can be introduced. For example, acid-labile groups may be used to provide base solubility, to provide etch resistance, and/or to provide metrology-enhancement properties. Polymerization processes can be performed to control the molecular weight, to create good adhesion properties, to create good structural properties, to provide good uniformity properties, and to provide enhanced metrology properties.

As used herein, resin and polymer may be used interchangeably. The term "alkyl" refers to linear, branched and cyclic alkyl. The terms "halogen" and "halo" include fluorine, chlorine, bromine, and iodine. Polymers can be used to refer to both homopolymers and copolymers and may include dimers, trimers, oligomers and the like. Monomer can be used to refer to any ethylenically or acetylenically unsaturated compound capable of being polymerized. Protecting Group is a group that can be used to protect a functional group from unwanted reactions. After application, the protecting group can be removed to reveal the original functional group. A leaving group can be a group that can be displaced in a substitution or elimination reaction.

A chromophore can be that part of a molecular entity consisting of an atom or group of atoms in which the electronic transition responsible for a given spectral band is approximately localized. In addition, a chromophore may be a molecule or group of atoms that can be used to establish optical properties by selectively absorbing or reflecting light at particular wavelengths.

In addition, a carbon alicyclic group has carbon for each ring member of the non-aromatic group. A carbon alicyclic group can have one or more endocyclic carbon-carbon double bonds, provided the ring is not aromatic. A heteroalicyclic group has at least one ring member of the non-aromatic cyclic group that is not carbon, e.g. N, O or S, typically one or two oxygen, or sulfur atoms. The heteroalicyclic group can have one or more endocyclic carbon-carbon double bonds, provided the ring is not aromatic.

Exemplary alkyl groups may have from 1 to about 10 carbon atoms, and alkyl groups may include both cyclic and non-cyclic groups. Exemplary, amine groups may include aminoalkyl groups include those groups having one or more primary, secondary and/or tertiary amine groups, and from 1 to about 12 carbon atoms.

Exemplary heteroaromatic groups may have one or more fused or linked rings and at least one ring can contain 1, 2, or 3 N, O, or S atoms such as coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl, and benzothiazole.

When fabricating an OTSM, repeating unit polymers that comprise one or more acid-labile groups may be used. The acid-labile group may be a substituted group of a heteroalicyclic or carbon alicyclic ring member. In addition, the acid-labile group may be an acid-labile ester, or the acid-labile group may also be an acetal group.

In some fabrication processes, various polymer groups/moieties may be substituted, and a substituted group may be used to provide metrology-enhancing properties. A substituted group may be substituted at one or more available positions.

In addition, some polymers can comprise one or more nitrile groups, and other polymers can comprise a lactone.

Some OTSMs may include a polymer that comprises a carbon alicyclic group fused to a polymer backbone, and the carbon alicyclic group can be a polymerized norbornene group. Polymers may include anhydride units.

In some embodiments, the OTSM can include a resin component, one or more acid generating compounds, one or more sensitizer compounds, and one or more metrology-enhancing materials. Sensitizer compound(s) may be used to improve the efficiency of the acid generator, establish, change, and/or improve the metrology-enhancement properties of the metrology-enhancing material.

In some embodiment, a method for forming a pattern having enhanced features on a wafer can include: (a) depositing an optically tunable resist on a wafer, the optically tunable resist can comprise a resin component, one or more acid generating compounds, one or more sensitizer compounds, and one or more metrology-enhancing compounds; (b) exposing the optically tunable resist to patterned activating radiation having a wavelength of less than about 200 nm and (c) developing the exposed optically tunable resist to provide the pattern having the features with enhanced metrology properties.

Exemplary sensitizer compounds may include aromatic systems, both heteroaromatic and carbocyclic aryl, including compounds that comprise separate and/or fused multi-ring aromatic systems. In addition, sensitizer compounds may be electron rich and comprise one or more electron-donating compounds having one to about twenty carbon atoms.

Exemplary acid generating compounds may include sulfonium and iodonium compounds having a cation component that comprises one or more substituted groups of naphthyl, thienyl, or pentafluorophenyl, or a cation component that has a sulfur ring group such a thienyl, benzothiophenium, etc. For example, some substituted groups (chromophores) may be used to modify the (transparency) of the acid generating compounds, while maintaining and/or increasing the effectiveness of the acid generating compounds. In addition, other substituted groups (metrology-enhancing material) may be used to modify the optical properties of the OTSM during exposure, or after exposure, or during development, or after development, or a combination thereof.

In addition, the acid generating compounds can include an iodonium or sulfonium compound that includes one more cation substituted groups selected from substituted naphthyl, substituted thienyl, and pentafluorophenyl. One or more of the sensitizer compounds can include an aromatic compound, and one or more of the metrology-enhancing compounds can include a chromophore and/or an ester. The polymer can include an acid, a nitrile, an anhydride or a lactone, or a combination thereof. The resin component may include a tetrapolymer that has repeat units. The repeat units may include a group that comprises an alicyclic group. The repeat units may also include a group that contains a polymerized monomer that can include an ethylene unsaturated carbonyl or di-carbonyl, and a group that comprises a first polymerized norbornene unit. In addition, the repeat units may include a group that comprises a second polymerized norbornene repeat unit, and the first and second norbornene units may be different. Furthermore, the repeat units may include a group that comprises metrology-enhancing material.

In some embodiments, the polymers may include pendant substituted and unsubstituted alicyclic groups such as alicyclic groups having 5 to about 18 carbons, and/or pendant nitrile groups.

In some embodiments, an OTSM may contain a resin component and a photoactive component. The resin component can comprise one or more acid-labile groups (e.g. ester or acetal groups) and one or more PAG compounds. One or more acid-labile groups/moieties can undergo a de-blocking reaction that results in different solubility characteristics in exposed and unexposed areas of the OTSM, and causes the optical properties of the developed OTSM to be different from the optical properties of the un-developed OTSM.

In other embodiments, OTSM material can include a polymer/resin that has phenolic and alkyl acrylate groups, a PAG compound, at least one of a lactic acid or an acetic acid, and at least one metrology-enhancing material. The OTSM material can be fabricated using a chemically-amplified negative resist, and/or a chemically-amplified positive resist. A base additive can be included, such as an amine, and a solvent that contains an ester may be included.

In additional embodiments, an OTSM can include a photoactive component and a resin component that comprises a polymer that includes an acid-labile ester group that has an alicyclic group, a nitrile group, a lactone group, and a metrology-enhancing group. The alicyclic group can include a bicyclic group, a tricyclic group, or a monocyclic group, such as fencyl, adamantyl, isobornyl, tricyclodecanyl, or pinnyl. The polymer can further include an acid, an anhydride, or an acid-labile group that contains a leaving group that has other than an alicyclic group/moiety and that can be used with a metrology-enhancing material.

The inventors contemplate a number of different polymers, new optically tunable resist compositions containing these polymers and methods of using these new optically tunable resist compositions to manufacture microelectronic devices. These compositions include a polymer formed from a starting polymer (e.g., epoxy cresol novolac resins) grafted with a chromophore (e.g., trimellitic anhydride, 4-hydroxybenzoic acid)

In some examples, an optically tunable polymer can be formed by reacting a starting polymer with a light-absorbing component, and/or a light-reflecting component. For example, a starting polymer may include recurring monomers that can include epoxide rings, and a chromophore can be selected from the group consisting of trimellitic anhydride and 4-hydroxybenzoic acid.

During some fabrication steps, ring-opening polymerization can be used. For example, an epoxide ring can be opened and metrology-enhancement material (such as a chromophore) may be bonded with the opened ring. Some OTSMs may include an aromatic or heterocyclic light-absorbing compound (chromophore) that can be bonded to a starting polymer as a leaving group. The chromophores may have phenolic —OH, —COOH, and —NH$_2$ functional groups, and may include thiophenes, naphthoic acid, anthracene, naphthalene, benzene, chalcone, phthalimides, pamoic acid, acridine, azo compounds, dibenzofuran, and derivatives thereof.

Some OTSMs can include a PAG and a polymer that has at least one unit with an acid-labile group and at least one blocking unit with an absorbing chromophore attached thereto. For example, the absorbing chromophore can be selected from hydrocarbon aromatic groups/moieties with one ring and heterocyclic aromatic groups/moieties with one ring, and the blocking unit can be a leaving group that can be used to de-block the absorbing chromophore from the polymer when exposed to an acid.

Different amounts of energy are required for the de-blocking processes described herein, and this required energy is known in the art as activation energy. Acid strength and/or temperature may be increased to provide a larger activation energy.

Exemplary blocking groups may have a weight average molecular weight of about 80 to about 120, and can comprise six to eight carbon atoms. Different blocking groups can require different acid concentrations and/or different amounts of heat to dissociate from the polymer/resin.

Some procedures can include depositing an OTARC material and depositing an optically tunable resist material on the OTARC material. Alternatively, an optically tunable resist material is, not required. The OTARC material can be characterized before exposure by a first set of optical properties that can be optimized, tuned and/or enhanced for an exposure process and can be characterized after exposure by a second set of optical properties optimized, tuned and/or enhanced for a measurement process. The OTARC material can include a polymer, an acid generator compound, and a metrology-enhancing material coupled to the polymer. The second set of optical properties can be established after at least one portion of the metrology-enhancing material is de-coupled, de-protected, activated, removed, or de-activated.

When the procedure includes an OTARC material, the OTARC material can include positive-acting ARC material that can be imaged and then developed using an aqueous alkaline developer. For example, the polymer may include at least one unit with an acid-labile group and at least one unit with an absorbing chromophore, and the absorbing chromophore may be selected from hydrocarbon aromatic groups/moieties with one ring and heterocyclic aromatic moieties with one ring. Exemplary absorbing chromophores can include substituted and unsubstituted phenyl, and substituted and unsubstituted heterocyclic aromatic rings containing heteroatoms selected from oxygen, nitrogen, sulfur, and combinations thereof. In addition, exemplary absorbing chromophores may include compounds containing hydrocarbon aromatic rings, substituted and unsubstituted phenyl, substituted and unsubstituted anthracyl, substituted and unsubstituted phenanthryl, substituted and unsubstituted naphthyl, and substituted and unsubstituted heterocyclic aromatic rings containing heteroatoms selected from oxygen, nitrogen, sulfur, and combinations thereof. In addition, an OTARC layer may include a dye, a chromophore, a sensitizer, an enhancer, or a color additive, or a combination thereof, and one or more of these components may be used to establish and/or change the optical properties of the OTARC.

Other procedures can include depositing an OTARC layer and depositing an OTSM layer on the OTARC layer. In these procedures, one or more of the tunable layers may be developed using an aqueous alkaline developer and one or more of the tunable layers can include a PAG and a polymer can comprise at least one unit with an acid-labile group and at least one unit with an absorbing chromophore. For example, the OTARC may include metrology-enhancing material that can be removed and/or de-activated, and an OTSM layer may include a metrology-enhancing material that is removed, activated, and/or de-protected.

In still other examples, a metrology-enhancing material can include a plurality of cross-linked polymeric particles having one or more chromophores. For example, different chromophores may be used to provide metrology-enhancing properties at different wavelengths or different bands of wavelengths. The chromophore can comprise an aromatic or substituted aromatic group/moiety, and the chromophore may be selected from phenyl, substituted phenyl, naphthyl, substituted naphthyl, anthracenyl, substituted anthracenyl, phenanthrenyl, or substituted phenanthrenyl. The chromophore can be a monomer containing one or more ($C_4$-$C_{20}$) alkyl groups. The polymeric particle can have a mean particle size of from about 1 about 50 nm, and can comprise as polymerized units one or more fluorinated monomers.

In additional embodiments, the OTSM can comprise an optically tunable resist material as a top layer, and the top layer can be substantially transparent at an exposure wavelength. An anti-reflecting material can be used as a bottom layer of the OTSM, and the bottom layer can be non-reflective at the exposure wavelength. For example, an anti-reflecting material can be deposited on a wafer thereby forming an ARC layer, and the ARC layer being substantially opaque at an exposure wavelength. An optically tunable resist layer can be deposited on the ARC layer, and the optically tunable resist layer can be substantially transparent at an exposure wavelength. The optically tunable resist layer can have tunable optical properties that can be optimized, tuned and/or enhanced for an exposure wavelength and tuned (changed) later to another set of optical properties that can be optimized, tuned and/or enhanced for wavelengths associated with a metrology process. Next, the optically tunable resist layer can be exposed using an immersion lithography tool. The first set of optical properties can be established before exposure, and the second set of optical properties can be established after exposure. For example, the optically tunable resist layer may have a higher extinction coefficient after exposure.

In some embodiments, the second set of optical properties may be determined using wavelengths associated with an inspection tool or a metrology tool.

In an enhanced profile library, the number of hypothetical profiles and corresponding simulated diffraction signals can depend, in part, on the range over which the enhanced set of parameters and the resolution at which the enhanced set of parameters are varied. The range and/or resolution used in generating data for an enhanced profile library can be selected based on the OTSM material used and/or the OTSM process used. The range and/or resolution can also be verified using AFM, X-SEM, and/or other measurement tools.

In one exemplary embodiment, the metrology subsystem 140 can generate a more accurate measured diffraction signal having additional components in the UV region, and then compare the more accurate measured diffraction signal to a more accurate simulated diffraction signal for an enhanced hypothetical profile. In addition, the more accurate simulated diffraction signal can be generated using an optimization algorithm, such as global optimization techniques, which includes simulated annealing, and local optimization techniques, which includes steepest descent algorithm. The more accurate simulated diffraction signals and enhanced hypothetical profiles can be stored in the enhanced profile library, and can be used in matching the enhanced-metrology signals in OTSM-related procedures.

Enhanced-metrology signals can have wider bandwidths and can be more accurate signals. The more accurate simulated diffraction signals can be generated with wider bandwidth data. For example, the more accurate simulated diffraction signals can be generated by applying Maxwell's equations and using a numerical analysis technique to solve Maxwell's equations, such as rigorous coupled-wave analysis (RCWA). It should be noted, however, that various numerical analysis techniques, including variations of RCWA, could be used. For a more detail description of RCWA, see U.S. patent application Ser. No. 09/770,997, titled CACHING OF INTRA-LAYER CALCULATIONS FOR RAPID RIGOROUS COUPLED-WAVE ANALYSES, filed on Jan. 25, 2001, which is incorporated herein by reference in its entirety.

An enhanced profile library can be created using wafers that have one or more enhanced structures in an OTSM layer or have one or more enhanced structures that were created using an OTSM. The new enhanced profile library can created to more accurately assess new and/or previously measured structures, and an enhanced profile library can be refined while it is being created or after it has been created, thereby providing an even more accurate assessment of a structure. The enhanced profile library can be used to identify enhanced structures and can provide process result data and recipe modification information to a processing tool. In other cases, an enhanced profile library can be used to identify an unknown structure that may be associated with an OTSM. For example, a structure may not exist in a currently developed library and an enhanced profile library may be used to extend the measurement and identification techniques into previously unused wavelengths and/or data spaces.

In addition, one or more enhanced profile libraries can be developed based on the processing sequence used to create the enhanced reference, enhanced measurement, and/or test structures. For example, enhanced profile library data can be created when an OTSM-related procedure is performed in the lithography subsystem; other enhanced profile library data can be created when an OTSM-related procedure is performed in a processing subsystem; and still other enhanced profile library data can be created when an OTSM-related procedure is performed in the metrology subsystem.

Another method for creating, using, and/or verifying enhanced profile library data can include measuring a signal off an unknown structure using an enhanced set of wavelengths, the measurement generating a measured signal having data points at the enhanced set of wavelengths; comparing the measured signal to a plurality of signals in an enhanced profile library, and if a matching condition cannot be found; entering the measured signal as un-verified data in the enhanced profile library if an enhanced library creation criteria is met.

A verification procedure can be performed using another metrology tool. The structure can be measured using an additional metrology tool, and the additional tool can generate an additional measured signal and/or profile/shape. The additional data can be compared with the previously measured data to determine if the new enhanced profile library instance can be verified. When the previously measured data cannot be verified using additional metrology data, the data can be entered into the enhanced profile library as un-verified data, or it can be removed from the enhanced profile library.

When the verification procedure is successful, an enhanced profile shape can be created to associate with the measured data. After the enhanced profile shape has been created a simulation can be performed, and the simulated signal can be compared to the previously measured signal to ensure that an accurate enhanced profile library instance has been created.

An additional method for creating enhanced profile library data can include creating an enhanced structure using an OTSM, measuring a signal off the enhanced structure with a metrology device, the measurement generating a measured signal; comparing the measured signal to a plurality of signals in a first enhanced profile library and if a matching condition cannot be found, comparing the measured signal to a plurality of signals in a second enhanced profile library, and if a matching condition cannot be found; creating a new enhanced profile data space, where the new enhanced profile data space can be created using differences between a profile data space associated with the first enhanced profile library and a profile data space associated with the second enhanced profile library, the new enhanced profile data space being associated with a new enhanced profile library.

Then, a best estimate of the measured signal can be created in the new enhanced profile data space, and an enhanced profile shape and/or enhanced profile parameters can be determined based on the best estimate of the measured signal. Next, a difference between the measured signal and the best estimate of the measured signal can be determined, and the difference can be compared to an enhanced profile library creation criteria. Then, either the best estimate of the measured signal and the enhanced profile data associated with the best estimate of the measured signal can be stored if the enhanced profile library creation criteria is met, or a corrective action can be applied if the enhanced profile library creation criteria is not met.

A best estimate of the measured signal can be created using a difference between a signal in the first enhanced profile library and a signal in the second enhanced profile library. Alternatively, a best estimate of the measured signal may be created using a signal in a library and an adjustment matrix.

In one example, applying a corrective action can include a number of steps such as creating a new estimate of the measured signal in the enhanced profile data space; a new enhanced profile shape and/or new enhanced profile parameters can be created based on the new enhanced profile signal; and an optimization technique can be performed to select the new best estimate of the measured signal. Then, calculating a difference between the measured signal and the new best estimate of the measured signal, and comparing the difference to an enhanced profile library creation criteria. Then, either the newly created best estimate of the measured signal and the enhanced profile data associated with the newly created best estimate of the measured signal can be stored if the enhanced profile library creation criteria is met, or the creating, the calculating, and the comparing steps may be stopped, if the enhanced profile library creation criteria is not met.

In other embodiments, a profile-based methodology can be used. A first enhanced shape/profile in a first enhanced profile data space can be selected, and the first enhanced shape/profile can have a first enhanced signal and a first set of enhanced profile parameters associated with it. The first enhanced profile data space can be associated with a first enhanced profile library containing previously measured shapes/profiles and associated signals. A second enhanced shape/profile in a second enhanced profile data space can be selected, and the second enhanced shape/profile can have a second enhanced signal and a second set of enhanced profile parameters associated with it. The second enhanced profile data space can be associated with a second enhanced profile library. Alternatively, the enhanced profile data spaces may be associated with the same enhanced profile library. Then, an enhanced shape/profile can be determined that can be based on a difference between the first enhanced shape/profile and the second enhanced shape/profile, and the enhanced shape/profile and associated enhanced profile signal can be defined by enhanced profile parameters. In some cases, the differences between diffracted signals, refracted signals, reflected signals, transmitted signals, or received signals, or a combination thereof can be used to create enhanced profile library data. In other cases, the differences between diffracted spectra, refracted spectra, reflected spectra, transmitted spectra, or received spectra, or a combination thereof can be used to create enhanced profile library data.

When un-enhanced data is created, the un-enhanced profile data can be stored in an un-enhanced profile library. The un-enhanced profile library can be created at an un-enhanced resolution, and the un-enhanced profile library can encompass un-enhanced profile data spaces having data points with un-enhanced accuracies. The data points can represent un-enhanced profile parameters and associated un-enhanced profile signals, and the un-enhanced profile library can include a plurality of un-enhanced profiles.

When a refinement and/or enhancement procedure is performed, the resulting data can be stored as enhanced data in an enhanced profile library. A refinement and/or enhancement procedure can include a series of steps designed to determine enhanced profile library data using un-enhanced data associated with the un-enhanced signals, un-enhanced data associated with the un-enhanced profiles, and other data from and/or derived from the un-enhanced profile data spaces.

The enhanced data can be created at a specified resolution that can be dependent upon the metrology-enhancing material being used, and the enhanced profile library can encompass an enhanced profile data space having data points with a specified accuracy. The enhanced data points can represent enhanced (more accurate) profile parameters, enhanced profile signals, and enhanced profile shapes, and the enhanced data points can be associated with a particular OTSM and stored in the enhanced profile library.

An accuracy value for the enhanced data points of the enhanced profile library can be specified and/or verified. In addition, an accuracy value for the un-enhanced data points of an un-enhanced profile library can be specified and/or verified. The enhanced profile library can be created at a specified resolution and/or accuracy. Enhanced tolerances and/or limits can be established for the enhanced profile shape, for the enhanced profile signals, and for the enhanced profile parameters in the enhanced profile library.

Enhanced resolution values can be determined for the enhance data points in the enhanced profile data space, and the enhanced resolution values can be designed to ensure that the specified accuracy value exists for the enhanced data points associated with a particular OTSM, and the enhanced data points of the enhanced profile data space can be created using the enhanced resolution values.

Before, during, and/or after a refinement and/or enhancement procedure is performed one or more sensitivity matrices can be calculated, the sensitivity matrix being a measure of change of the signal induced by a change in the profile parameter, and a sensitivity matrix can be used to determine an optimum refined resolution for each enhanced profile parameter.

The enhanced profile library can be used to measure and/or identify an integrated circuit structure, and the measurement and/or identification procedure can include a series of steps designed to determine a enhanced profile shape, enhanced profile signal, and enhanced profile parameters to identify a structure, such as an integrated circuit structure.

In some cases, reference and/or test structures can be fabricated using an enhanced-metrology procedure and can be used when using, creating, refining, and/or verifying an enhanced profile library. For example, a reference and/or test structure may not exist in a currently developed library and an enhanced profile library may be used to extend the measurement and identification techniques into previously unused wavelengths and/or data spaces. For example, the reference and/or test structures can be fabricated in an OTSM, or an OTARC, or a combination thereof, and/or the reference and/or test structures can be fabricated using an OTSM, or an OTARC, or a combination thereof.

One exemplary method of using an enhanced profile library to determine the profile of an integrated circuit structure can include measuring a signal off a structure with a metrology device, the measurement generating a measured signal. In a first comparison step, the measured signal can be compared to a plurality of signals in an enhanced profile library, and the first comparison step can be stopped if a first matching criteria is met. In a second comparison step, the measured signal can be compared to a plurality of signals in an un-enhanced profile library, and the second comparison step can be stopped if a second matching criteria is met. Alternatively, a different number (1-N) of libraries may be used. The libraries can include un-enhanced data and/or enhanced data.

A difference can be calculated using the measured data and enhanced profile library data, and the difference can be compared to an enhanced profile library creation criteria. Alternatively, the difference can be determined using measured data and un-enhanced profile library data. It should be understood that when differences are discussed herein the differences can be scalars, vectors, matrices, and/or tensors. Then, either the structure can be identified using the enhanced profile data associated with the match if the enhanced profile library creation criteria is met, or a corrective action can be applied if the enhanced profile library creation criteria is not met.

In the various examples discussed herein, applying a corrective action can include selecting a new OTSM material, selecting a new OTSM fabricating process, selecting a new wafer, determining a new enhanced profile signal, creating a new enhanced profile signal, determining a new enhanced profile shape, creating a new enhanced profile shape, selecting a different library, creating a new enhanced profile library, using a different enhanced profile library creation criteria, using different wavelengths, performing a refinement procedure, performing an enhancement procedure, performing an accuracy improvement procedure, performing a sensitivity analysis, performing a clustering procedure, performing a regression procedure, performing an optimization procedure, performing a simulation procedure, or using different metrology data, or a combination thereof.

In the various embodiments discussed herein, the enhanced profile library data can be created, selected, determined, refined, verified, compared, simulated, stored, and/or used in real-time to minimize storage requirements, minimize processing times, and maximize throughput. Alternatively, dynamic processing may not be required.

When enhanced profile library comprises data for enhanced structures created in an OTSM and/or created using an OTSM, accuracy values and limits can be determined for the enhanced structures based on the OTSM materials and/or procedure being used. The accuracy values and limits can be established for OTSM-related profile signals, OTSM-related profile shapes, and/or OTSM-related profile parameters associated with the OTSM-related (enhanced) structures. In addition, accuracy values and limits can be established for OTSM-related data. Accuracy testing can be performed using operational limits, warning limits, and/or error limits based on the OTSM materials and/or procedure being used. For example, warning messages can be sent when operational limits are exceeded, and error messages can be sent when warning limits are exceeded.

During a semiconductor manufacturing process, one or more OTSM-related databases and/or libraries can be created, modified, and/or stored for later use. An OTSM-related database can include measured data at measurement sites that are dependent on the OTSM-related process being performed. The databases can include predicted measured data, predicted accuracy data, and/or predicted process data. The databases can include confidence values for measured data, for accuracy data, for library data, for historical data, and/or for process data. The databases can include data from OTSM-related procedures. An error condition can be declared when OTSM-related database cannot be accessed.

In some embodiments, an OTSM-related problem can cause a wafer to be re-worked. One or more layers can be removed and new materials can be deposited on the wafer. For example, an OTSM layer, or an OTARC layer, or a resist layer, or a BARC/ARC layer, or a combination thereof may be removed and re-deposited.

When designing, fabricating, and or using an OTSM, a number of parameters can be considered including resolution, contrast, sensitivity, etch resistance, and tunable optical properties. The tunability and/or resolution of an OTSM can be controlled by one or more physical and/or chemical characteristics of the OTSM material. OTSM contrast can be characterized by the ability of an OTSM to differentiate between the exposed and unexposed regions within the aerial image.

For example, a contrast curve may be generated to characterize the contrast of an OTSM. A contrast curve can be generated by exposing an OTSM to varying radiation doses and measuring the OTSM remaining after a pre-determined development time.

In addition, one or more optical properties curve may be generated to characterize the metrology-enhancing properties of an OTSM. A reflectance, absorbance, and/or contrast curve can be generated by exposing an OTSM to varying radiation doses and measuring the OTSM before and after exposure. Diffraction, reflection, and/or transmission signals can also be used. In addition, optical properties such as extinction coefficients and/or indices of refraction can be used. DOEs may be used to determine the optimum development time and/or optimum wavelengths to use.

Additional characteristics of an OTSM may include, but are not limited to: ability to spin-coat uniformly, compatible thermal and mechanical properties, good adhesion properties, excellent dissolution in aqueous base developers, chemical amplification of the metrology-enhancing material using an acid-labile protecting group, tunable optical transparency properties, and/or optimized etch resistance properties.

In some OTSMs, the polymer can be used to provide the plasma etch resistance of the OTSM, so the OTSM can be to be used as a mask to pattern underlying layers. For example, the carbon content of the polymer and/or the acid-labile protecting groups may be controlled to improve the etch resistance, and alicyclic hydrocarbons may be used to increase the etch resistance.

In some OTSMs, when the patterns are generated in the OTSM by exposure to UV radiation through a mask, the metrology-enhancing material can be activated by the exposure step, and the optical properties of an upper portion of the OTSM can be changed. In the exposed areas, the PAG decomposes forming an acid species. During baking, the acid diffuses and catalyzes a de-protection reaction rendering the insoluble portion of the OTSM soluble in a developer. The soluble regions of the OTSM can be removed with the aqueous base developer, and the upper portion of the remaining features and/or structures can have enhanced metrology properties. In these OTSMs, the amount of metrology-enhancing material activated can be controlled by the exposure process.

In other OTSMs, when the patterns are generated in the OTSM by exposure to UV radiation through a mask. In the exposed areas, the PAG decomposes forming an acid species that can activate the metrology-enhancing material, and the optical properties of an upper portion of the OTSM can be changed. During baking, the acid diffuses and catalyzes a de-protection reaction rendering the insoluble portion of the OTSM soluble in a developer. The soluble regions of the OTSM can be removed with the aqueous base developer, and the upper portion of the remaining features and/or structures can have enhanced metrology properties. In these OTSMs, the amount of metrology-enhancing material activated can be controlled by the initial acid generation process.

In additional OTSMs, patterns can be generated in the OTSM by exposure to UV radiation through a mask, and the PAG can decompose in the exposed areas forming an acid species that can activate the metrology-enhancing material, and the optical properties of an upper portion of the OTSM can be changed. During baking, the acid diffuses and catalyzes a de-protection reaction rendering the insoluble portion of the OTSM soluble in a developer. In addition, the acid can catalyze another de-protection reaction that can be used to further the activation of the metrology-enhancing material. The soluble regions of the OTSM can be removed with the aqueous base developer, and a substantial portion of the remaining features and/or structures can have enhanced metrology properties. In these OTSMs, the amount of metrology-enhancing material activated can be controlled by the initial acid generation process and the acid diffusion process.

During a library development process, one or more verification wafers can be processed and used to establish known process results, and metrology-enhancement procedures can be performed to measure the periodic structures and characterize the expected optical response. Additional measurements can then be made using other measurement tools to verify the results obtained during the metrology-enhancement procedures.

When enhanced libraries are being created, the measurement site(s) may be selected from a set of previously defined sites. For example, historical data for a metrology tool may include data taken at a number of sites, and one or more historical sites can be used. Alternatively, a measurement site may not be selected from a set of previously defined sites.

When a new metrology-enhancement measurement site is required, a new control strategy including a new metrology-enhancement metrology recipe can be created, and the new recipe can be used to instruct the metrology tool to make additional enhanced measurements at the one or more new sites.

Metrology-enhancement procedures can be updated using feedback data that can be generated by running monitor, test, and/or production wafers, varying the process settings and observing the results, then updating one or more different applications. For example, a metrology-enhancement update can take place every N processing hours by measuring the before and after characteristics of a monitor wafer. By changing the settings over time to check different operating regions, the complete operating space can be validated over time. In addition, several wafers can be run at the same time with different recipe settings.

When metrology-enhancement procedures are being performed, the data sources and/or libraries may be important and may be identified in advance. For example, metrology-enhancement data may be either externally generated or internally generated. In addition, business rules can be provided that can be used to determine when to use an externally generated or an internally generated data. Metrology-enhancement procedures and/or libraries must be evaluated and pre-qualified before they can be used.

Although only certain embodiments of this invention have been described in detail above, those skilled in the art will readily appreciate that many modifications are possible in the embodiments without materially departing from the novel teachings and advantages of this invention. Accordingly, all such modifications are intended to be included within the scope of this invention.

Thus, the description is not intended to limit the invention and the configuration, operation, and behavior of the present invention has been described with the understanding that modifications and variations of the embodiments are possible, given the level of detail present herein. Accordingly, the preceding detailed description is not mean or intended to, in any way, limit the invention—rather the scope of the invention is defined by the appended claims.

What is claimed is:

1. A method of improving an optical metrology process comprising:
providing a substrate having a material layer thereon;
depositing a resist layer on the material layer, wherein the resist layer comprises a first set of optical properties optimized, tuned and/or enhanced for an exposure process, the resist layer including one or more non-polymeric silicon additives;
exposing the resist layer to patterned radiation created using a reticle and a radiation source, wherein the radiation source has a wavelength below approximately 300 nm;
creating a plurality of un-enhanced structures in the resist layer by developing the exposed resist layer, wherein the plurality of un-enhanced structures comprise at least one un-enhanced measurement structure; and
creating a plurality of enhanced structures in the resist layer by enhancing the plurality of un-enhanced structures, wherein at least one enhanced measurement structure is created by enhancing the at least one un-enhanced measurement structure using at least one of the non-polymeric silicon additives, the plurality of enhanced structures being characterized by a second set of optical properties.

2. The method of claim 1, wherein the resist layer comprises a photoresist material, or an anti-reflective material, or a combination thereof.

3. The method of claim 1, wherein the plurality of enhanced structures are created by exposing the plurality of un-enhanced structures in the resist layer to reactive gas, a liquid, plasma, radiation, or thermal energy, or any combination thereof, and wherein the at least one enhanced measurement structure is created by exposing the at least one un-enhanced measurement structure to a reactive gas, a liquid, plasma, radiation, or thermal energy, or any combination thereof.

4. The method of claim 1, wherein the plurality of enhanced structures are created by changing at least one optical property of the resist layer using a reactive gas, a liquid, plasma, radiation, or thermal energy, or any combination thereof, and wherein the at least one enhanced measurement structure is created by changing at least one other optical property of the resist layer using a reactive gas, a liquid, plasma, radiation, or thermal energy, or any combination thereof, wherein the resist layer comprises a photoresist material, or an anti-reflective material, or a combination thereof.

5. The method of claim 1, wherein the plurality of enhanced structures are created by removing at least one portion of the resist layer, and the at least one enhanced measurement structure is created by removing at least one other portion of the resist layer.

6. The method of claim 1, wherein the substrate comprises semiconductor material, dielectric material, glass material, ceramic material, or metallic material, or any combination thereof, and wherein the material layer comprises low-k material, ultra low-k material, planarization material, dielectric material, glass material, ceramic material, or metallic material, or any combination thereof.

7. The method of claim 1, wherein the first set of optical properties includes first reflectance data established before the exposing and the second set of optical properties includes second reflectance data established after the exposing.

8. The method of claim 1, wherein the first set of optical properties includes first diffraction signal data established before the exposing and the second set of optical properties includes second diffraction signal data established after the exposing.

9. The method of claim 1, wherein the first set of optical properties includes first contrast data established before the exposing and the second set of optical properties includes second contrast data established after the exposing.

10. The method of claim 1, further comprising:
measuring the substrate after creating the plurality of enhanced structures, wherein a measured diffraction spectrum is obtained from the at least one enhanced measurement structure and is characterized by the second set of optical properties;
selecting a best estimate structure and associated best estimate diffraction spectrum from a library of enhanced structures and associated diffraction spectrums;
calculating a difference between the measured diffraction spectrum and the best estimate diffraction spectrum;
comparing the difference to a product requirement; and
either continuing to process the substrate if the product requirement is met, or
applying a first corrective action if the product requirement is not met.

11. The method of claim 10, further comprising:
identifying the at least one enhanced measurement structure using the best estimate structure associated with the best estimate diffraction spectrum if the product requirement is met.

12. The method of claim 10, further comprising:
establishing an accuracy value for the substrate, and for data associated with the at least one enhanced measurement structure if the product requirement is met.

13. The method of claim 10, wherein the applying of the first corrective action comprises reworking the substrate by removing the resist layer that remains.

14. The method of claim 10, wherein the applying of the first corrective action comprises re-measuring the substrate.

15. The method of claim 10, wherein the applying of the first corrective action comprises:
selecting a new enhanced profile data space, wherein the new enhanced profile data space is determined using the measured diffraction spectrum, enhanced profile library data, substrate data, process data, or historical data, or any combination thereof;
determining a new best estimate signal and/or a new best estimate structure within the new enhanced profile data space, wherein a new enhanced profile shape and/or new enhanced profile parameters are established;
calculating a difference between the measured diffraction spectrum and the new best estimate signal;
comparing the difference to a first enhanced profile library creation criteria; and
identifying the at least one enhanced measurement structure using the new enhanced profile shape associated with the new best estimate signal if the first enhanced profile library creation criteria is met.

16. The method of claim 15, further comprising:
storing the new best estimate signal and the new enhanced profile shape associated with the measured diffraction spectrum if the first enhanced profile library creation criteria is met.

17. The method of claim 10, wherein the continuing to process the substrate comprises:
creating a second set of enhanced structures in the material layer using the plurality of enhanced structures in the resist layer as a mask;
removing the resist layer that remains; and depositing a second material into the second set of enhanced structures in the material layer.

18. The method of claim 17, wherein the material layer comprises semiconductor material, dielectric material, glass material, ceramic material, or metallic material, or a combination thereof, and wherein the second material comprises semiconductor material, dielectric material, or metallic material, or a combination thereof.

19. The method of claim 17, further comprising:
obtaining a second set of measurement data for the second set of enhanced structures in the material layer;
calculating a second difference between the second set of measured data and a second set of required data;
comparing the second difference to a second product requirement; and either
continuing to process the substrate if the second product requirement is met, or
applying a second corrective action if the second product requirement is not met.

20. The method of claim 15, further comprising:
calculating the new best estimate structure by changing a height, a width, a thickness, a depth, a volume, an area, an angle, a dielectric property, a process recipe parameter, a processing time, a critical dimension, a spacing, a period, a position, or a line width, or any combination of two or more thereof, and
simulating the new best estimate signal using the new best estimate structure.

21. The method of claim 10, further comprising:
selecting the best estimate structure by changing a height, a width, a thickness, a depth, a volume, an area, an angle, a dielectric property, a process recipe parameter, a processing time, a critical dimension, a spacing, a period, a position, or a line width, or any combination of two or more thereof, and
simulating the associated best estimate diffraction spectrum using the best estimate structure.

22. The method of claim 1, wherein an anti-reflective layer is deposited on the material layer before depositing the resist layer.

23. The method of claim 1, wherein the second set of optical properties are optimized, tuned and/or enhanced for a measurement process, a metrology tool, an inspection process, or an inspection tool, or any combination thereof, the first and second sets of optical properties being established at one or more wavelengths in a range from approximately 100 nm to approximately 1000 nm.

24. The method of claim 1, wherein the first set of optical properties includes a first extinction coefficient of less than approximately 0.5 at an exposure wavelength before the exposing and the second set of optical properties includes a second extinction coefficient of greater than approximately 0.5 at the exposure wavelength after the exposing.

25. The method of claim 1, wherein the first set of optical properties includes a first index of refraction ($n_1$), the first index of refraction ($n_1$) being established between about 1.0 and about 2.8 in a first range of wavelengths around an exposure wavelength and between about 1.0 and about 4.8 in a second range of wavelengths above the exposure wavelength, and wherein the second set of optical properties includes a second index of refraction ($n_2$), the second index of refraction ($n_2$) being established between about 1.2 and about 6.8 in a range of wavelengths above the exposure wavelength.

26. The method of claim 1, wherein the first set of optical properties includes a first index of refraction ($n_1$), the first index of refraction ($n_1$) being established between about 1.0 and about 2.8 in a first range of wavelengths around an exposure wavelength and between about 1.0 and about 4.8 in a second range of wavelengths above the exposure wavelength, and wherein the second set of optical properties includes a second index of refraction ($n_2$), the second index of refraction ($n_2$) being established between about 1.2 and about 6.8 in a range of wavelengths established for a measurement process.

27. The method of claim 1, wherein the first set of optical properties includes a first reflection coefficient ($k_1$), the first reflection coefficient ($k_1$) being established between about 0.1 and about 0.8 in a first range of wavelengths around an exposure wavelength and between about 0.2 and about 1.8 in a second range of wavelengths above the exposure wavelength, and wherein the second set of optical properties includes a second reflection coefficient ($k_2$), the second reflection coefficient $k_2$ being established between about 0.2 and about 2.8 in a range of wavelengths above the exposure wavelength.

28. The method of claim 1, wherein the first set of optical properties includes a first reflection coefficient ($k_1$), the first reflection coefficient ($k_1$) being established between about 0.1 and about 0.8 in a first range of wavelengths around an exposure wavelength and between about 0.2 and about 1.8 in a second range of wavelengths above the exposure wavelength, and wherein the second set of optical properties includes a second reflection coefficient ($k_2$), the second reflection coefficient $k_2$ being established between about 0.2 and about 2.8 in a range of wavelengths established for a measurement process.

29. The method of claim 1, wherein the radiation source operates at approximately 248 nm, or approximately 193 nm, or approximately 157 nm, or below approximately 157 nm.

30. The method of claim 1, wherein the plurality of enhanced structures comprise a gate structure, a doping structure, a trench structure, a via structure, a dual damascene structure, a mask structure, a periodic structure, a grating, or an array, or any combination thereof.

31. The method of claim 1, wherein the first set of optical properties are established using a resist layer component having a tunable index of refraction ($n_T$), wherein the tunable index of refraction ($n_T$) is established between about 1.2 and about 2.8 in a first range around 248 nm and established between about 1.0 and about 3.8 in a second range above 248 nm, or is established between about 1.2 and about 2.8 in a first range around 193 nm and established between about 1.0 and about 3.8 in a second range above 193 nm, or is established between about 1.2 and about 2.8 in a first range around 157 nm and established between about 1.0 and about 3.8 in a second range above 157 nm, or is established between about 1.2 and about 2.8 in a first range around 126 nm and established between about 1.0 and about 3.8 in a second range above 126 nm, or is established between about 1.2 and about 2.8 in a first extreme ultraviolet range below 126 nm and established between about 1.0 and about 3.8 in a second range above the first extreme ultraviolet range, or any combination of two or more thereof.

32. The method of claim 1, wherein the second set of optical properties are established using a resist layer component having a tunable index of refraction ($n_T$), wherein the tunable index of refraction ($n_T$) is established between about 1.2 and about 2.8 in a first range around 248 nm and established between about 1.0 and about 3.8 in a second range above 248 nm, or is established between about 1.2 and about 2.8 in a first range around 193 nm and established between about 1.0 and about 3.8 in a second range above 193 nm, or is established between about 1.2 and about 2.8 in a first range around 157 nm and established between about 1.0 and about 3.8 in a second range above 157 nm, or is established between about 1.2 and about 2.8 in a first range around 126 nm and established between about 1.0 and about 3.8 in a second range above 126 nm, or is established between about 1.2 and about 2.8 in a first extreme ultraviolet range below 126 nm and established between about 1.0 and about 3.8 in a second range above the first extreme ultraviolet range, or any combination of two or more thereof.

33. The method of claim 1, wherein the first set of optical properties are established using a resist layer component having a tunable reflection coefficient ($k_T$), wherein the tunable reflection coefficient ($k_T$) is established between about 0.2 and about 0.8 in a first range around 248 nm and established between about 0.5 and about 3.0 in a second range above 248 nm, or is established between about 0.2 and about 0.8 in a first range around 193 nm and established between about 0.5 and about 3.0 in a second range above 193 nm, or is established between about 0.2 and about 0.8 in a first range around 157 nm and established between about 0.5 and about 3.0 in a second range above 157 nm, or is established between about 0.2 and about 0.8 in a first range around 126 nm and established between about 0.5 and about 3.0 in a second range above 126 nm, or is established between about 0.2 and about 0.8 in a first extreme ultraviolet range below 126 nm and established between about 0.5 and about 3.0 in a second range above the first extreme ultraviolet range, or any combination of two or more thereof.

34. The method of claim 1, wherein the second set of optical properties are established using a resist layer component having a tunable reflection coefficient ($k_T$), wherein the tunable reflection coefficient ($k_T$) is established between about 0.2 and about 0.8 in a first range around 248 nm and established between about 0.5 and about 3.0 in a second range above 248 nm, or is established between about 0.2 and about 0.8 in a first range around 193 nm and established between about 0.5 and about 3.0 in a second range above 193 nm, or is established between about 0.2 and about 0.8 in a first range around 157 nm and established between about 0.5 and about 3.0 in a second range above 157 nm, or is established between about 0.2 and about 0.8 in a first range around 126 nm and established between about 0.5 and about 3.0 in a second range above 126 nm, or is established between about 0.2 and about 0.8 in a first extreme ultraviolet range below 126 nm and established between about 0.5 and about 3.0 in a second range above the first extreme ultraviolet range, or any combination of two or more thereof.

35. A method of improving an optical metrology process comprising:
receiving a substrate, wherein the substrate comprises a plurality of dies and a number of measurement sites, each die having a first patterned optically tunable resist layer on top of at least one optically tunable bottom anti-reflective coating (BARC) layer, and at least one measurement site having a periodic measurement structure therein;
determining an accuracy value for the substrate;
modifying at least one optical property of the substrate by modifying the first patterned optically tunable resist layer and the optically tunable BARC layer, when the accuracy value is not within limits established for an enhanced substrate; and
processing the substrate, when the accuracy value is within limits established for the enhanced substrate.

36. The method of claim 35, wherein the modifying at least one optical property of the substrate further comprises:
modifying at least one optical property of a first periodic measurement structure in at least one measurements site on the substrate using a reactive gas, a liquid, or plasma, or a combination thereof.

37. The method of claim 35, wherein the modifying at least one optical property of the substrate further comprises:
modifying at least one optical property of a resist material in the first patterned optically tunable resist layer, or an anti-reflective material in the optically tunable BARC layer, or a combination thereof.

38. The method of claim 35, wherein the modifying at least one optical property of the substrate further comprises:
removing at least one portion of a resist material in the first patterned optically tunable resist layer, or an anti-reflective material in the optically tunable BARC layer, or a combination thereof.

39. The method of claim 35, further comprising:
measuring the modified substrate, wherein a new accuracy value is determined for the measured substrate;
obtaining a measured diffraction spectrum from the modified substrate;
selecting a best estimate structure from a library of periodic structures and associated diffraction spectrums;
obtaining a best estimate diffraction spectrum associated with the best estimate structure;
comparing the measured diffraction spectrum to the best estimate diffraction spectrum; and either
establishing an accuracy value for the substrate and measured diffraction spectrum data when the measured diffraction spectrum and the best estimate diffraction spectrum match within a matching criterion, or
selecting a new best estimate structure when the measured diffraction spectrum and the best estimate diffraction spectrum do not match within the matching criterion.

40. The method of claim 39, wherein the new best estimate structure is created by changing a height, a width, a thickness, a depth, a volume, an area, a dielectric property, a process recipe parameter, a processing time, a critical dimension, a spacing, a period, a position, or a line width, or any combination of two or more thereof.

41. The method of claim 39, further comprising:
comparing the measured diffraction spectrum to a new best estimate diffraction spectrum associated with the new best estimate structure;
when the measured diffraction spectrum and the new best estimate diffraction spectrum match within a new matching criterion, establishing the new accuracy value for the substrate; and
when the measured diffraction spectrum and the new best estimate diffraction spectrum do not match within the new matching criterion, continuing to determine new best estimate diffraction spectrums until the measured diffraction spectrum and the new best estimate diffraction spectrum match within the new matching criterion, or until a difference between the measured diffraction spectrum and the new calculated hypothetical diffraction spectrum match is greater than a limit value.

42. The method of claim 41, further comprising:
storing the new accuracy value, the new best estimate structure, and diffraction spectrum associated with the new best estimate structure when the measured diffraction spectrum and the new best estimate diffraction spectrum match within the new matching criterion.

* * * * *